US008470352B2

(12) United States Patent
Liu et al.

(10) Patent No.: US 8,470,352 B2
(45) Date of Patent: *Jun. 25, 2013

(54) MAGNESIUM COMPOSITIONS AND USES THEREOF FOR METABOLIC DISORDERS

(75) Inventors: Guosong Liu, Palo Alto, CA (US); Fei Mao, Fremont, CA (US)

(73) Assignee: Magceutics, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/357,216

(22) Filed: Jan. 24, 2012

(65) Prior Publication Data

US 2012/0157533 A1 Jun. 21, 2012

Related U.S. Application Data

(63) Continuation of application No. 12/054,374, filed on Mar. 24, 2008, now Pat. No. 8,163,301.

(60) Provisional application No. 61/066,592, filed on Feb. 20, 2008, provisional application No. 60/994,902, filed on Sep. 20, 2007, provisional application No. 60/896,458, filed on Mar. 22, 2007.

(51) Int. Cl.
*A01N 25/08* (2006.01)
*A01N 59/06* (2006.01)
*A61K 33/06* (2006.01)

(52) U.S. Cl.
USPC .......................................... 424/410; 424/682

(58) Field of Classification Search
USPC ................................................. 424/410, 682
See application file for complete search history.

(56) References Cited

U.S. PATENT DOCUMENTS

| 4,788,180 | A | 11/1988 | Bloch et al. |
| 5,002,774 | A | 3/1991 | Agrawala et al. |
| 6,835,398 | B2 | 12/2004 | Cohen |
| 2005/0129762 | A1 | 6/2005 | Heaton et al. |
| 2005/0214388 | A1 | 9/2005 | Gorham et al. |
| 2007/0098843 | A1 | 5/2007 | Tomohira |
| 2007/0128279 | A1 | 6/2007 | Edgren et al. |
| 2011/0020443 | A1 | 1/2011 | Liu et al. |

FOREIGN PATENT DOCUMENTS

| CN | 1207294 A | 2/1999 |
| GB | 1422193 A | 1/1976 |

OTHER PUBLICATIONS

Fine, et al. Diagnosis of magnesium-induced diarrhea. N Engl J Med. Apr. 11, 1991;324(15):1012-7.

(Continued)

*Primary Examiner* — Benjamin Packard
(74) *Attorney, Agent, or Firm* — Wilson Sonsini Goodrich & Rosati

(57) ABSTRACT

A composition for administration to a subject, such as oral administration to a subject, for example, has been provided. Such a composition may comprise at least one magnesium-counter ion compound. A magnesium-counter ion composition described herein may be useful for any of a variety of applications provided herein, such as maintaining, enhancing, and/or improving health, nutrition, and/or another condition of a subject, and/or cognitive, learning, and/or memory function. A magnesium-counter ion composition provided herein may be useful for administration to a subject presenting magnesium deficiency, mild cognitive impairment, Alzheimer's disease, attention deficit hyperactivity disorder, ALS, Parkinson's disease, diabetes, migraine, anxiety disorder, mood disorder, and/or hypertension. A kit, method, and other associated technology are also provided.

14 Claims, 29 Drawing Sheets

OTHER PUBLICATIONS

Fine, et al. Intestinal absorption of magnesium from food and supplements. J Clin Invest. Aug. 1991;88(2):396-402.

Hocking, M. B. Handbook of Chemical Technology and Pollution Control. 3rd Ed. Academic Press. 2005; p. 540.

Iannelli, et al., about.com guide, Jul. 31, 2005, p. 1, Accessed Feb. 25, 2012.

International search report dated Aug. 31, 2010 for PCT Application No. US10/40849.

Quamme, G. Recent developments in intestinal magnesium absorption. Curr Opin Gastroenterol. Mar. 2008;24(2):230-5.

Rude, et al. Renal tubular maximum for magnesium in normal, hyperparathyroid, and hypoparathyroid man. J Clin Endocrinol Metab. Dec. 1980;51(6):1425-31.

U.S. Appl. No. 13/736,679, filed Jan. 18, 2013, Liu et al.

European search report dated Jan. 16, 2013 for EP Application No. 10794801.0.

Office action dated Feb. 29, 2012 for U.S. Appl. No. 12/829,361.
Office action dated Aug. 1, 2011 for U.S. Appl. No. 12/054,367.
Office action dated Aug. 1, 2011 for U.S. Appl. No. 12/054,371.
Office action dated Aug. 1, 2011 for U.S. Appl. No. 12/054,373.
Office action dated Aug. 1, 2011 for U.S. Appl. No. 12/054,384.
Office action dated Aug. 3, 2011 for U.S. Appl. No. 12/054,368.
Office action dated Sep. 8, 2011 for U.S. Appl. No. 12/054,374.
Office action dated Oct. 2, 2012 for U.S. Appl. No. 13/402,648.
Office action dated Nov. 16, 2010 for U.S. Appl. No. 12/054,371.
Office action dated Nov. 22, 2010 for U.S. Appl. No. 12/054,373.
Office action dated Nov. 23, 2010 for U.S. Appl. No. 12/054,367.
Office action dated Nov. 23, 2010 for U.S. Appl. No. 12/054,384.
Office action dated Dec. 22, 2010 for U.S. Appl. No. 12/054,374.
Office action dated Mar. 20, 2013 for U.S. Appl. No. 13/402,648.

A

B                                    C

A

B

A

B

C

MAGNESIUM COMPOSITIONS AND USES THEREOF FOR METABOLIC DISORDERS

CROSS REFERENCE

This application is a continuation of U.S. application Ser. No. 12/054,374, filed on Mar. 24, 2008, which claims the benefit of U.S. Provisional Patent Application Ser. Nos. 60/896,458, 60/994,902, and 61/066,592, filed on Mar. 22, 2007, Sep. 20, 2007, and Feb. 20, 2008 respectively, all of which are incorporated herein by reference in their entirety.

BACKGROUND OF THE INVENTION

Magnesium is present in the human body and plays multiple roles. At the molecular level, magnesium is a cofactor for over 300 enzymes responsible for some of the most important biological activities in mammals, including humans. In living cells, magnesium is involved in the homeostasis of other minerals, such as sodium, potassium and calcium, and the formation, transfer, storage and utilization of adenosine triphosphate (ATP), a principal source of energy in living cells. In the human body, magnesium is involved in the maintenance of normal muscle and nerve function, heart rhythm, bone strength, and immune system health. Magnesium is also involved in the regulation of blood sugar levels and the promotion of normal blood pressure.

It has been reported that magnesium plays a role in the regulation of synaptic plasticity (Slutsky et al., *Neuron*, 44, 835-849 (2004)), a cellular process believed to be involved in organization of neural circuits during early development and in storage of information in later stages. Magnesium appears to be involved in selective suppression of so-called background synaptic activity, or background noise, during which meaningful neuronal signals are unaffected. Magnesium thus appears to increase the signal to noise ratio (S/N) of synaptic transmission and thereby enhance synaptic plasticity.

Synapses are generally less plastic in the aging or diseased brain. Loss of plasticity in the hippocampus, a brain region associated with short-term memory, may cause forgetfulness that is common in older people. Such loss of plasticity may lead to pathological conditions associated with mild cognitive impairment (MCI) or, more seriously, with Alzheimer's disease (AD). As to the latter, it has been reported that deceased humans who had been afflicted with AD had significantly lower levels of magnesium in regions of their brains than did deceased humans of the same age who had not been afflicted with AD (Andrasi et al., *Magnesium Res.* 13(3), 189-196 (2000)). As to aging effects, it has been reported that supplementing the diet of aging rats with magnesium appears to increase the expression level of a particular brain molecule, the NMDA receptor, an effect associated with improvement of cognitive function (U.S. Patent Application Publication No. US 2006/0089335 A1)

Despite the physiological role of magnesium in human health, people may not consume enough of the mineral in their diets. Studies have shown that the dietary intake of magnesium has historically been inadequate in the U.S. population (Ford et al., (2003) *J. Nutr.* 133, 2879-2882) or relatively low for certain population segments (Institute of Medicine, *For Calcium, Phosphorus, Magnesium, Vitamin D, and Flouride*, 202 and 393 (1997)). Magnesium deficit may lead to or may be associated with many pathological symptoms, such as loss of appetite, nausea, vomiting, fatigue, seizures, abnormal heart rhythms, diabetes, and/or cardiovascular disease, for example. According to several studies, magnesium deficit may lead to or may be associated with attention deficit hyperactivity disorder (ADHD) in children and symptoms associated therewith (Kozielec et al., *Magnes. Res.* 10(2), 143-148 (1997) and Mousain-Bosc et al., Magnes. Res. 19(1), 46-52 (2006)).

Commercially available magnesium supplements include magnesium oxide tablets or capsules, various inorganic magnesium compounds, such as magnesium hydroxide and magnesium sulfate, for example, various organic acid magnesium salt compounds, such as magnesium salts of gluconic acid, citric acid, and lactic acid, for example, and various magnesium chelate compounds. Magnesium oxide may be high in elemental magnesium content, but very low in magnesium bioavailability, or absorption rate in the human body (Ranade et al., *Am. J. Therapeut.* 8(5), 345-357 (2001)). Inorganic magnesium compounds, such as magnesium hydroxide and magnesium sulfate, may also be poor in terms of magnesium bioavailability and may give rise to an undesirable side-effect, diarrhea. Organic acid magnesium salt compounds, such as magnesium salts of gluconic acid, citric acid and lactic acid, may be associated with gastrointestinal distress, laxative effect, and/or diarrhea. While various so-called magnesium chelate compounds have been promoted as having better magnesium bioavailability, these compounds may be highly alkaline and poor in terms of palatability.

The recommended daily intake of magnesium for an adult is generally from about 15 mmol to 20 mmol (30 mEq to 40 mEq), and normal magnesium serum levels range from 0.7 mmol/L to 1.0 mmol/L. Foods that are rich in magnesium include legumes, whole grains, green leafy vegetables, nuts, coffee, chocolate and milk. Although these foods are readily available, some individuals do not consume adequate quantities to satisfy the daily nutritional requirement. Furthermore, expanded consumption of processed foods, which tend to contain less magnesium, may account for the perceptible decline in dietary magnesium in the United States during the past century. Thus, continued use of an oral magnesium supplement that offers reliable absorption and bioavailability is recommended for people with magnesium deficiency. Oral magnesium supplements are available in a number of formulations that utilize a different anion or salt—such as oxide, gluconate, chloride or lactate dihydrate. However, these preparations are not interchangeable because they have differences in absorption, bioavailability and palatability.

Magnesium is absorbed primarily in the distal small intestine, and healthy people absorb approximately 30% to 40% of ingested magnesium. Since magnesium is predominately an intracellular cation, the effectiveness of a dosage form is assessed by its solubility and rate of uptake from the small intestine into the bloodstream ands by its transfer into the tissues. Magnesium balance is regulated by the kidneys. When magnesium levels in the blood are high, the kidneys will rapidly excrete the surplus. When magnesium intake is low, on the other hand, renal excretion drops to 0.5 mmol to 1 mmol (1 mEq to 2 mEq) per day.

Means for providing magnesium to the human body as a supplement have been proposed in the art. For example, for the treatment of arrhythmia, magnesium sulfate has been intravenously administered to patients. Other dietary supplements have included magnesium oxide, magnesium hydroxide and magnesium carbonate. Despite the ability of these compounds to increase magnesium levels, they are primarily insoluble in the gastrointestinal tract, and hence, not easily delivered to the gastrointestinal system, without side-effects. As such, there is a considerable need for improved magnesium compositions, uses thereof, and/or associated technology. The subject invention satisfies these needs and provides related advantages as well.

SUMMARY OF THE INVENTION

A composition for administration to a subject is described herein. Such a composition may comprise at least one magnesium-comprising component (MCC) or also used herein as magnesium-counter ion compound. Examples of an MCC include a magnesium salt of an amino acid, magnesium acetate, magnesium ascorbate, magnesium citrate, magnesium gluconate, magnesium lactate, magnesium malate, magnesium pyrrolidone carboxylate, magnesium taurate, and magnesium threonate. Such a composition may comprise at least one component of non-acidified milk sufficient to enhance bioavailability of elemental magnesium associated with the MCC. Examples of such a component include lactose, a fatty acid or milk fat, and/or another organic component thereof, for example, sufficient for such enhancement. A mass ratio of the amount of elemental magnesium associated with the at least one MCC and the amount of the component may be from about 1 to about 5 to about 1 to about 3000. Such a composition may be suitable for oral administration to a subject.

In one embodiment, the present invention provides an oral dosage form comprising 300 mg to 1.5 g of magnesium threonate. The oral dosage form can be a tablet, formulated in form of liquid, in immediate or sustained release format. In some aspects, the oral dosage form comprises a plurality of beads encapsulated in a capsule. Such format can be used as a sustained release formulation.

In another embodiment, the present invention provides a magnesium-containing composition that has the following characteristics: (a) the magnesium contained therein has a weight percentage of at least about 8%; (b) a counter ion comprises at least two hydroxyl groups; (c) the composition has a solubility of at least at least 20 mg/mL; and (d) the composition exhibit a pH value between about 6 to 8.5 when dissolved in water.

The present invention also provides a magnesium-containing an oral dosage that comprises a pharmaceutically active agent and an excipient, wherein the excipient is magnesium thereonate Further provided in the present invention is a food composition comprising a food carrier and a magnesium-containing compound where the magnesium-containing compound is characterized in that: a) the carbon contained therein has a weight percentage of at least about 8% of the weight of a counter ion; b) a counter ion comprises at least two hydroxyl groups; c) the composition has a solubility of at least about 20 mg/mL; and d) the composition exhibits a pH value between about 6-8.5 when dissolved in water. In some embodiments, the magnesium containing compound comprises magnesium threonate. In other embodiments, the food composition is packaged as a beverage, a solid food or a semi-solid food. In still other embodiments the food composition is packaged as a snack bar, a cereal product, a bakery product or a dairy product. The food composition may be milk or a soft drink. In some embodiments, the food composition comprises: an effective amount of magnesium or salt thereof for modulating cognitive function in a subject in need thereof; and a food carrier. Where desired, the food composition comprises magnesium threonate. In some embodiments, the food composition contains magnesium or a salt thereof present in an amount effective to enhance short-term memory or long-term memory, ameliorate dementia or ameliorate depression. Also provided is a food supplement comprising magnesium threonate. Also provided is a method of preparing a food supplement comprising mixing magnesium threonate with a food additive agent. In some embodiments, the food additive agent is a sweetening agent, a flavoring agent, a coloring agent, a filling agent, a binding agent, a lubricating agent or a preservative agent.

A composition, kit, and/or a method described herein may be useful for purposes described herein, such as maintaining, enhancing, and/or improving health, nutrition, and/or another condition of a subject, and/or cognitive, learning, and/or memory function, for example, such as magnesium deficiency, mild cognitive impairment (MCI), Alzheimer's disease (AD), attention deficit hyperactivity disorder (ADHD), amyotrophic lateral sclerosis (ALS) or Lou Gehrig's disease, Parkinson's disease, diabetes, migraine, anxiety, mood, and hypertension, merely by way of example.

A method of providing magnesium supplementation to a subject is described herein. Such a method may comprise administering to the subject at least one MCC, such as any of those described above. Such a method may comprise administering to the subject at least one component of non-acidified milk sufficient to enhance bioavailability of elemental magnesium associated with the MCC, such as any of those described above. A mass ratio of the amount of elemental magnesium associated with the at least one MCC and the amount of the component maybe as described above. Such a method may comprise oral administration to the subject.

In one embodiment, the present invention provides a method of enhancing cognitive function. The method comprises administering to a subject an amount of magnesium-containing compound effective to achieve a physiological concentration of magnesium at about 0.75 mM or above, wherein said concentration of magnesium is measured under a fasting condition. In some instances, the concentration of magnesium is measured after fasting for at least about twelve hours. In other instances, the physiological concentration is serum concentration, plasma concentration, or cerebrospinal fluid concentration. In some embodiments, the magnesium-containing compound is a magnesium-counter ion compound. In other embodiments, the counter ion is an organic ion. In other instances the organic counter ion is threonate. In some embodiments, the magnesium-containing compound is a magnesium-supplemented foodstuff. Also provided is a method where the cognitive function is short-term memory or long-term memory. In some instances, the physiological concentration is maintained for a period of greater than one month.

In one embodiment, a method of maintaining cognitive function is provided wherein the method comprises administering to a subject an amount of magnesium-containing compound effective to increase a physiological concentration of magnesium by at least about 10% as compared to an initial level of magnesium prior to the administration. In some instances the increase is measured under a fasting condition. In other instances, the physiological concentration is serum concentration, plasma concentration, or cerebrospinal fluid concentration. In some embodiments the magnesium-containing compound is a magnesium-counter ion compound. In other embodiments the counter ion is an organic counter ion. In a particular embodiment the organic counter ion is threonate. In some embodiments, the magnesium-containing compound is a magnesium-supplemented foodstuff. In still further embodiments, the concentration is maintained for a period of greater than four months. In yet another embodiment, the method comprises the step of determining starting physiological magnesium concentration of the subject under a fasting condition.

Also provided is a method of maintaining and/or enhancing cognitive function comprising administering to a subject an amount of metal-organic counter ion complex effective to increase a physiological concentration of threonate by at least about 10% as compared to an initial level of threonate prior to said administration. In some instances the metal-organic counter ion complex comprises threonate as a counter ion.

In another aspect of the invention, a method for therapeutic or prophylactic treatment of a cognitive dysfunction is provided, wherein the method comprises administering to a subject in need of therapeutic or prophylactic treatment of cognitive dysfunction a magnesium-containing composition to yield a level of physiological concentration of magnesium sustained at the level of 0.75 mM or above for at least about 15 days. In some instances, the magnesium is sustained at the level of 0.75 mM or above for at least about one month or at least about four months. In other instances, magnesium concentration is magnesium plasma concentration measured after fasting for at least about eight hours. In some embodiments, the subject is an adult. In other embodiments, the subject is a patient suffering from or diagnosed with dementia or Alzheimer's disease.

Where desired, one can administer to a subject an amount of magnesium-containing compound effective to achieve a physiological concentration of magnesium at about 0.78 mM, 0.8 mM, 0.82 mM, 0.84 mM, 0.86 mM, 0.88 mM, 0.90 mM, 0.92 mM, 0.94 mM, 0.96 mM, 0.98 mM, or above. In one aspect, such magnesium concentration is maintained for at least 1 month, 2 months, 3 months, 4 months, 5 months, 6 months, 1 year, 1.5 years, 2 years, or even longer. Preferably, the concentration of magnesium is measured under a fasting condition, e.g., after fasting for at least about 8 hours, 10 hours, 12 hours, 15 hours, 24 hours, or even longer. The physiological concentration of magnesium can be serum concentration, plasma concentration, or cerebrospinal fluid concentration. Such physiological concentration can be determined by measuring intracellular ionized magnesium in red blood cells, bone magnesium content, magnesium concentration in the cerebrospinal fluid, a sublingual magnesium assay intracellular free magnesium, or nuclear magnetic resonance spectroscopy. In some aspect, the magnesium-containing compound is effective in improving short-term or long-term memory.

In a related embodiment, the present invention provides a method of therapeutic or prophylactic treatment, of cognitive dysfunction, comprising: administering to a subject in need for a therapeutic or prophylactic treatment of cognitive dysfunction a composition of magnesium that yields a sustained level physiological concentration of magnesium of 0.75 mM or above for at least about 15 days, e.g. upon, multiple dosages. Preferably, the beneficial effect can last longer than 20 days, 25 days, 1 month, 2 months, 3 months, 4 months, 5 months, 6 months, 1 year, 1.5 years, 2 years or longer.

In another embodiment, the present invention provides a method of ameliorating the effects of a neurological disorder. The method comprises administering to a subject an amount of magnesium-containing compound effective to increase a physiological concentration of magnesium by at least about 10% as compared to an initial level of magnesium prior to the administration. In some instances, the increase is measured under a fasting condition. In other instances the concentration of magnesium is measured after fasting for at least about twelve hours. In some embodiments of this method, the neurological disorder is dementia, Alzheimer's disease or depression. In other embodiments of the method, the physiological concentration is serum concentration, plasma concentration or cerebrospinal fluid concentration. In some embodiments of this method, the magnesium-containing compound is a magnesium-counter ion compound. Where desired, the counter ion is an organic ion. In a particular embodiment, the organic counter ion is threonate. In some instances, the magnesium-containing compound is a magnesium-supplemented foodstuff. In some instances of this method, the concentration is maintained for a period of greater than four months. In other embodiments, the method further comprises the step of determining starting physiological magnesium concentration of the subject under a fasting condition.

Yet another aspect of the present invention provides a method of therapeutic or prophylactic treatment Of a neurological disorder, comprising administering to a subject in need of therapeutic or prophylactic treatment of said neurological disorder, a magnesium-containing composition to yield a sustained level of physiological concentration of magnesium of 0.75 mM or above for at least about 15 days. In some embodiments, the composition of magnesium yields a sustained level of physiological concentration of magnesium of 0.75 mM or above for at least about one month or at least about four months. In some instances, the neurological disorder is dementia, depression or Alzheimer's disease.

In still another embodiment, a method of therapeutic or prophylactic treatment of a neurological disorder is provided where the method comprises administering to a subject an amount of metal-organic counter ion complex effective to increase a physiological concentration of threonate by at least about 10% as compared to an initial level of threonate prior to said administration. In some instances, the metal-organic counter ion complex comprises threonate as a counter ion.

Also provided is a method of ameliorating the effects of a metabolic disorder comprising administering to a subject an amount of magnesium-containing compound effective to increase a physiological concentration of magnesium by at least about 10% as compared to an initial level of magnesium prior to said administration. In some instances the concentration of magnesium is measured after fasting for at least about twelve hours. In other instances, the physiological concentration is serum concentration, plasma concentration, or cerebrospinal fluid concentration. In some embodiments of this method the magnesium-containing compound is a magnesium-counter ion compound. In other embodiments, the counter ion is an organic ion. In a particular embodiment, the organic counter ion is threonate. In some embodiments, the magnesium-containing compound is a magnesium-supplemented foodstuff. In some embodiments, the metabolic disorder is diabetes. In other embodiments, the concentration is maintained for a period of greater than 1 month.

In still another aspect of the present invention a method of therapeutic or prophylactic treatment of a metabolic disorder is provided, wherein the method comprises administering to a subject in need of therapeutic or prophylactic treatment of a metabolic disorder a magnesium-containing composition to yield a level of physiological concentration of magnesium sustained at the level of 0.75 mM or above for at least about 15 days. In some instances, the magnesium is sustained at the level of 0.75 mM or above for at least about 1 month or at least about four months. In other instances, magnesium concentration is magnesium plasma concentration measured after fasting for at least about 8 hours. In some embodiments, the subject is an adult.

In yet another aspect of the present invention, a method of therapeutic or prophylactic treatment of a metabolic disorder is provided comprising administering to a subject an amount of metal-organic counter ion complex effective to increase a physiological concentration of threonate by at least about 10% as compared to an initial level of threonate prior to said administration. In some embodiments the metal-organic counter ion complex comprises threonate as a counter-ion. In other embodiments, the metal-organic counter ion complex is magnesium threonate. In still other embodiments, the metal-organic counter ion complex is administered orally. In still other embodiments, the metal-organic counter ion complex is provided as a food supplement.

Another embodiment provides a method of extending lifespan of a subject comprising administering to said subject an amount of magnesium-containing compound effective to achieve a physiological concentration of magnesium of about 0.75 mM or above, thereby extending the lifespan of said subject, wherein said concentration is measured under a fasting condition. In some embodiments, the concentration of magnesium is measured after fasting for at least about twelve hours. In other embodiments, the physiological concentration is serum concentration, plasma concentration, or cerebrospinal fluid concentration. In some embodiments, the magnesium-containing compound is a magnesium-counter ion compound. In other embodiments, the counter ion is an organic counter ion. In a particular embodiment, the organic counter ion is threonate. In some embodiments, the said magnesium-containing compound is a magnesium-supplemented foodstuff. In some embodiments, the concentration is maintained for a period of greater than 1 month.

Another embodiment provides a method of extending lifespan of a subject comprising administering to a subject an amount of magnesium-containing compound effective to increase a physiological concentration of magnesium by at least about 10% as compared to an initial level of magnesium prior to said administration. In some embodiments, the increase is measured under a fasting condition. In some embodiments, the physiological concentration is serum concentration, plasma concentration, or cerebrospinal fluid concentration. In some embodiments, the magnesium-containing compound is a magnesium-counter ion compound. In some embodiments, the counter ion is an organic counter ion. In some embodiments, the organic counter ion is threonate. In some embodiments, the magnesium-containing compound is a magnesium-supplemented foodstuff. In some embodiments, the concentration is maintained for a period of greater than 4 months. In some embodiments, the method further comprises the step of determining starting physiological magnesium concentration of said subject under a fasting condition.

Still another embodiment of the present invention provides a method of extending lifespan of a subject comprising administering to a subject an amount of metal-organic counter ion complex effective to increase a physiological concentration of threonate by at least about 10% as compared to an initial level of threonate prior to said administration. In some embodiments, the metal-organic counter ion complex comprises threonate as a counter-ion.

Also provided is a method of determining an effective amount of magnesium to produce a physiological effect, comprising the steps of: a) obtaining a sample from a subject being tested, wherein said sample is taken under a fasting condition; b) determining a physiological concentration of magnesium from said sample; and c) providing the subject with a magnesium-containing compound dosing regimen effective to achieve a physiological concentration of magnesium of about 0.75 mM or above. In some embodiments, the concentration of magnesium is measured after fasting for at least about twelve hours. In other embodiments, the physiological concentration is serum concentration, plasma concentration, or cerebrospinal fluid concentration. In some embodiments, the magnesium-containing compound is a magnesium-counter ion compound. In still other embodiments, the counter ion is an organic counter ion. In a particular embodiment, the organic counter ion is threonate. In some embodiments, the magnesium-containing compound is a magnesium-supplemented foodstuff. In another embodiment, the method further comprises the step of determining a physiological concentration of magnesium after said subject has begun said dosing regimen.

Another embodiment of the present invention provides a method of determining an effective amount of magnesium to produce a physiological effect, comprising the steps of: a) obtaining a sample from a subject being tested, wherein said sample is taken under a fasting condition; b) determining a physiological concentration of magnesium from said sample; and c) providing said subject with a magnesium-containing compound dosing regimen effective to achieve an increase in a physiological concentration of magnesium by at least about 10% as compared to an initial level of magnesium measured under a fasting condition.

Where desired, the amount of magnesium-containing compound is effective to increase a physiological concentration of magnesium by at least about 12%, 14%, 15%, 20%, 25% or more as compared to an initial level Of magnesium prior to said administration. The increase in physiological concentration of magnesium can last for at least 1 month, 2 months, 3 months, 4 months, 5 months, 6 months, 1 year, 1.5 years, 2 years, or even longer. As noted herein, the increase in physiological concentration of magnesium is preferably measured after a fasting condition. The neurological disorders that can be ameliorated by the subject method include but are not limited to dementia, Alzheimer's disease, and depression. In a related but separate embodiment, the present invention provides a method of ameliorating depression by administering to a subject in need for a therapeutic or prophylactic treatment of depression, a composition of magnesium to yield a sustained level of physiological concentration of magnesium of 0.75 mM or above for at least about 15 days, e.g., upon multiple dosages. Preferably, the beneficial effect can last longer than 20 days, 25 days, 1 month, 2 months, 3 months, 4 months, 5 months, 6 months, 1 year, 1.5 years, 2 years or longer.

In yet another embodiment, the present invention provides a method of increasing bone density. The method comprises the step of administering to a subject in need for a therapeutic or prophylactic treatment of bone density a composition of magnesium to be sustained at the level of 0.75 mM or above for at least about 15 days, 20 days, 25 days, 1 month, 2 months, 3 months, 4 months, 5 months, 6 months, 1 year, 1.5 years, 2 years or longer.

In still another embodiment, the present invention provides a method of extending lifespan of a subject comprising administering to said subject an amount of magnesium-containing compound effective to achieve a physiological concentration of magnesium of about 0.75 mM or above, thereby extending the lifespan of said subject, wherein said concentration is measured under a fasting condition. Also provided in a related embodiment is a method of increasing expected life span of a subject, comprising: administering to a subject a composition of magnesium to yield a sustained level of physiological concentration of magnesium of 0.75 mM or above for at least about 15 days, 20 days, 25 days, 1 month, 2 months, 3 months, 4 months, 5 months, 6 months, 1 year, 1.5 years, 2 years or longer.

The present invention also provides a method of determining an effective amount of magnesium to produce a physiological effect. The method comprises the steps of (a) obtaining a sample from a subject being tested, wherein said sample is taken under a fasting condition; (b) determining a physiological concentration of magnesium from said sample; and (c) providing said subject with a magnesium-containing compound dosing regimen effective to achieve a physiological concentration of magnesium of about 0.75 mM or above. In a related but separate embodiment, the method of determining an effective amount of magnesium to produce a physiological effect comprises the steps of (a) obtaining a sample from a subject being tested, wherein said sample is taken under a fasting condition; (b) determining a physiological concentration of magnesium from said sample; and (c) providing said subject with a magnesium-containing compound dosing regimen effective to achieve an increase in a physiological concentration of magnesium by at least about 10% as compared to an initial level of magnesium measured under a fasting condition. The physiological effect encompasses enhanced cognitive function (e.g., short-term memory or long-term memory), ameliorating an effect of a neurological disorder such as Alzheimer's disease or depression.

These and various other aspects, features, and embodiments are further described herein. Any other portion of this application is incorporated by reference in this summary to the extent same may facilitate a summary of subject matter described herein, such as subject matter appearing in any claim or claims that may be associated with this application.

In a related but separate embodiment, the present invention provides an oral dosage form comprising about 0.1 mg to 800 mg of magnesium threonate. Where desired the oral dosage form comprises between about 1 mg to about 100 mg, 10 mg to about 500 mg, or more magnesium threonate. In some embodiment, the oral dosage form is substantially free of excipient. The oral dosage form can be in form of a tablet, capsule, or any other known format. The present invention also provides food supplements comprising the subject MCC or magnesium-counter ion compound.

Also provided is a method of determining an amount of magnesium-containing component that is needed to produce a physiological effect in a subject, comprising the steps of:
a. obtaining a sample of biological fluid from the subject; and
b. calculating the amount of magnesium to be supplied to said subject according to the formula of:

$$Mg = GFR \cdot T \cdot Mg_{mw} \cdot k_e \cdot ([Mg]_o^2 - [Mg]_o^1)/k_x$$

wherein $Mg_x$ is effective amount of magnesium to be supplied to said subject;
wherein $[Mg]_o^1$ is the initial concentration of magnesium in extracellular compartment;
wherein $K_x$ is bioavailability of said magnesium-containing component;
wherein GFR is glomerular filtration rate;
wherein $k_e$ is the excretion rate of filtered Mg in kidney;
wherein T is time in hours;
wherein $Mg_{mw}$ is molecular weight of the element magnesium; and
wherein $[Mg]_o^2$ is a desired concentration of magnesium to be achieved upon
supplementing said subject the determined amount of magnesium-containing component.

In some embodiments, the concentration of magnesium in said biological fluid is measured under a fasting condition. In some embodiments, the concentration of magnesium is measured after fasting for at least about twelve hours. In some embodiments, the biological fluid is selected from blood, serum and, plasma. In some embodiments, the amount of magnesium supplied is effective to achieve an increase in a physiological concentration of magnesium by at least about 5% as compared to an initial level of magnesium measured under a fasting condition.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

A description of various aspects, features, embodiments, and examples is provided herein with reference to the accompanying drawings, which are briefly described below. The drawings may illustrate one or more aspect(s), feature(s), embodiment(s), and/or example(s) in whole or in part. The drawings are illustrative and are not necessarily drawn to scale.

DETAILED DESCRIPTION OF THE INVENTION

Figure 1:
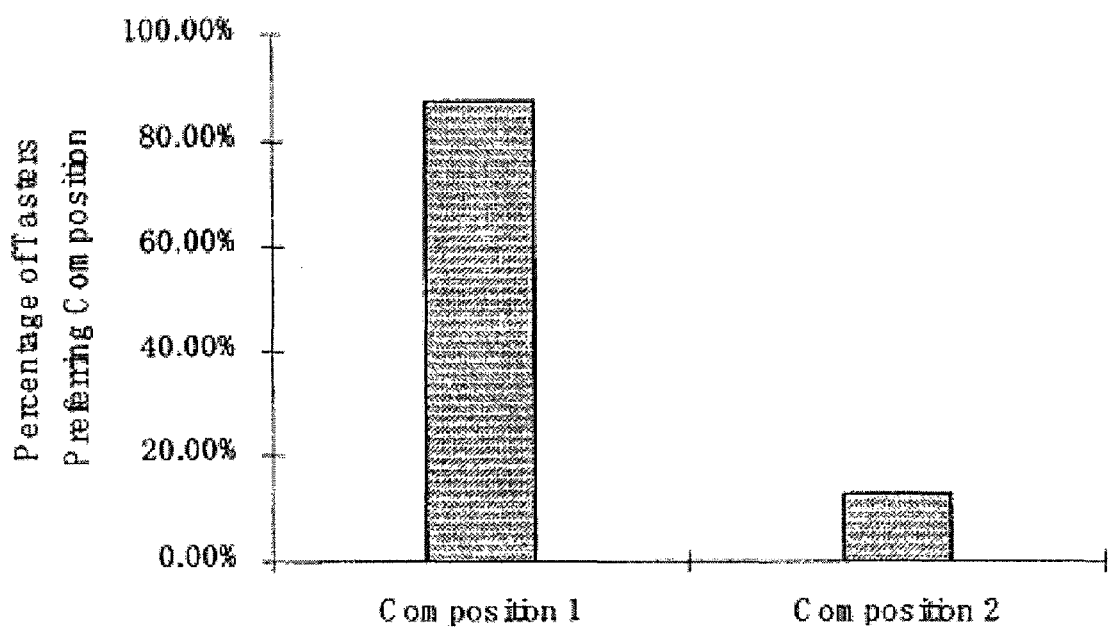
FIG. 1 is a graphical presentation of results of a taste test concerning two different compositions comprising milk and various sources of magnesium, as further described in Example 2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

It will be understood that a word appearing herein in the singular encompasses its plural counterpart, and, a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Generally, the term "approximately" or "about" or the symbol "~" in reference to a figure or number or amount includes numbers that fall within a range of ±5% of same, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising"-, "consisting essentially of"-, and/or "consisting of"-type language.

A magnesium-counter ion composition, a kit, and/or a method described herein may be useful for purposes described herein, such as maintaining, enhancing, and/or improving health, nutrition, and/or another condition of a subject, and/or cognitive, learning, and/or memory function, for example, such as magnesium deficiency, mild cognitive impairment (MCI), Alzheimer's disease (AD), attention deficit hyperactivity disorder (ADHD), ALS, Parkinson's disease, diabetes, migraine, anxiety, mood, and hypertension, merely by way of example. A description of various aspects, features, embodiments, and examples, is provided herein.

Figure 17:
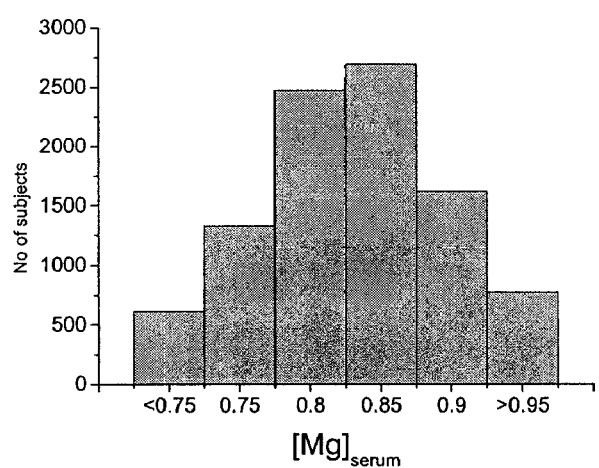
FIG. 17 is a graphical representation of serum concentration levels of magnesium in men and women.
Figure 18:
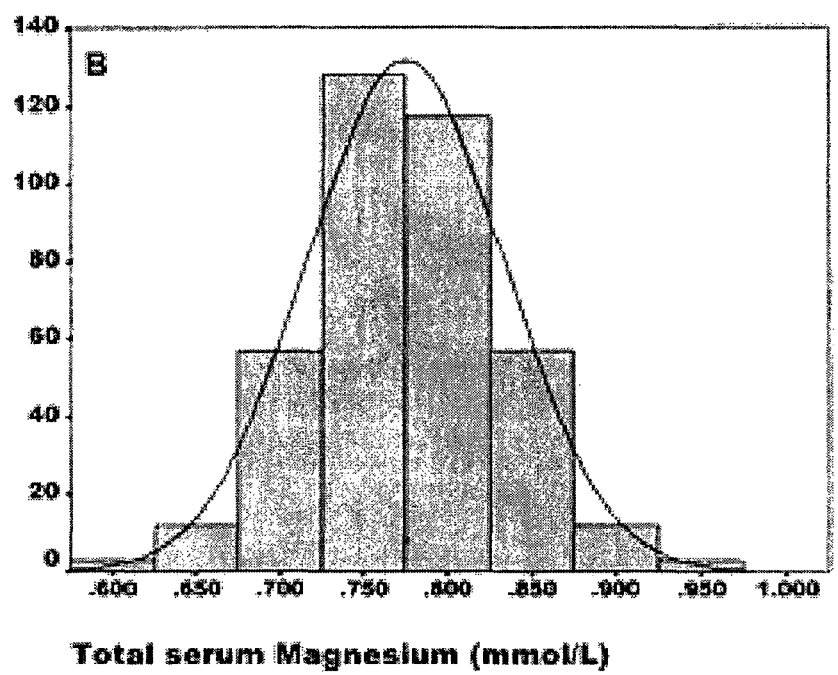
FIG. 18 is a graphical representation of serum concentration levels of magnesium in women between the ages of 18 and 35.

The body magnesium level among human population varies from person to person, approximately distributed according to a Gausian curve. For example, in a survey among 9506 white males and females the serum Mg levels were distributed between about 0.75 mM and about 0.95 mM with most subjects having a serum magnesium level near the middle of the distribution. The distribution in men and women is shown in FIG. 17 (adopted from Kao et al., *Arch. Intern. Med.* 159: 2151-9 (1999); FIG. 18). The distribution in serum magnesium levels among young and healthy women has also been reported and show a similar distribution pattern, as shown in FIG. 18 (adopted from Cole and Quamme, *J. Amer. Soc. Nephrol.* 11: 1937-47 (2000)). However, other studies have shown that blood (serum or plasma) magnesium levels in AD patients are approximately 20% lower than healthy control groups. See, e.g., Lemke, *Biol. Psychiatry.* 37: 341-3 (1995); Cilliler et al. *Gerontology.* 53: 419-22 (2007).

A number of methods have been used to assess the body magnesium levels in humans. These methods differ from one another in the type of sample and the analytical technique used. Serum and plasma have been the two most commonly used types of samples although some studies used red blood cells or tissue samples. Among the Mg detection techniques used are: absorbance-based dye technique, atomic absorption technique, ion-selective electrode technique and NMR technique. The first two techniques measure the total magnesium concentration, which include both ionized free $Mg^{2+}$ and $Mg^{2+}$ bound to proteins and other molecules in the sample, while the latter two techniques measure only ionized magnesium.

A major problem with the various methods mentioned above is the lack of a standardized test, including a standardized condition under which a test is performed. There is also poor understanding about the interrelation between the experimental values obtained from the various methods. For this reason, the range of blood magnesium (serum or plasma) levels reported for healthy subjects or patients vary widely from study to study and from lab to lab. For example, Cilliler, et al. reported that the average serum Mg levels for AD patients diagnosed as mild and moderate, AD patients diagnosed as severe, and non-AD control subjects were 0.92 mM (2.197 mg/dl), 0.88 mM (2.11 mg/dl) and 1.05 mM (2.51 mg/dl), respectively. Although the trend for blood magnesium level between AD patients and their healthy control subjects is consistent with earlier findings, the absolute values of the serum magnesium levels determined by these authors are significantly higher than those reported elsewhere. For example, the 0.92 and 0.88 mM serum magnesium concentrations reported by Cilliler, et al. are even higher than the means of serum magnesium concentration for healthy people shown in FIGS. 17 and 18. In another study by Garba, et al. the average serum Mg level among 20 healthy subjects aged from 18 to 40 was only 0.27 mM (640 □g/dl).

Further contributing to the confusion is the lack of a guideline on the timing of sampling. In some studies, subjects were subject to overnight fasting before blood samples were taken while in some other studies this sampling protocol was not clearly followed. Part of the confusion may be related to the fact that most clinical guidelines for blood magnesium test do not require any preparation (such as fasting) for the test (see, e.g., http://health.nytimes.com/health/guides/test/serum-magnesium-test/overview.html; http://www.med.umich.edu/llibr/aha/aha_smagnesi_crs.htm; and http://www.privatemdlabs.com/lp/magnesium_info.php). Thus, non-standardized sampling procedures may be a major contributing factor accounting for the wide variations of human blood magnesium levels reported in the literature. One aspect of the present invention provides a method for standardizing determination of physiological concentrations of magnesium. Another aspect of the present invention is utilizing such determinations to provide guidelines for magnesium supplementation to enhance beneficial effects of magnesium.

In one embodiment, the present invention provides a range of physiologically useful concentrations of magnesium to effect a desired physiological effect. In some embodiments, these concentrations are "high end" concentrations. Such "high end" concentrations include serum magnesium concentration from about 0.60 mM, 0.65 mM, 0.70 mM, 0.75 mM, 0.80 mM. 0.85 mM, 0.95 mM, 1.0 mM, 1.05 mM, 1.10 mM, 1.15 mM to 1.2 mM or even higher, plasma magnesium concentration from about 0.70 mM, 0.75 mM, 0.80 mM. 0.85 mM, 0.95 mM, 1.0 mM, to 1.05 mM or even higher, and/or blood ionized magnesium concentration from about 0.50 mM, 0.55 mM, 0.60 mM, 0.65 mM, to about 0.70 mM. In some other embodiments, the subject magnesium-containing compound is effective to increase a physiological concentration of magnesium by at least about 10%, 11%, 12%, 13%, 14%, 15%, 20%, 25% or even higher as compared to an initial level of magnesium prior to administration of it to a subject. Where desired, suitable concentrations for eliciting the effects of magnesium supplementation as described herein can be from about 0.8, 0.9, 1.0, 1.1, 1.2, 1.3, 1.4, 1.5, 1.6, times the median value reported. Where desired, the selected physiological concentration of magnesium is measured under a fasting condition, Without taking food for at least about 8 hours, 10 hours, 12 hours, 15 hours, 24 hours, or even longer.

Additionally, magnesium compounds may be delivered to the brain of a subject via a pump or any other suitable injection device. Such devices are known in the art and may deliver compounds directly to the brain or indirectly to the brain via the spinal cord. Administration using such devices, for example perispinal etanercept administration, has been described previously. See, Tobinick and Gross *J. Neuroinflammation* 5:2). This example is given only for illustration purposes and is not intended to be limiting on the present invention. The amount of magnesium delivered to the brain may be such that the magnesium concentration in the CSF, $[Mg]_{CSF}$, is increased by at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% or more. Where desired, $[Mg]_{CSF}$ can increase to about 0.60, 0.65, 0.70, 0.75, 0.80. 0.85, 0.95, 1.0, 1.05, 1.10, 1.15, 1.20, 1.25, 1.30, 1.35, 1.40, 1.45, or 1.5 mM. Preferably, cerebrospinal fluid concentration ($[Mg]_{CSF}$) is increased by at least 10%, 11%, 12%, 13%, 14%, 15%, 20%, 25% or more. Where desired, $[Mg]_{CSF}$ can be increased to about 1.2 mM. The pump or injection device may be any known in the art for delivering a therapeutic agent to the brain.

Magnesium is an essential mineral in the human body because of its roles in numerous physiological functions. Yet, it is generally recognized that at least half of the people in the industrialized world do not get sufficient magnesium from their diets. Several diseases, such as diabetes and Alzheimer's disease, are associated With magnesium deficit. Therefore, there is a need for magnesium supplementation. The recommended daily allowance (RDA) for magnesium is 400 mg for adults. By assuming that people get 40-50% of the required magnesium from diet, the recommended amount of magnesium supplement has generally been about 200-250 mg per day for adults. There are numerous magnesium compounds that have been used as magnesium supplements. These compounds include magnesium oxide, magnesium citrate, magnesium sulfate, magnesium chloride, magnesium gluconate, magnesium lactate, magnesium pidolate and magnesium diglycinate, for example. At least for nutritional purpose, the recommended amount of magnesium supplementation for most commercial magnesium supplements is about the same (i.e., about 250 mg magnesium per day), regardless of the bioavailability of the magnesium compound and the individual's kidney function to retain the amount of the absorbed magnesium. Some magnesium supplement suppliers have recommended higher daily magnesium intake for their products, again, without considering an individual's kidney function for magnesium retention. Similar to magnesium deficit, an excessive amount of magnesium in the body (hypermagnesemia) may also lead to health problems, such as neuromuscular depression, hypotension, cardiac arrythmias and respiratory paralysis. Thus, it is important to have one's blood magnesium level stay within the normal range. Disclosed herein is a novel method for controlling the magnesium level to a particular region of the normal range. In some aspects of the invention, this method also offers particular health advantages, such as increased memory capabilities, increased lifespan, decreased depression, and decreased symptoms of neurological disorders, including AD.

In addition to nutritional use, magnesium supplements have been used for treating type 2 diabetes. In one study, diabetic patients were treated with nearly 1 g of magnesium daily using magnesium oxide for 1 month (de Lordes Lima, et al., *Diabetes Care.* 21: 682-6 (1998)). The treatment increased the serum magnesium level of the patients by about 10% but with only minor improvement in metabolic control. In another study, diabetic patients were treated with 720 mg/day of magnesium for three months. Similarly, the blood magnesium levels of the patients were raised by about 10% on average (Eibl, et al., *Diabetes Care.* 21: 2031-2 (1995)). However, the metabolic control of the patients, as assessed by their HbAlc levels, had no improvement.

Magnesium ion has been reported to be generally useful for treatment of dementia (e.g., U.S. Pat. No. 4,985,256). Landfield and Morgan showed that young (9-month old) and aged (25-month old) rats fed food containing 2% magnesium oxide for 8 days had shown some sign of improvement of cognitive function (Landfield and Morgan, *Brain Research,* 322:167-171 (1984)). However, the gain in cognitive function was transient and at the cost of diarrhea and weight loss to the animals. In fact, the side-effect was so severe the researchers had to use an alternating feeding schedule by having the animals on the high Mg diet for 4 days, followed by a regular diet for two days and then back to the high Mg diet for another 4 days.

Magnesium compounds may also be used to affect bone density. Bone density disorders, including but not limited to osteoporosis, may be treated by supplementation with magnesium compounds of the present invention. Subjects may be treated to ameliorate the effects of low bone density or as prophylaxis against lost bone density. Bone density may be measured by any means known in the art, including, but not limited to, dual energy X-ray absorptiometry (DEXA), ultrasound, quantitative computed tomography, single energy absorptiometry, magnetic resonance imaging, measuring metacarpal width, and hand X-ray analysis.

As mentioned above, a magnesium-counter ion composition and/or a method described herein are useful for various purposes, such as maintaining, enhancing, and/or improving health, nutrition, and/or another condition of a subject, and/or cognitive, learning, and/or memory function, for example. Examples of such a condition of a subject include magnesium deficiency, mild cognitive impairment, Alzheimer's disease, Huntingdon's disease, autism, schizophrenia, cognitive decline as secondary effect of disease or medical treatment (HIV disease, cancer, chemotherapy), depression, dementia, attention deficit hyperactivity disorder, ALS, Parkinson's disease, diabetes, cardiovascular disease (e.g., hypertension), glaucoma, migraine, anxiety, mood, and hypertension, merely by way of example. Magnesium supplementation may also be useful in maintaining, enhancing, and/or improving conditions which may result in loss of body magnesium, including, but not limited to, alcoholism, anorexia, bulemia, metabolic syndromes, and poor nutrition. Any such condition may be deemed or defined as a physiological, psychiatric, psychological, or medical condition or disorder, for example. Generally, the term "subject" may refer to any animal. Examples of such animals include, but are not limited to, cold-blooded animals, warm-blooded animals, mammals, domesticated mammals, primates, humans, and individuals or a patient to whom a composition is to be administered for experimental, diagnostic, nutritional, and/or therapeutic purposes. A subject or patient may be a subject or patient of normal, good, or excellent health, mood, cognitive, and/or nutritional status, or of compromised health, mood, cognitive, and/or nutritional status, including of abnormal, poor, damaged, unhealthy, impaired, diseased, and/or nutritionally deficient status. The subject may be of any age, including advanced age.

Generally, the term "cognition" may refer to a process of obtaining, organizing, understanding, processing, and/or using information or knowledge. Generally, enhancing cognitive function refers to enhancing any aspect of such a process, such as learning, the performance of mental operations, the storage, retrieval, and/or use of information and/or thoughts, memory, and/or preventing a decline of a subject's cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

Generally, the term "concurrent administration" in reference to two or more subjects of administration for administration to a subject body, such as components, agents, substances, materials, compositions, and/or the like, refers to administration performed using dose(s) and time interval(s) such that the subjects of administration are present together within the subject body, or at a site of action in the subject body, over a time interval in less than de minimus quantities. The time interval may be any suitable time interval, such as an appropriate interval of minutes, hours, days, or weeks, for example. The subjects of administration may be administered together, such as parts of a single composition, for example, or otherwise. The subjects of administration may be administered substantially simultaneously (such as within less than or equal to about 5 minutes, about 3 minutes, or about 1 minute, of one another, for example) or within a short time of one another (such as within less than or equal to about 1 hour, 30 minutes, or 10 minutes, or within more than about 5 minutes up to about 1 hour, of one another, for example). The subjects of administration so administered may be considered to have been administered at substantially the same time. One of ordinary skill in the art will be able to determine appropriate dose(s) and time interval(s) for administration of subjects of administration to a subject body so that same will be present at more than de minimus levels within the subject body and/or at effective concentrations within the subject body. When the subjects of administration are concurrently administered to a subject body, any such subject of administration may be in an effective amount that is less than an effective amount that might be used were it administered alone. The term "effective amount," which is further described herein, encompasses both this lesser effective amount and the usual effective amount, and indeed, any amount that is effective to elicit a particular condition, effect, and/or response. As such, a dose of any such subject of concurrent administration may be less than that which might be used were it administered alone. One or more effect(s) of any such subject(s) of administration may be additive or synergistic. Any such subject(s) of administration may be administered more than one time.

Generally, the term "effective amount" in reference to an active agent refers to the amount of the active agent sufficient to elicit a particular biological condition, effect, and/or response. The absolute amount of a particular agent that is effective in this manner may vary depending on various factors, such as the desired biological endpoint, the agent itself, the subject or targeted part thereof, and/or the like, for example. An effective amount of an active agent may be administered in a single dose or in multiple doses. Examples of a biological condition, effect, or response that may result from an effective amount of an active agent include a maintaining and/or improving of a subject's performance of a task involving or associated with cognitive function, a maintaining and/or improving of a subject's performance in a test that measures something relating to or associated with cognitive function, a maintaining and/or improving (slowing, for example) of a rate of decline in cognitive function, and/or the like, for example. A component may be described herein as having at least an effective amount, or at least an amount effective, such as that associated with a particular goal or purpose, such as any described herein.

Generally, the term "elemental magnesium" as used in connection with a magnesium-counter ion compound described herein, may refer to a total amount of magnesium that is present as free ion and magnesium that is bound with one or more counter ions. In general, such a term is not used to refer to magnesium that may be associated with an agent other than a magnesium-counter ion compound that may be a component of a magnesium-counter ion composition (e.g., a pharmaceutical composition, a dietary supplement composition, a foodstuff supplemented with a magnesium-counter ion compound). A small amount of magnesium may be naturally present in or otherwise associated with such an agent. For example, a fruit juice extract or flavoring agent may comprise an amount of magnesium from that naturally present in the fruit from which it was derived. Generally, the term "elemental magnesium" as used in connection with an magnesium-counter ion compound would not encompass such agent-associated magnesium.

As used herein, the terms "magnesium comprising component" (MCC) and "magnesium-counter ion compound" are used interchangeably, and they are useful for purposes described herein, such as maintaining, enhancing, and/or improving health, nutrition, and/or another condition of a subject, such as magnesium deficiency, diabetes, mood, attention deficit hyperactivity disorder, ALS, Parkinson's disease, anxiety, depression and/or migraine, for example, and/or cognitive, learning, and/or memory function, such as MCI and/or AD, for example.

Such a composition, such as that appropriate for administration to a subject, may comprise at least one magnesium-comprising component (MCC). The MCC may be any suitable magnesium-comprising component, such as a suitably bioavailable magnesium-comprising component. The MCC may be any suitable biologically acceptable magnesium-comprising component. The MCC may be any suitable organic acid magnesium salt, such as a magnesium salt of a non-toxic C2-C12 carboxylic acid or a magnesium salt of a non-toxic C2-C12 sulfonic acid, for example. Merely by way of example, the MCC may be a magnesium salt of an amino acid, magnesium, acetate, magnesium ascorbate, magnesium citrate, magnesium gluconate, magnesium lactate, magnesium malate, magnesium pyrrolidone carboxylate (magnesium pidolate), magnesium taurate, and/or magnesium threonate. The at least one MCC may be present in at least an amount effective for maintenance, enhancement, and/or treatment of health, nutrition, and/or another condition of a subject, and/or cognitive, learning, and/or memory function, such as any of the conditions or functions described herein, for example.

In one embodiment, the composition of the invention may comprise at least one magnesium-counter ion compound. In other embodiments, the invention includes compositions comprising 2, 3, 4, 5, or more magnesium-counter ion compounds. In other embodiments, the counter ion(s) will be organic (e.g., threonate). In still other embodiments, the magnesium-counter ion compound has a solubility of range of solubility that distinguishes from Mg-gluconate/lactate/etc. In still other embodiments, the weight % of magnesium in a magnesium-counter ion compound is 6% or greater. In other embodiments, the weight % of magnesium in a magnesium-counter ion compound is 4%, 5%, 6%, 7%, 8% or greater. In some embodiments, the organic counter ion will have 1, 2, 3, 4, 5, 6, 7, 8, 9, 10 or more carbon atoms. In other embodiments, the magnesium-counter ion compound of the present invention is substantially free of laxative effect.

In one embodiment, the subject magnesium-containing composition is characterized in that: (a) the magnesium contained therein has a weight percentage of at least about 8%; (b) a counter ion comprises at least two hydroxyl groups; (c) the composition has a solubility of at least at least 20 mg/mL; and (d) the composition exhibit a pH value between about 6 to 8.5 when dissolved in water. An example of magnesium-containing composition having these characteristics is one comprising magnesium threonate.

The magnesium-counter ion compound may be any suitably bioavailable composition. The magnesium-counter ion compound may be any suitable biologically acceptable magnesium-counter ion compound. The at least one magnesium-counter ion compound may be present in at least an amount effective for maintenance, enhancement, and/or treatment of health, nutrition, and/or another condition of a subject, and/or cognitive, learning, and/or memory function, such as any of the conditions or functions described herein, for example.

A magnesium-counter ion composition may also contain a combination of magnesium-counter ion pairings. A magnesium-counter ion composition appropriate for administration to a subject may also comprise an agent for enhancing bioavailability of magnesium associated with a magnesium-counter ion compound, or a combination thereof, as further described herein. Examples of substances which may affect bioavailability include those which affect magnesium and/or counter-ion absorption, excretion, secretion, retention, and other physiologically relevant parameters. For example, a magnesium-counter ion composition can comprise vitamin D3 which can reduce magnesium excretion by the kidney (Ritchie et al., *Am. J Physiol. Renal Physiol.*, 280:868-78 (2001); Montgomery et al., *J. Anim. Sci.*, 82:2742 (2004)), and/or vitamin E which has been suggested to promote blood magnesium entering tissues (Barbagallo, et al., *Hypertension*, 34: 1002-6 (1999); Paolisso et al., *Clin. Endocrinol. Metab.*, 85:109-15 (2000)). One of skill in the art will recognize that these two vitamins are provided only as an example of the substances contemplated by the present invention and such substances are not limited to these two vitamins.

Bioavailability of a magnesium-counter ion compound may be evaluated or measured in any suitable way or using any suitable criterion. Generally, bioavailability of a magnesium-counter ion compound may be evaluated based on magnesium absorption rate and/or magnesium loading capacity. The magnesium absorption rate refers to the fraction of a subject's magnesium intake that is absorbed by the subject's body. In some cases, the magnesium absorption rate alone may not be sufficient to evaluate the bioavailability of a magnesium-counter ion compound. For example, for a given magnesium-counter ion compound, the magnesium absorption rate may stay relatively constant only when the magnesium-counter ion composition is administered at a relatively low dosage.

Further by way of example, for a given intake of a given magnesium-counter ion compound, there may be an upper limit on the amount of magnesium that can be absorbed from the magnesium-counter ion composition by the subject's body within a certain period, such as a 24-hour period. In such a case, as the magnesium-counter ion composition dosage increases to a certain level, the magnesium absorption rate associated with the magnesium-counter ion composition may decline, possibly significantly. Thus, for a given magnesium-counter ion composition, the magnesium absorption rate may be suitable when the magnesium-counter ion composition is administered at a relatively low dosage, but may be lower, less suitable, and/or unsuitable at a relatively high dosage.

An upper limit of the sort just described may be referred to as a magnesium loading capacity, which may be used to evaluate the bioavailability of a magnesium-counter ion compound. When a magnesium-counter ion compound that is associated with a relatively low magnesium loading capacity is administered to a subject at a relatively high dosage in one case as compared to a relatively low dosage in another case, the magnesium absorption rate in the one case may be relatively poorer than a magnesium absorption rate in the other case. Thus, for a magnesium-counter ion compound associated with a relatively low magnesium loading capacity, a simple increase in dosage may be insufficiently effective or ineffective for efficient magnesium intake, provision, and/or supplementation.

A magnesium-counter ion compound that is suitably bioavailable may be associated with a suitable or good magnesium absorption rate and/or a suitable or good magnesium loading capacity. A magnesium-counter ion compound of suitable bioavailability may be provided to a subject in a relatively high dosage in order to provide magnesium to a subject with suitable speed. In some embodiments, a magnesium-counter ion compound having a relatively high concentration in an aqueous medium or solvent may be orally administered to a subject for relatively rapid delivery of magnesium to the subject. Rapid delivery of magnesium may be important in some cases, such as in the treatment of a subject having a severe magnesium deficit and/or another condition amenable to treatment in this manner, for example. Oral administration may be relatively more convenient than intravenous injection in such cases and/or other cases.

The amount of magnesium that can be absorbed by a subject, or the rate of absorption of magnesium by a subject may vary from subject to subject, based on any of a variety of factors. Examples of such factors include metabolic rate, kidney function, overall health, and/or other factor(s) concerning a subject, and a property or nature of the magnesium-counter ion compound itself, such as the counter ion, any enhancing agent, its administration vehicle or method, and/or other factor(s) concerning the magnesium-counter ion compound and/or its administration to a subject.

Determining an appropriate dosage for administration of a magnesium-counter ion compound to a subject may take into account any of a variety of factors, such as those just mentioned, for example, any potential or actual side-effect(s), and/or a purpose of the administration of the magnesium-counter ion composition, such as a nutritional or prophylactic purpose, a cognition maintenance or enhancement purpose, a disease or pathological condition treatment purpose, and/or other purpose(s) for which the magnesium-counter ion composition may be administered to a subject. Determining an appropriate dosage may take into account any of these factors, any other suitable factor(s), any side-effect(s), animal study modeling, human study modeling, clinical study modeling, drug study modeling, and any balancing therebetween.

It is contemplated that a dosage for administration of a magnesium-counter ion compound to a subject may be from about 1.5 mg/kg of body weight/day to about 18 mg/kg of body weight/day. For example, it is contemplated that a dosage for administration of a magnesium-counter ion compound to a subject may be from about 1.5 mg/kg of body weight/day to about 9 mg/kg of body weight/day of elemental magnesium associated with the at least one magnesium-counter ion compound for nutritional and/or prophylactic purpose(s); may be about 6 mg/kg of body weight/day to about 18 mg/kg of body weight/day of elemental magnesium associated with the at least one counter ion for cognition maintenance and/or enhancement purpose(s); and may be about 9 mg/kg of body weight/day to about 18 mg/kg of body weight/day of elemental magnesium associated with the at least one counter ion for disease and/or pathological condition treatment purpose(s), such as the treatment of magnesium deficiency, MCI, AD, attention deficit hyperactivity disorder, ALS, Parkinson's disease, diabetes, migraine, depression, anxiety disorder, mood disorder, and/or hypertension, for example. Such amounts may be suitable for a human subject, for example.

As mentioned above, such a dosage may be determined, modified and/or refined based on any suitable factor(s), such as results of clinical trials concerning subjects, for example human subjects. In some embodiments, a suitable dosage may be determined, modified and/or refined based on a determination of a suitable dosage for a suitable animal model, based on experimental studies or tests, for example, and conversion of such a suitable animal dosage to a suitable human dosage, based on suitable conversion factor(s), such as any suitable established conversion factor(s), for example. Further by way of example, it is contemplated that any such suitable human dosage may be further determined, modified and/or refined based on clinical trials involving human subjects, for example.

As mentioned above, a magnesium-counter ion composition appropriate for administration to a subject may also comprise at least one agent ("enhancing agent") for enhancing bioavailability of magnesium associated with a counter ion of the composition or more than one counter ion of the composition. The enhancing agent may be any suitable agent, such as a biologically acceptable agent. Merely byway of example, a mass ratio of an amount of elemental magnesium associated with the at least one counter ion and an amount of the at least one enhancing agent may be from about 1 to about 5 (~1:~5) to about 1 to about 3000 (~1:~3000); or from about 1 to about 10 (~1:~10) to about 1 to about 1000 (~1:~1000); or from about 1 to about 200 (~1:~200) to about 1 to about 3000 (~1:~3000). Herein, such a mass ratio refers to a ratio of a total mass of a single magnesium-counter ion compound, if only one is present in the composition, or of multiple magnesium-counter ion compounds, if more than one are present in the composition, to a total mass of a single enhancing agent, if only one is present in the composition, or of multiple enhancing agents, if more than one are present in the composition.

Merely by way of example, a magnesium-comprising composition appropriate for administration to a subject may comprise at least one MCC and at least one component of non-acidified milk sufficient to enhance bioavailability of magnesium associated with at least one MCC. A component or several components of non-acidified mammalian milk other than water, such as lactose, a fatty acid or milk fat thereof, and/or another organic component thereof, for example, may enhance the bioavailability of magnesium associated with an MCC or more than one MCC. The mammalian milk source of such a component or such components may be that having its original amount of milk fat, such as a naturally occurring amount of milk fat, for example, or an amount of milk fat that is less than its original amount of milk fat, such as a manipulated or artificially reduced amount of milk fat. Accordingly, a component, such as a fatty acid component, for example, may be more or less fatty and/or have a greater or lesser chain length, for example. The mammalian milk source of such a component or such components may be non-acidified, as acidification, such as that associated with fermentation, for example, may alter the component or the components such that magnesium bioavailability is not enhanced or not sufficiently enhanced by the presence of the component or the components in the composition. Merely by way of example, while lactose may be a suitable enhancement agent, lactic acid, a product of lactose acidification, may not. Merely by way of example, a suitable non-acidified mammalian milk source may have a pH of from about 5.7 to about 7.2.

Merely by way of example, a magnesium-comprising composition appropriate for administration to a subject may comprise at least one MCC and lactose, the latter of which may act as an enhancing agent. In such a case, the mass ratio of an amount of elemental magnesium associated with the at least one MCC to an amount of lactose may be from about 1 to about 10 (~1:~10) to about 1 to about 1000 (~1:~1000). Further, merely by way of example, a magnesium-comprising composition appropriate for administration to a subject may comprise at least one MCC and the complete organic components, excluding water, of non-acidified milk, the latter of which may comprise an enhancing agent or enhancing agents. In such as case, the mass ratio of elemental magnesium associated with the at least one MCC to the enhancing agent(s) may be from about 1 to about 200 (~1:~200) to about 1 to about 3000 (~1:~3000).

As described above, a magnesium-comprising composition appropriate for administration to a subject may comprise at least one MCC, such as magnesium gluconate, magnesium lactate, and/or magnesium citrate, for example. Each of magnesium gluconate, magnesium lactate, and magnesium citrate is commercially available and relatively palatable. An MCC, or composition comprising same, that is tolerably or relatively palatable may be used in a food, a beverage, and/or another type of consumable vehicle that may be associated with a diet of a subject, such as a human subject, for example. As such, the subject may be able to provide and/or supplement a normal magnesium intake via a diet comprising at least one such magnesium-comprising consumable vehicle, rather than via a relatively non-dietary means, such as at least one magnesium-containing pill, capsule, and/or tablet, for example. Naturally, a subject may employ one or more than one means of magnesium intake, provision, and/or supplementation.

As also described above, a magnesium-comprising composition appropriate for administration to a subject may comprise more than one MCC, or a combination of MCCs. Merely by way of example, such a magnesium-comprising composition may comprise at least two MCCs, such as at least two MCCs of any of the MCCs described herein. Further, merely by way of example, a magnesium-comprising composition may comprise at least two MCCs selected from magnesium gluconate, magnesium lactate, magnesium citrate, and magnesium malate, for example, or selected from magnesium gluconate, magnesium lactate, and magnesium citrate, for example, such as all three of magnesium gluconate, magnesium lactate, and magnesium citrate, for example. Still further, merely by way of example, a magnesium-comprising composition may comprise magnesium lactate in an amount from about 5 to about 50%, such as about 25%, for example; magnesium citrate in an amount of from about 5 to about 50%, such as about 25%, for example; and/or magnesium gluconate in an amount from about 10 to about 70%, such as about 50%, for example, where all percentages are weight percentages relative to the total weight of any of these three MCCs present. Any such composition may also comprise any suitable enhancing agent, such as any described herein, for example.

Magnesium lactate is associated with a relatively good magnesium content of about 12 percent by weight. Magnesium citrate is associated with a relatively good magnesium content of about 18.46 percent by weight. While magnesium gluconate is associated with a comparatively lower magnesium content of about 5.86 percent by weight and comparatively lower palatability, particularly at high concentration, it is also associated with a solubility in water or an aqueous medium that is comparatively better than that associated with either magnesium lactate or magnesium citrate. As described above, a magnesium-comprising composition may comprise at least two MCCs selected from magnesium gluconate, magnesium lactate, and magnesium citrate, such as all three of these MCCs, for example.

A magnesium-counter ion composition comprising more than one magnesium-counter ion compound may be suitable, beneficial or desirable relative to a magnesium-counter ion composition comprising a single magnesium-counter ion compound. A combination of more than one magnesium-counter ion compound may be suitable, beneficial or desirable in terms of any number of features or factors, such as magnesium content, solubility, palatability, magnesium bioavailability, biological acceptability, and/or the like, for example. A combination of more than one magnesium-counter ion compound may be suitable, beneficial or desirable in terms of palatability. A combination of more than one magnesium-counter ion compound may be suitable, beneficial or desirable in terms of maintaining and/or enhancing an attribute or attributes of a magnesium-counter ion compound or several magnesium-counter ion compounds.

In terms of solubility, a magnesium-counter ion compound, or more than one magnesium-counter ion compound, may have solubility in water of at least about 20 mM, such as at least about 50 mM or at least about 80 mM, merely by way of example. In terms of magnesium content, an magnesium-counter ion compound or more than one magnesium-counter ion compound may have a magnesium content of at least about 8 weight percent. In terms of bioavailability, a magnesium-counter ion compound or more than one magnesium-counter ion compound may be associated with a bioavailability that is at least comparable to that associated with magnesium chloride, if not greater.

Figure 2:
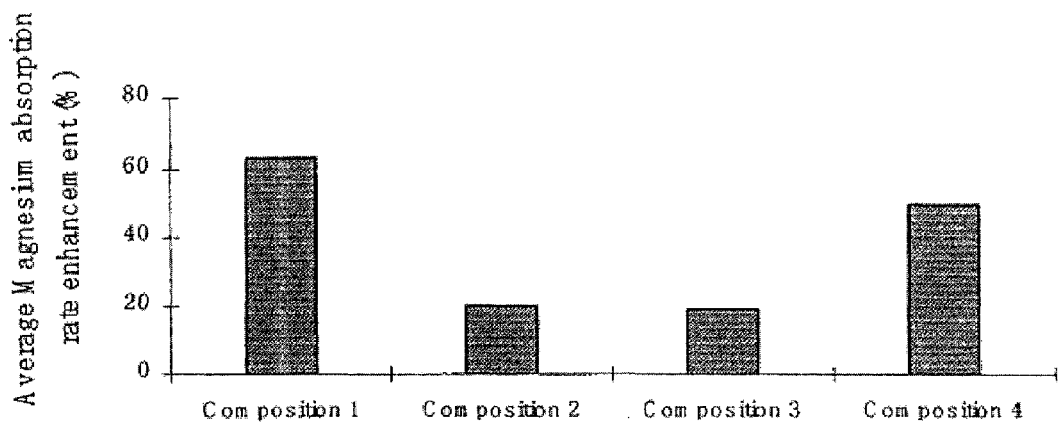
FIG. 2 is a graphical presentation of the enhancement of the magnesium absorption rate in four groups of young adult rats that were exposed, respectively, to four different compositions: 1) magnesium gluconate (12 mM) in skim milk; 2) magnesium gluconate (12 mM) in milk prepared from powdered milk; 3) magnesium gluconate (12 mM) in water comprising 1% cream; or 4) magnesium gluconate (12 mM) in water comprising 5 weight percent lactose. The enhancement of the magnesium absorption was measured, as a percentage relative to the magnesium absorption rate in a control group of young adult rats that were exposed to a composition comprising magnesium gluconate (12 mM) and water, as further described in Example 3.
Figure 3:
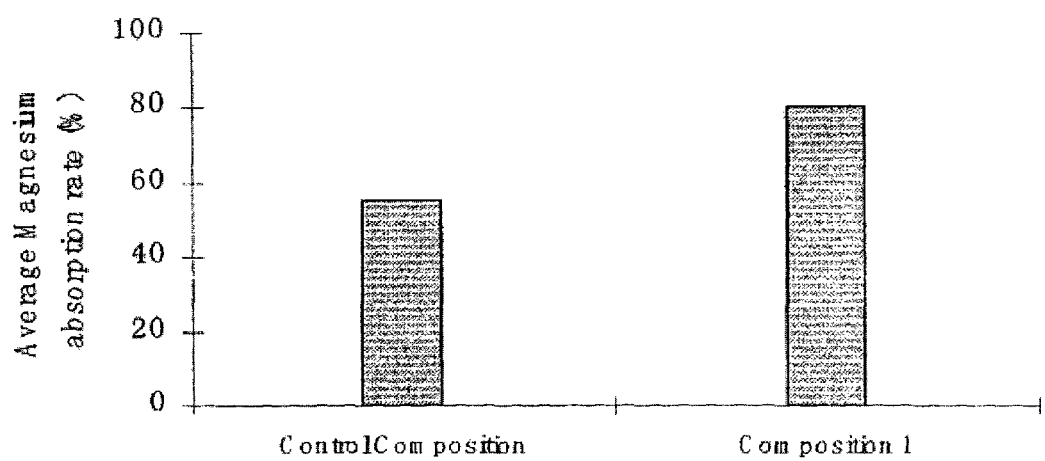
FIG. 3 is a graphical presentation of the magnesium absorption rate in young adult rats that were exposed to a composition of a mixture of magnesium-counter ion components and water and the magnesium absorption rate in young adult rats that were exposed to a composition of the same mixture of magnesium-counter ion components and skim milk, as further described in Example 4.
Figure 4:
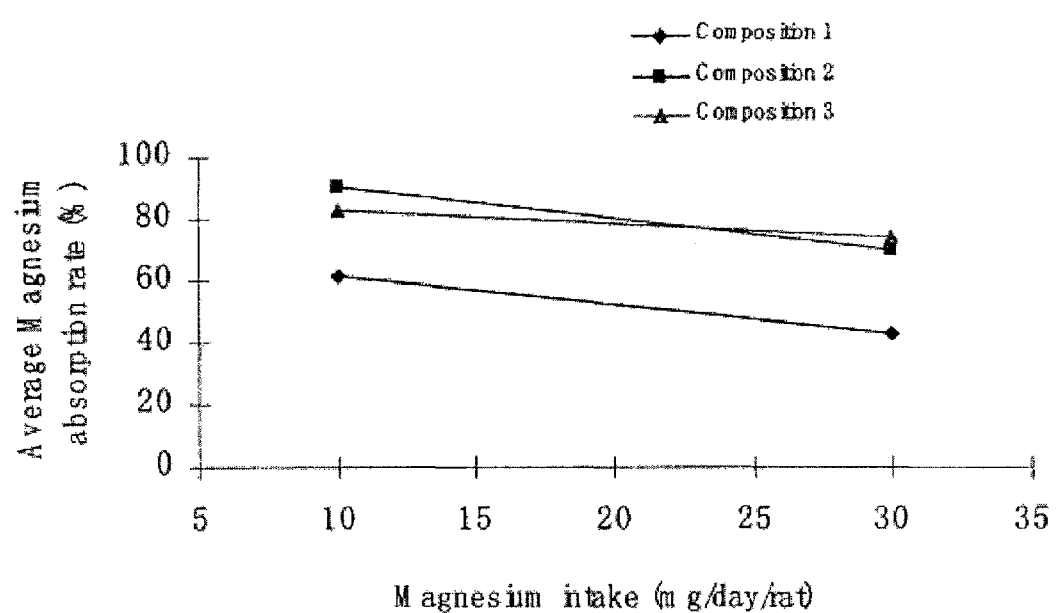
FIG. 4 is a graphical presentation of the magnesium absorption rate in young adult rats that were exposed to a composition of magnesium chloride and water, magnesium gluconate and skim milk, or magnesium gluconate and in water comprising 5 weight percent lactose, versus the elemental magnesium intake (mg/day/rat), as further described in Example 5.

A magnesium-comprising composition comprising at least one MCC and an enhancing agent may be associated with suitable magnesium bioavailability. Such a composition may be associated with a suitable magnesium absorption rate. By way of example, when rats were fed different compositions comprising magnesium gluconate, at a concentration of 12 mM, in different media, namely, skim milk, water comprising 5 weight percent by lactose, milk prepared from powdered milk and water, milk cream and water, and a control medium of water, respectively, each of the four compositions outperformed the control composition in terms of magnesium absorption rate. Further, as graphically depicted in FIG. 2 and described in Example 3, each of the compositions comprising a medium other than the control medium outperformed the composition comprising the control medium, water, in terms of the percentage of magnesium absorption rate enhancement. Further by way of example, when rats were fed a composition comprising a combination of magnesium gluconate, magnesium lactate, and magnesium citrate, and skim milk, the composition was associated with a suitable magnesium absorption rate, one that was higher than that associated with a control composition comprising the same combination of magnesium gluconate, magnesium lactate, and magnesium citrate, but water in place of skim milk, as graphically depicted in FIG. 3 and described in Example 4. Further by way of example, when rats were fed compositions comprising magnesium gluconate, at various relatively low magnesium dosages, and either skim milk or water comprising 5 weight percent lactose, the compositions were associated with suitable magnesium absorption rates, as graphically depicted in FIG. 4 and described in Example 5.

A magnesium-counter ion composition comprising at least one counter ion and an enhancing agent may be associated with a suitable magnesium loading capacity, such as a relatively high loading capacity, for example. Such a composition may be associated with a relatively high magnesium absorption rate, for example, throughout a relatively wide dosage range. When such a composition is administered to a subject in a relatively high dosage, the subject may be able to absorb a suitable amount of magnesium, such as a nutritional, therapeutic, and/or prophylactic amount, or may be able to do so in a relatively short period. By comparison, when a composition associated with a low magnesium loading capacity is administered to a subject in a relatively high dose, the subject may not be able to absorb a suitable amount of magnesium, such as a nutritional, therapeutic, and/or prophylactic amount, or may not be able to do so in a relatively short period. That is, in the latter case, simply administering a large dosage of a composition associated with a low magnesium loading capacity to a subject may not be sufficient or effective for a particular purpose. By way of example, when rats were fed compositions comprising magnesium gluconate, at a relatively low magnesium dosage and at a relatively high magnesium dosage, and either skim milk or water comprising 5 weight percent lactose, the lower dosage compositions were associated with suitable magnesium absorption rates and the higher dosage compositions were associated with suitable magnesium absorption rates that were suitably close to those associated with the lower dosage compositions, as graphically depicted in FIG. 4 and described in Example 5. These magnesium gluconate-comprising compositions were thus associated with suitable magnesium loading capacities. A composition comprising magnesium gluconate and milk, lactose, or another enhancing agent, when administered at high dosage, may thus be suitable for rapid and/or efficient magnesium intake, provision, and/or supplementation. By way of comparison, when rats were fed compositions comprising magnesium chloride, at a relatively low magnesium dosage and at a relatively high magnesium dosage, and water, the lower dosage compositions were associated with suitable, but lower, magnesium absorption rates and the higher dosage compositions were associated with magnesium absorption rates that were less desirable, as graphically depicted in FIG. 4 and described in Example 5. Thus, while magnesium chloride has previously been associated with very good bioavailability, that level of bioavailability may be associated with a relatively low dosage, and not with a relatively high dosage. A composition comprising magnesium chloride and water, when administered at high dosage, may thus be less desirable or suitable, and perhaps unsuitable, for rapid and/or efficient magnesium intake, provision, and/or supplementation.

A magnesium-counter ion compound appropriate for administration to a subject may comprise magnesium threonate, in which each magnesium cation is associated with two threonate anions, as illustrated in the formula provided below.

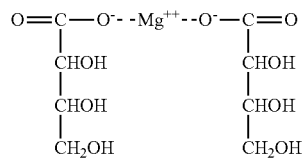

Such a composition may be prophylactically and/or therapeutically suitable or beneficial. Threonate is a natural metabolic product of vitamin C or ascorbic acid that may be associated with non-toxicity in animals (Thomas et al., *Food Chem.* 17, 79-83 (1985)) and biological benefit, such as the promotion of vitamin C uptake, in animals (Verlangieri et al., *Life Sci.* 48, 2275-2281 (1991)).

Figure 5:
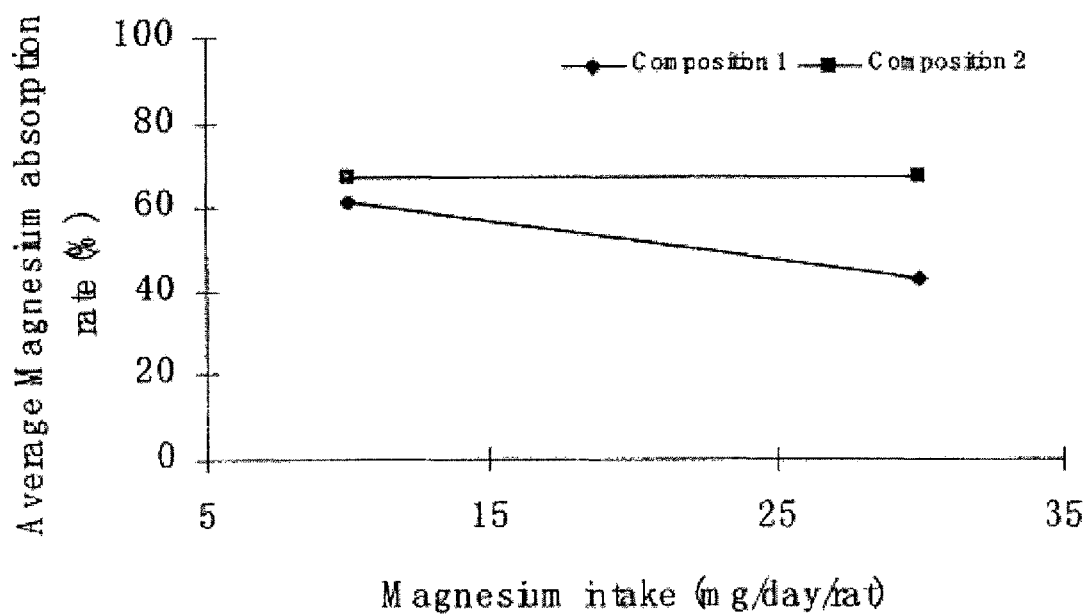
FIG. 5 is a graphical presentation of the magnesium absorption rate in young adult rats that were exposed to a composition of magnesium chloride and water, or magnesium threonate and water, versus the elemental magnesium intake (mg/day/rat), as further described in Example 6.

Magnesium threonate may be associated with suitable magnesium bioavailability in relation to a subject. As such, a magnesium-counter ion composition appropriate for administration to a subject may comprise magnesium threonate, and optionally, an enhancing agent. By way of example, when rats were fed a relatively dilute composition comprising magnesium threonate and water, at a relatively low dosage, the composition was associated with a suitable magnesium absorption rate, as graphically depicted in FIG. 5 and described in Example 6. As shown, the magnesium absorption rate of this composition was similar to that associated with a similarly tested composition comprising magnesium chloride and water, at a relatively low dosage, as graphically depicted in FIG. 5 and described in Example 6. When rats were fed a composition comprising magnesium threonate and water, at a higher dosage, the composition was still associated with a suitable absorption rate, as graphically depicted in FIG. 5 and described in Example 6. As shown, the magnesium absorption rate of this composition was significantly higher than that associated with a similarly tested composition comprising magnesium chloride and water, at a higher dosage, as graphically depicted in FIG. 5 and described in Example 6. A composition comprising magnesium threonate may thus be associated with a suitable magnesium loading capacity and may be suitable for rapid and/or efficient magnesium intake, provision, and/or supplementation.

Magnesium threonate may be more suitable or desirable for oral administration to a subject than some other magnesium-counter ion compounds, such as various inorganic magnesium compounds and various magnesium chelates. The oral administration of various inorganic magnesium compounds, such as magnesium chloride and magnesium sulfate, for example, at high dosages, may contribute or lead to diarrhea, a laxative effect, and/or the like. In view of the laxative effect of magnesium sulfate on the digestive system, magnesium sulfate may be administered by intravenous injection for non-laxative purposes in order to avoid the digestive system altogether. Further, oral administration of various magnesium chelates, such as magnesium diglycinate, may be complicated by alkalinity and/or palatability concerns. A magnesium chelate may comprise one magnesium ion associated with one amino acid molecule or two amino acid molecules and may be associated with relatively high bioavailability. A magnesium chelate may be highly alkaline at a pH of 10 or more when dissolved in water. A magnesium chelate may be associated with a smell or a taste like that associated with rotten fish, perhaps reflecting that the amine groups thereof are relatively free as opposed to stably bonded in relation to the magnesium. In view of alkalinity, sensory and/or palatability concerns that may be associated with a magnesium chelate, such compounds may be not be the most suitable for magnesium intake, provision, and/or supplementation via a consumable vehicle or oral administration.

Magnesium threonate does not present the challenges that may be associated with various inorganic magnesium compounds and various magnesium chelates. A composition comprising magnesium threonate was shown to have a more suitable magnesium loading capacity than a composition comprising magnesium chloride, as described in relation to FIG. 5 and Example 6. Briefly, ten adult male rats were fed a magnesium threonate solution having a magnesium threonate concentration of 48 mM over a three-month period, for an average magnesium dosage of 40 mg/kg of body weight/day, they did not show signs of diarrhea. Still further, when rats were exposed to a diet including a magnesium-counter ion composition of magnesium threonate in water, their serum magnesium concentration was greater than that associated with rats that were exposed to a diet including either of two other magnesium-counter ion compositions, or a diet including de-ionized water, as graphically depicted in FIG. 6 and described in Example 7. A magnesium-counter ion compound sufficient to produce a relative high magnesium concentration in blood (e.g., magnesium threonate) may be useful in any of a variety of applications, such as a therapeutic application, for example.

Magnesium threonate may be suitable for relatively rapid magnesium intake, provision, and/or supplementation, as may be suitable or beneficial for any of a variety of applications, such as a nutritional or prophylactic application, and/or a therapeutic application. Magnesium threonate may be a suitable or beneficial vehicle for magnesium intake, provision, and/or supplementation application(s), such as any that may be accomplished via a dietary vehicle or a consumable vehicle, such as a magnesium-fortified food and/or a magnesium-fortified beverage, for example.

A magnesium-counter ion compound appropriate for administration to a subject may be useful in nutritional applications and/or therapeutic applications. A nutritional application may refer to an application suitable for warding off and/or preventing pathological condition and/or disease associated with magnesium deficit and/or subject to treatment with magnesium, such as AD, MCI, and/or diabetes. A nutritional application may refer to an application suitable for maintaining and/or enhancing physiological function, such as physiological function at a state considered normal. A level of cognitive function, such as learning or memory function, for example, of a healthy human may be maintained and/or enhanced by administering a suitable magnesium-counter ion composition. A therapeutic application includes, but is not limited to, treating pathological condition and/or disease associated with magnesium deficit and/or subject to treatment with magnesium, such as AD, MCI, ALS, Parkinson's disease, diabetes, and/or hypertension.

A magnesium-counter ion compound, such as magnesium threonate, and/or a composition comprising one or more magnesium-counter ion compounds, may be sufficient to at least maintain and/or to enhance cognitive function. In such a composition, an amount of magnesium, or an effective amount of same, associated with at least one magnesium-counter ion compound may be sufficient for any suitable function described herein. For example, a concentration of elemental magnesium associated with at least one counter ion of such a composition in a liquid form (e.g., an aqueous solution) may be from about 5 mg/L to about 12 g/L, such as from about 50 mg/L to about 12 g/L, for example.

A magnesium-counter ion compound, such as magnesium threonate and/or a composition comprising one or more counter ions, may be sufficient for treating MCI, AD, and/or any other suitable malady or disease. In such a composition, an amount of magnesium, or an effective amount of same, associated with at least one magnesium-counter ion component may be sufficient for any suitable function described herein. For example, a concentration of elemental magnesium associated with at least one counter ion of such a composition in a liquid form (e.g., an aqueous solution) may be from about 5 mg/L to about 12 g/L, such as from about 50 mg/L to about 12 g/L, for example.

A subject afflicted with AD may have trouble carrying out a task, such as speaking, understanding, writing, reading, grooming, drinking, or eating, for example, either with or without assistance. Before now, AD has been considered an incurable disease that typically becomes worse over time. Various drugs that have been used to treat AD have been designed to slow its progression. Some of these drugs have been associated with various side-effects, some of which may be significant or serious. A subject afflicted with MCI may experience forgetfulness that can affect daily life. Before now, no treatment has been available specifically for MCI, which may progress into AD. Various drugs that have been used to treat AD may not be suitable for treating the milder disease, MCI, in view of associated side-effects. A magnesium-counter ion compound, such as magnesium threonate, for example, and/or composition comprising one or more magnesium-counter ion compounds, may be sufficient for any suitable purpose described herein, such as treating AD and/or MCI and/or ameliorating a symptom associated therewith, for example, while not giving rise to an undesirable side-effect of significance.

Figure 7:
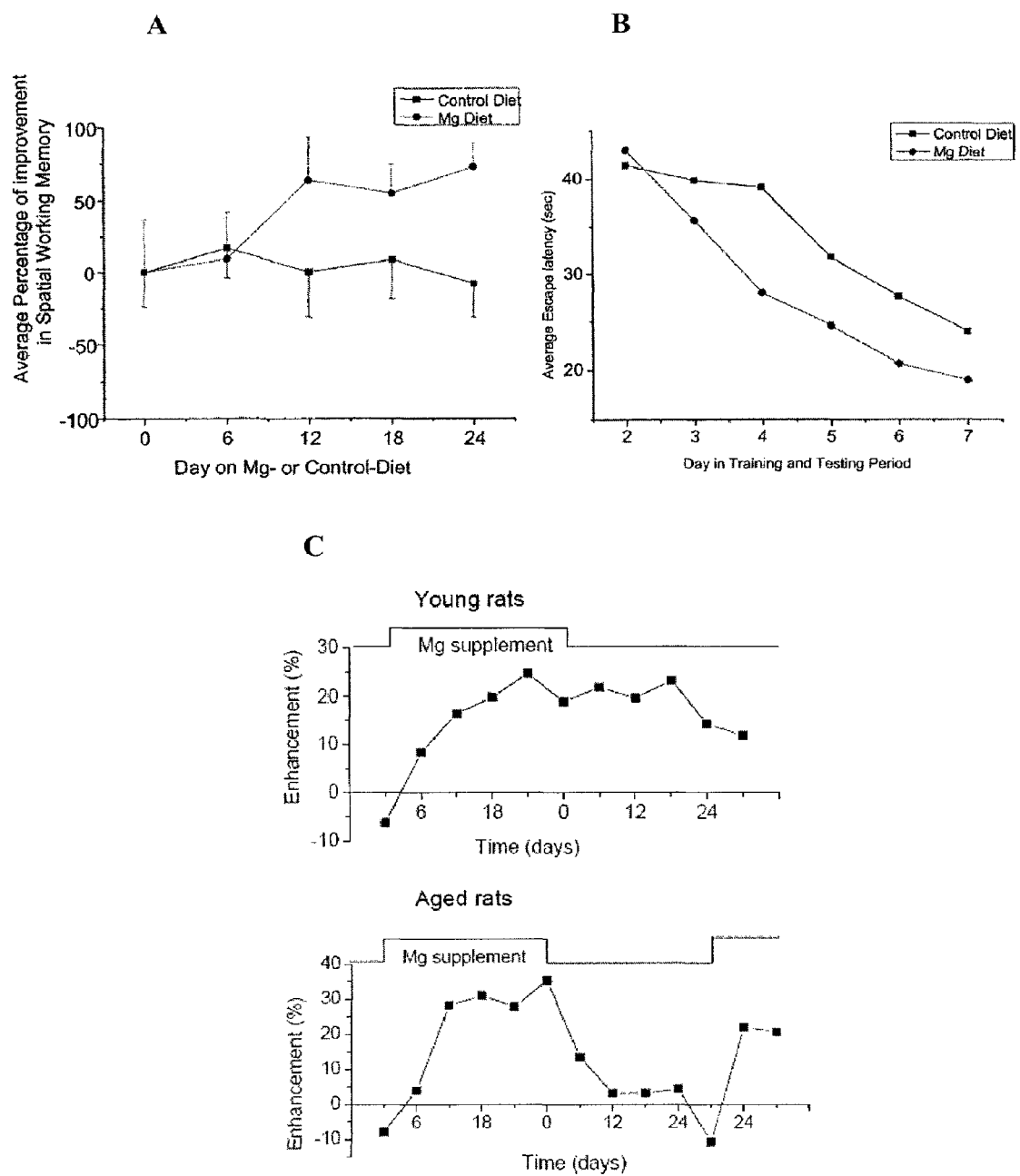
FIG. 7 is a graphical representation of the average percentage improvement of spatial working memory results for various young and aged rats that were fed various diets, plotted for various days of a training and testing period (panels A and B); and the percentage enhancement in young and aged rats receiving magnesium supplementation (panel C).

In some embodiments, the magnesium-counter ion compounds of the present invention may be administered to a subject to address cognitive function, whether nutritionally or prophylactically or therapeutically, in any suitable manner. As graphically depicted in FIG. 7 and described in Example 8, AD-afflicted mice fed a magnesium-fortified diet for over a month were shown to have improved short-term spatial memory and learning capacity, relative to AD-afflicted mice fed a normal diet.

A magnesium-counter ion compound described herein may be administered to a subject, whether or not afflicted with cognitive decline, deficiency, and/or impairment, to address cognitive function, whether nutritionally or prophylactically or therapeutically, in any suitable manner. For example, such compounds may be administered to a relatively young and/or healthy subject. A magnesium-counter ion compound described herein may be administered to a subject to achieve its purpose, such as addressing of cognitive function in any suitable manner, in a relatively short period. As graphically depicted in FIG. 8 and described in Example 9, young rats, none of which had been associated with cognitive decline, deficiency, and/or impairment, fed a magnesium-fortified diet over time were shown to have markedly improved over time in terms of enhancement of spatial working memory and learning. In contrast, such rats fed a normal diet over time were generally shown not to have improved in this manner over time. Further, the rats that showed marked improvement did so over a period of less than two weeks.

It is contemplated that a magnesium-counter ion compound described herein may be administered to a human subject to suitable or beneficial effect, such as nutritional, prophylactic, and/or therapeutic effect, for example, as may be useful to address cognitive function, for example, in any suitable manner. In some embodiments, a magnesium-counter ion compound of the present invention may be administered to a human subject susceptible to, or afflicted by, MCI and/or AD to suitable or beneficial effect. In other embodiments a magnesium-counter ion compound, or a composition containing such a compound, may be administered to a human subject for a variety of useful purposes, such as the maintenance, enhancement, and/or improvement of cognitive function, learning, memory, mood, anxiety, depression, migraine, and/or other conditions. As the magnesium-counter ion composition comprises an endogenous mineral, magnesium, and possibly other natural ingredients, such as an enhancing agent described herein, for example, in most embodiments administration of the magnesium-counter ion compounds of the present invention may be safe over a relatively long term. In still other embodiments, administration of such a magnesium-counter ion compound or composition occurs over a long-term period. For example, a subject may be administered the compound and/or compositions of the present invention for weeks, months, years, and/or for life. Such long-term administration may be used for preventing or treating a condition, such as MCI, or may be useful for preventing progression of a condition (e.g., preventing the progression of a condition, such as MCI, into another condition, such as AD). These examples are not limiting examples, as long-term administration of the magnesium-counter ion compounds of the present invention may be used for multiple purposes as described herein and as recognized by one of skill in the art.

A magnesium-counter ion composition described herein may comprise one or more other suitable component(s), such as a suitable pharmaceutical composition or drug associated with the treatment of MCI, AD, diabetes, ADHD, ALS, Parkinson's disease, ALS, and/or hypertension, for example. Magnesium, particularly in the form of a magnesium-counter ion compound of the present invention (e.g., magnesium threonate) may be effective in the treatment of hypertension. A subject afflicted with MCI, AD, and/or diabetes may have a magnesium deficiency, which may be addressed by a pharmaceutical composition drug used to treat the affliction. It is contemplated that magnesium and such a pharmaceutical composition or drug in a magnesium-counter ion composition described herein may work synergistically in a suitable manner, such as a biologically beneficial and/or a therapeutically effective manner. Non-limiting examples of a pharmaceutical composition or drug associated with the treatment of AD include acetylcholine esterase inhibitors, (e.g., donepezil, rivastagmine, or galantamine) and NMDA channel blockers, such as memantine. One of skill in the art will recognize that these pharmaceuticals are given merely by way of example and do not delineate the scope of pharmaceuticals which may be used in combination with the magnesium-counter ion compounds of the present invention.

A magnesium-counter ion compound appropriate for administration to a subject may be administered in any suitable manner. Such administration may be oral and/or any other suitable administration, such as transdermal, intramuscular, vaginal, rectal, subdermal. Components of a magnesium-counter ion composition, such as at least one magnesium-counter ion compound and at least one agent for enhancing bioavailability of magnesium may be administered to a subject concurrently, such as in any manner of concurrent administration described herein and/or in U.S. Patent Application Publication No. US 2006/0089335 A1.

A magnesium-counter ion compound appropriate for administration to a subject may be provided in any suitable form, such as a liquid form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form, a food form, a chewable form, a non-chewable form, a slow- or sustained-release form, a non-slow- or non-sustained-release from, and/or the like, may be employed. Gradual-release tablets are known in the art. Examples of such tablets are set forth in U.S. Pat. No. 3,456,049. Such a composition may comprise an additional agent or agents, whether active or passive. Examples of such an agent include a sweetening agent, a flavoring agent, a coloring agent, a filling agent, a binding agent, a lubricating agent, an excipient, a preservative, a manufacturing agent, and/or the like, merely by way of example, in any suitable form. A slow- or sustained-release form may delay disintegration and/or absorption of the composition and/or one or more component(s) thereof over a period, such as a relatively long period, for example. A food form may take the form of a food bar, a cereal product, a bakery product, a dairy product, and/or the like, for example. A bakery product form may take the form of a bread-type product, such as a bagel or bread itself, for example, a donut, a muffin, and/or the like, merely by way of example. A component of a magnesium-counter ion composition may be provided in a form that is other than that of another component of the magnesium-counter ion composition. For example, at least one magnesium-counter ion compound may be provided in a solid form, such as solid food or cereal that is taken with an enhancing agent in a liquid form, such as a liquid dietary substance. Such administration of magnesium-counter ion compositions in multiple forms, may occur simultaneously (e.g., ingesting a magnesium threonate tablet with magnesium threonate-fortified milk), or at different times.

In some embodiments, a magnesium-counter ion composition in the form of a pill, tablet, capsule, or like device, may comprise from about 30 mg to about 200 mg of elemental magnesium. In other embodiments, a magnesium-counter ion composition may contain from about 50 mg to about 100 mg of elemental magnesium associated with the at least one magnesium-counter ion compound. In still other embodiments, a magnesium-counter ion composition in the form of a food serving, or like dietary serving, may comprise from about 20 mg to about 1 g or even 1.5 g of elemental magnesium. In still other embodiments, a magnesium-counter ion composition in the form of a food serving, or like dietary serving, may comprise from about 50 mg to about 800 mg of elemental magnesium.

A magnesium-counter ion composition appropriate for administration to a subject may be provided in a liquid form, such as one suitable for oral administration, parenteral administration and/or other appropriate routes. Such a composition may comprise any suitable additional agent or agents, whether active or passive. Examples of such agents include water, a sweetening agent, a flavoring agent, a coloring agent, a texturing agent, a stabilizing agent, a preservative, a manufacturing agent, and/or the like, in any suitable form. A component that may negatively affect magnesium bioavailability, such as a phosphate or a polyphosphate, for example, may be avoided. A magnesium-counter ion composition in a liquid form may comprise from about 5 mg/L to about 12 g/L, such as from about 50 mg/L to about 12 g/L, for example, of elemental magnesium associated with the magnesium-counter ion of the composition. An amount of from about 50 mg/L to about 3 g/L, such as from about 100 mg/L to about 1.5 g/L, for example, of elemental magnesium associated with the magnesium-counter ion may be suitable for prophylactic application and/or nutritional application. An amount of from about 300 mg/L to about 12 g/L, such as from about 500 mg/L to about 3.5 g/L, for example, of elemental magnesium associated with the magnesium-counter ion may be suitable for therapeutic application.

A magnesium-counter ion composition in a liquid form may be used in any suitable manner. In some embodiments, the magnesium-counter ion composition may be used as a beverage, such as a milk-based beverage, a sports drink, a fruit juice drink, an alcoholic beverage, and/or the like. In other embodiments, the magnesium-counter ion composition in liquid form contains multiple magnesium-counter ion compounds. In such embodiments, the weight percentage of each magnesium-counter ion compound may vary in relation to the other. In still other embodiments, the magnesium-counter ion composition in a liquid form may take the form of a magnesium-fortified product comprising water, magnesium threonate, and, optionally, at least one agent sufficient to confer a suitable property to the product. In still another embodiment, a magnesium-counter ion composition in a liquid form may be formulated from a dry mix, such as a dry beverage mix or a magnesium-fortified, milk-comprising powder. A dry mix may be suitable in terms of transportation, storage, and/or shelf life. The composition may be formulated from the dry mix in any suitable manner, such as by adding a suitable liquid (e.g., water, milk, fruit juice, alcohol, etc.).

Examples concerning magnesium-counter ion compound(s) and magnesium-counter ion composition(s), and the preparation, testing and/or use of same, are provided below.

Use as Dietary Supplement

One embodiment of the present invention is a magnesium dietary supplement. In some embodiments, the magnesium supplement contains one or more magnesium-counter ion compounds of the present invention and may optionally contain other ingredients generally recognized as safe for food additive use, including, but not limited to, preservatives (e.g., butylated hydroxytoluene, butylated hydroxyanisole), food grade emulsifiers (e.g., lecithin, propylene glycol esters), and pharmaceutically acceptable carriers and excipients (e.g., binders, fillers, lubricants, dissolution aids).

In one embodiment, the magnesium-counter ion supplement composition of the present invention is made by combining magnesium threonate or other magnesium compounds of the invention, as well as any optional components, in the desired relative amounts and mixing the components according to known methods to produce a substantially homogeneous mixture.

In another embodiment, the magnesium-counter ion composition may also contain other nutritional active materials including, without limitation, calcium-containing materials such as calcium carbonate, stannol esters, hydroxycitric acid, vitamins, minerals, herbals, spices and mixtures thereof. Examples of vitamins that are available as additional ingredients include, but are not limited to, vitamin A (retinol), vitamin D (cholecalciferol), vitamin E group (alpha-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final product is dependent on the particular vitamin. Examples of minerals that are available as additional ingredients include, but are not limited to, calcium, magnesium, phosphorus, iron, zinc, iodine, selenium, potassium, copper, manganese, molybdenum and mixtures thereof. As is the case with vitamins, the amount of mineral or minerals present in the final product is dependent on the particular mineral. It will be clear to one of skill in the art that the present list of additional neutriceutical components are provided by way of example only, and are not intended to be limiting.

Magnesium threonate is a highly bioavailable form of a magnesium counter-ion composition. However, the in vivo accessibility of this magnesium threonate may be provided in multiple ways. In some embodiments, a subject ingests magnesium threonate. In other embodiments, magnesium may be taken with other supplements which result in an in vivo reconstitution of magnesium-counter ion composition. Without being bound by theory, the threonate may function to promote cellular uptake of magnesium in any form and may also enhance delivery to the brain and central nervous system. Thus, in some embodiments, magnesium may be given uncomplexed with threonate and threonate is provided to the same subject to enhance absorption. For example, magnesium gluconate and potassium threonate may be taken essentially concurrently to result in an in vivo reconstitution of magnesium threonate and/or enhance magnesium uptake and/or delivery of magnesium to the brain. In another example, certain counter ions may be metabolic products of other substances. For example, vitamin C is metabolized into the threonate ion in humans; therefore, ingestion of magnesium in a form which can be taken up by the body and vitamin C may result in the reconstitution of magnesium threonate in the body. Another example of a substance which is metabolized to threonate in humans is ascorbate. Thus, in some embodiments of the present invention, magnesium ascorbate may be provided to a subject and this substance would be metabolized to magnesium and threonate in vivo. One of skill in the art will recognize that these examples are provided by way of illustration only and that other combinations of magnesium compounds and secondary compounds may result in the reconstitution of a magnesium-counter-ion composition in vivo.

In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables.

In an embodiment, food carriers employed herein can mask the undesirable taste (e.g., bitterness), if present in one or more of the subject magnesium-counter ion compounds. Where desired, the food composition presented herein exhibit more desirable textures and aromas than that of the magnesium-counter ion compounds.

For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like In another embodiment, the supplement composition of the present invention may be administered in any oral dosage form, including liquid dosage forms (e.g., a suspension or slurry), and oral solid dosage forms (e.g., a tablet or bulk powder). As used herein the term "tablet" refers generally to tablets, caplets, capsules, including soft gelatin capsules, and lozenges.

Tablets are made by methods known in the art and may further comprise suitable binders, lubricants, diluents, disintegrating agents, colorants, flavoring agents, flow-inducing agents, melting agents which are known in the art. The oral solid dosage form may, optionally, have a film coating to protect the components of the magnesium-counter ion supplement composition from one or more of moisture, oxygen and light or to mask any undesirable taste or appearance. Suitable coating agents include, for example, cellulose, hydroxypropylmethyl cellulose. Where desired, tablets can be formulated in sustained release format. Methods of making sustained release tablets are known in the art, e.g., see US2006051416 and US20070065512, both of which are incorporated herein by reference.

In still other embodiments, magnesium-counter ion compounds of the present invention are added to foodstuffs. Such foodstuffs may be naturally high or low in magnesium. Examples of foodstuffs which are high in magnesium include, but are not limited to soft drinks (e.g., coke, gaterade, coffee), milk, bran flakes, oatmeal, shredded wheat, whole wheat bread, fruit and/or vegetable juices, and potatoes. Other foodstuffs are readily apparent and multiple examples have been described. See, e.g., U.S. Pat. Nos. 6,790,462, 6,261,589, and U.S. patent application Ser. Nos. 10/725,609 and 11/602,126.

Use as Pharmaceutical

One embodiment of the present invention is a pharmaceutical composition, typically for administration to a person in need of therapeutic levels of magnesium. Various delivery systems are known and can be used to administer the magnesium compositions of the invention, e.g., encapsulation in liposomes, microparticles, microcapsules, etc. Methods of delivery include but are not limited to intra-arterial, intramuscular, intravenous, intranasal, and oral routes. In a specific embodiment, it may be desirable to administer the pharmaceutical compositions of the invention locally to the area in need of treatment; this may be achieved by, for example, and not by way of limitation, transdermal patches, local infusion during surgery, by injection, by means of a catheter (with or without an attached pump), or bathing in a magnesium solution. In some embodiments, the agents are delivered to a subject's nerve systems, preferably the central nervous system.

In some embodiments, administration of the magnesium-counter ion compositions can be effected in one dose, continuously or intermittently throughout the course of treatment. Methods of determining the most effective means and dosage of administration are well known to those of skill in the art and will vary with the composition used for therapy, the purpose of the therapy, the target cell or tissue being treated, and the subject being treated. Single or multiple administrations can be carried out with the dose level and pattern being selected by the treating physician.

For oral administration, the inventive compositions may optionally be formulated by mixing the magnesium-containing compositions with physiologically or pharmaceutically acceptable carriers that are well known in the art. Such oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated.

In one embodiment, the magnesium-containing composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing the magnesium-containing composition with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions; and suitable organic solvents or solvent mixtures. Dyestuffs or pigments may be added to the tablets or dragee coatings for identification or to characterize different combinations of active compound doses. For buccal administration, the inventive compositions may take the form of tablets or lozenges formulated in a conventional manner. For administration by inhalation, the compositions of the present invention may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas; or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparation of pharmaceutical compositions of this invention is conducted in accordance with generally accepted procedures for the preparation of pharmaceutical preparations. See, for example, *Remington's Pharmaceutical Sciences* 18*th Edition* (1990), E.W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or aerosol when used with an appropriate aerosolizer device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

In some embodiments, magnesium supplementation is provided to achieve optimal body magnesium status by supplementing a person's diet with a magnesium composition of the present invention. As described herein, there is a desired range of body magnesium, below which and above which, detrimental effects occur. For example, if body magnesium is too low, then cognitive function may result; however, a diet too high in magnesium may result in diarrhea. A formulaic approach to determining optimum magnesium dosage is more fully detailed in the examples provided. In some embodiments, use of the formulas described in the examples below (and other such methods), will allow a subject to maintain a dosage regimen which allows for a physiological concentration as high as possible, without encountering detrimental effects. A desired body magnesium status may be defined and/or determined in a variety of ways, including, but not limited to blood magnesium concentration, CSF magnesium concentration, tissue magnesium concentration, intracellular magnesium concentration, and red blood cell magnesium concentration. Desired body magnesium status may be applicable for general health as well as for specific therapeutic applications described herein (e.g., mild cognitive impairment, AD, depression, osteoporosis, diabetes, etc.). It will be understood that for treatment of different conditions, the optimal body magnesium status may be different to achieve the desired effects. For instance, by way of example only, it may be necessary to provide a person with a magnesium dosage which will increase body magnesium concentration by 10% to treat cognitive impairment, but a dosage which will increase body magnesium concentration by 15% to treat diabetes and/or cardiovascular function. In other words, the compositions described herein can be utilized for the methods described herein to achieve therapeutically effective body magnesium concentrations.

The pharmaceutical compositions can be formulated in slow release or sustained release forms, whereby a relatively consistent level of the active compound is provided over an extended period. In some embodiments, a magnesium counter-ion composition and/or other therapeutic agents may be administered jointly or separately by using a controlled release dosage form. Controlled release within the scope of this invention can be taken to mean any one of a number of extended release dosage forms. Extended release dosage forms are described in Heaton et al. U.S. Patent Application Pub. No. US2005/0129762 A1 and Edgren et al. U.S. Patent Application Pub. No. 2007/0128279 A1, which are herein incorporated by reference. Time-release formulations are known in the art and are described in Sawada et al. U.S. Patent Application Pub. No. 2006/0292221 A1, which is herein incorporated by reference. The following terms may be considered to be substantially equivalent to controlled release for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.). The various controlled release technologies cover a very broad spectrum of drug dosage forms. Controlled release technologies include, but are not limited to, physical systems and chemical systems.

Use as Excipient

Excipients of the present invention comprise magnesium threonate, with or without augmenting agents. The subject magnesium-counter ion compound, e.g., magnesium threonate can function as a pharmaceutically acceptable excipient. Indeed, compression of pure magnesium threonate yields tablets that retain their shape, are resistant to humidity and have an acceptable shelf life.

In some embodiments of the invention, magnesium threonate can be pressed into pill form without an excipient. In other embodiments, magnesium threonate may be combined with a pharmaceutically acceptable lubricant, such as magnesium stearate. In still other embodiments, magnesium threonate may be combined with other ingredients which affect cognitive functions and/or general health (e.g., vitamins D and E). In still other embodiments, a pill, tablet, dragee, lozenge or other acceptable pharmaceutical form may contain magnesium threonate as an excipient and be combined with another agent of choice, including, but not limited to drugs used to treat AD (e.g., cholinesterase inhibitors—Aricept, Exelon, Razadine; glutamate regulators—memantine). One of skill in the art will recognize that any number of other pharmaceuticals, nutriceuticals, supplements and other components may be added to the dosage forms herein described where magnesium threonate is used as an excipient.

Direct compression tablet manufacturing is preferred for many products in the pharmaceutical industry. It is a simple process involving less extensive equipment, operating time and cost. Microcrystalline cellulose is one example of an excipient for direct compression processing. Microcrystalline cellulose has inherently high compactibility due to its plastic deformation and limited elastic recovery. Microcrystalline cellulose usually provides for good drug dispersion, even ordered mixing with some drugs and particular grades of microcrystalline cellulose. However, the material flow properties are relatively poor for most grades of microcrystalline cellulose. Intermittent and non-uniform flow can occur as the formulation moves from the hopper to the die on a tablet press. This non-uniform flow can lead to drug content variations in the finished tableted dosage form.

In some embodiments, a wet granulation process will be utilized. The popularity of the wet granulation process as compared to the direct compression process is based on at least three potential advantages. First, wet granulation may provide the material to be compacted with a more hydrophilic nature, in order to improve the wetting, disintegration and dissolution characteristics of some hydrophobic drugs or ingredients. Second, the content uniformity and drug segregation-resistance can be enhanced using a granulation step to lock drug and excipient components together during blending. Finally, the micrometric characteristics of the component powders can be optimized prior to compaction, which is often aided by incorporation of a polymeric binder. It is normally considered that this last property imbued by wet granulation will yield a significantly more compactable product and consequently stronger, more robust tablets.

The present invention is directed in part to a novel use of magnesium threonate as a pharmaceutically acceptable excipient.

Depending upon the amount and type of drying, the concentration of the magnesium threonate in the form of a wet cake and any augmenting agents present, the compressible particles will have different particle sizes, densities, pH, moisture content, etc. One skilled in the art will appreciate that magnesium threonate may be used in combination with other excipients, including, but not limited to, lactose, microcrystalline cellulose, silicon dioxide, titanium dioxide, stearic acid, starch (corn), sodium starch clycolate, povidone, pregelatinized starch, croscarmellose, ethylcellulose, calcium phosphate (dibasic), talc, sucrose, calcium stearate, hydroxy propyl methylcellulose and shellac (and glaze).

Examples of therapeutically active agents for which improved disintegration results can be obtained include ibuprofen, aldoril, and gemfebrozil, which are relatively high dose (greater than 200 mg/dose) and water-insoluble; verapamil, maxide, diclofenac and metrolol, which are moderate-dose drug (25-200 mg/dose) and water-soluble; maproltiline, which is moderate dose (25-200 mg/dose) and water-insoluble; triazolam and minoxidil, which are relatively low dose (less than 25 mg/dose) and water-soluble. These examples are provided for discussion purposes only, and are intended to demonstrate the broad scope of applicability of the invention to a wide variety of drugs. It is not meant to limit the scope of the invention in any way.

Surfactants which may be used in the present invention as a compressibility augmenting agent generally include all pharmaceutically-acceptable surfactants. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the pharmaceutical arts, sodium lauryl sulfate has been used as an emulsifying agent in amounts of up to about 0.1% by weight of the formulation. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives. Those skilled in the art will further appreciate that the name and/or method of preparation of the surfactant utilized in the present invention is not determinative of the usefulness of the product.

Highly polar molecules may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail)

which "points away" from the cellulose surface and discourages hydrophilic surface-to-surface cellulose interactions, such as hydrogen-bonding. Preferably, the dye is one which is pharmaceutically acceptable for inclusion in solid dosage forms.

Examples of suitable dyes include Congo Red (chemical name: 3,3'4[[1,1'Biphenyl]-4,4'-diylbis-(azo)]bis[4-amino-1-naphthalenesulfonic acid]disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo) naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hydroxy-6-[7-sulfonato-4-(4-sulfonatophenylazo)-1-naphthylazo]naphthalene-1,7-disulfonate); Carmoisine (chemical name: Disodium 4-hydroxy-3-(4-sulfanato-1-naphythylazo) Naphthalene-1-sulfonate); Amaranth (chemical name: Trisodium 2-hydroxy-1-(4-sulfonato-1-naphthylazo) naphthalene-3,6-disulfonate); and mixtures thereof.

Other highly polar molecules which may be utilized as the compressibility augmenting agent include optional additional active agents themselves. For example, it is well-known to those skilled in the art that certain classes of pharmaceuticals, such as anti-psychotic drugs, are highly polar in nature and may be utilized as a compressibility augmenting agent in accordance with this invention.

The usable concentration range for the selected surfactant depends in part upon not only its molecular weight but also its degree of foaming, particularly when present in agitated slurries which will be spray dried to form the desired particulate. Thus, in those aspects of the invention where surfactants other than sodium lauryl sulfate are coprocessed with the magnesium threonate, it is to be understood that the surfactant will be present in an amount which enhances the compressibility of the magnesium threonate and yet does not have a degree of foaming which would substantially inhibit spray drying.

In an embodiment utilizing a spray-drying process, an aqueous dispersion of magnesium threonate and a compressibility augmenting agent (for example, a surfactant or silicon dioxide) is brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles may be approximately spherical in shape and may be relatively uniform in size, thereby possessing excellent flowability. The coprocessed particles are not necessarily uniform or homogeneous. Other drying techniques such as flash drying, ring drying, micron drying, tray drying, vacuum drying, radio-frequency drying, and possibly microwave drying, may also be used.

Alternatively, all or part of the excipient may be subjected to a wet granulation with an active ingredient. A representative wet granulation includes loading the novel excipient particles into a suitable granulator, such as those available from Baker-Perkins, and granulating the particles together with the active ingredient, preferably using an aqueous granulating liquid. In some embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with other excipients commonly used by those skilled in the art, depending of course upon the requirements of the particular formulation.

In other embodiments of the invention, a further material is added to the magnesium threonate and/or compressibility augmenting agent. Such additional materials include silicon dioxides, non-silicon metal oxides, starches, starch derivatives, surfactants, polyalkylene oxides, cellulose A ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, if desired, any generally accepted soluble or insoluble inert pharmaceutical filler (diluent) material can be included in the final product (e.g., a solid dosage form). Such inert pharmaceutical filler may comprise a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, microcrystalline cellulose, mixtures thereof, and the like.

An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5-3% by weight of the solid dosage form. In embodiments where a surfactant is included as part or all of the compressibility augmenting agent, an additional inclusion lubricant may not be necessary.

The complete mixture, in an amount sufficient to make a uniform batch of tablets, may then subjected to tableting in a conventional production scale tableting machine at normal compression pressures for that machine, e.g., about 1500-10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally, rectally. It is contemplated that for certain uses, e.g., antacid tablets, vaginal tablets and possibly implants, that the tablet will be larger.

The active agent(s) which may be incorporated with the novel excipient described herein into solid dosage forms invention include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrazepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the novel excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-inflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in Chemicals Used in Food Processing, pub 1274 by the National Academy of Sciences, pages 63-258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

Alternatively, the novel excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

In further embodiments of the invention, more than one compressibility augmenting agent is used. Thus, for example, two or more compressibility enhancing agents are used which provide an effect by different mechanisms.

EXAMPLES

Example 1

Preparation of Magnesium Threonate

Calcium threonate was first prepared from 264 g (1.5 mole) of vitamin C, 300 g (3 moles) of calcium carbonate, and 600 mL of 30% by volume $H_2O_2$, according to the procedure described by Wei et al., *J. Org. Chem.* 50, 3462-3467 (1985). The prepared calcium threonate was redissolved in ~3 L water at ~90° C. The resulting solution was cooled to ~50° C. and then poured through a 3 inch-diameter column packed with ~3 L clean Amberlite IR-120 strongly acidic resin, while the column was continuously eluted with water. Fractions containing threonic acid having a pH of less than about 4.5 were collected. The fractions of threonic acid were combined (~7 to ~8 L) and stirred at ~50 to ~60° C. $Mg(OH)_2$ powder was added to the threonic acid in small portions until the pH reached 7. The resulting solution was filtered and concentrated by rotary evaporation at ~50° C. to a final volume of ~700 to ~800 mL. The concentrated solution was cooled to room temperature, filtered to remove any trace amounts of insoluble materials, and then transferred to a 15-L, three-necked, round-bottom flask and mechanically stirred. About 4 L of methanol was added to the resulting solution to precipitate out a white solid product, magnesium threonate. The solid was collected by suction filtration and then dried under high vacuum at 50° C. for 2 days to yield 194 g of magnesium threonate as a white solid. Elemental analysis showed the material contained one mole of water for each mole of magnesium threonate.

Example 2

Taste Comparison

In a double-blind test, each of sixteen human volunteers, 9 males and 7 females, varying in age from 20 to 22 years was given one glass of a composition, Composition 1, comprising skim milk comprising a mixture comprising 50% by weight of magnesium gluconate, 25% by weight magnesium lactate, and 25% by weight magnesium citrate, having a 50 mM total concentration of elemental magnesium associated with the mixture, and one glass of a composition, Composition 2, comprising skim milk and magnesium gluconate, having a 50 mM total concentration of elemental magnesium associated with the magnesium gluconate. Each of the volunteers was asked to taste the two compositions and state her or his preference for one or the other or neither. A majority of subjects (87.5%) preferred Composition 1 and a minority of the subjects (12.5%) preferred Composition 2, as graphically depicted in FIG. 1.

Example 3

Enhancement of Magnesium Absorption Rate

Fifty 3-month old, male Sprague Dawley (SD) rats were divided into five groups of ten rats. Rats of this age and older are considered adult. Each of the rats was placed in a separate metabolic cage equipped with urine- and feces-collecting wells. All of the rats were maintained in a temperature-controlled room (22° C. to 25° C.) with a dark period from 08:00 pm to 08:00 am daily. From day 1 through day 3, each rat was fed daily 15 g of magnesium-free food and de-ionized water. From day 4 through day 10, each rat was fed daily 15 g of magnesium-free food and one of five different compositions, Compositions 1-4 and a Control Composition, containing 12 mM magnesium gluconate in a different medium, depending on its grouping in one of the five groups, Groups 1-4 and a Control Group. The medium was skim milk for Composition 1 and Group 1, milk prepared from powdered milk, by diluting the powdered milk with water to obtain a composition like that of skim milk, for Composition 2 and Group 2, 1% milk cream in water for Composition 3 and Group 3, water comprising 5 weight percent lactose for Composition 4 and Group 4, and water for the Control Composition and Control Group. The average volume of magnesium gluconate solution that was consumed daily was about 35 mL, corresponding to a dosage of elemental magnesium associated with the magnesium-counter ion compound ("elemental magnesium dosage"), here, magnesium gluconate, of about 10 mg/day/rat. From day 11 through day 12, each rat was fed daily 15 g of magnesium-free food and de-ionized water.

From day 4 through day 10, urine from each rat was collected daily. The collected urine from each rat was then pooled together and the total volume of the pooled urine from each rat was recorded. The pooled urine from each rat, in an amount of 500 mL, was analyzed for magnesium content using an inductively coupled plasma-atomic emission spectrometer (ICP-AES). From day 5 to day 11, feces from each rat were collected daily. The collected feces from each rat were pooled together and the pooled feces were weighed and homogenized. The pooled feces from each rat, in an amount of 0.5 g, were analyzed for magnesium content using an ICP-AES.

A formula was used to calculate a magnesium absorption rate for each rat. The formula used was $Y=AX-B$, wherein X was the average total daily magnesium intake, Y was the average net daily amount of magnesium absorbed, as calculated by X minus the average daily amount of magnesium excreted from feces, B was the average daily amount of magnesium excreted from feces when the magnesium intake was zero, and the slope A represented the magnesium absorption rate. Data points (X, Y) associated with each rat in each group of ten rats, with the exception of the best points and the worst points, were plotted. The value of A, the magnesium absorption rate, associated with each of Groups 1-4, and thus with each of the Compositions 1-4, was then obtained using linear regression. The value of A, the magnesium absorption rate, associated with the Control Group, and thus with the Control Composition, was also obtained using linear regression, and relabeled as $A_o$.

A formula was used to calculate a magnesium absorption rate enhancement percentage for each of Compositions 1-4, based on the magnesium absorption rate for each of Compositions 1-4, respectively, relative to the magnesium absorption rate for the Control Composition. The formula used was $[(A-A_o)/A_o] \times 100\%$. The magnesium absorption rates associated with each of Compositions 1-4 were all enhanced relative to that for the Control Composition, as graphically depicted in FIG. 2.

Example 4

Enhancement of Magnesium Absorption Rate

A mixture of 50% by weight magnesium gluconate, 25% by weight magnesium lactate, and 25% by weight magnesium citrate was dissolved in water to provide a control composition, Control Composition, having a 50 mM total concentration of elemental magnesium associated with the mixture. A mixture of 50% by weight magnesium gluconate, 25% by weight magnesium lactate, and 25% by weight magnesium citrate was dissolved in skim milk to provide a composition, Composition 1, having a 50 mM total concentration of elemental magnesium associated with the mixture. A magnesium absorption rate in rats was determined for each composition in the manner set forth in Example 3. The magnesium absorption rate associated with each composition is graphically depicted in FIG. 3. As shown, the magnesium absorption rate associated with Composition 1 was greater than that associated with the Control Composition.

Example 5

Magnesium Absorption Rate Comparison at Different Dosages

A comparison of magnesium absorption rate in rats, as determined in a manner set forth in Example 3, was made for three different compositions, each based on a certain magnesium-counter ion compound and a certain medium. Composition 1 was based on magnesium chloride and water; Composition 2 was based on magnesium gluconate and skim milk; and Composition 3 was based on magnesium gluconate and water comprising 5 weight percent lactose. Each of Compositions 1, 2 and 3 was prepared at two different elemental magnesium concentrations, one providing a 12 mM total concentration of elemental magnesium associated with the magnesium-counter ion compound, which corresponded to a total elemental magnesium intake or dosage of 10 mg/day/rat, and the other providing a 36 mM total concentration of elemental magnesium associated with the magnesium-counter ion compound, which corresponded to a total elemental magnesium intake or dosage of 30 mg/day/rat. A magnesium absorption rate in rats was determined for each composition at each concentration level in the manner set forth in Example 3. The magnesium absorption rate associated with each composition at each concentration level is graphically depicted in FIG. 4. As shown, the magnesium absorption rate associated with each of Compositions 2 and 3 was higher than that associated with Composition 1.

Example 6

Magnesium Absorption Rate Comparison at Different Dosages

A comparison of magnesium absorption rate in rats, as determined in a manner set forth in Example 3, was made for two different compositions, each based on a certain magnesium-counter ion composition and a certain medium. Composition 1 was based on magnesium chloride and water and Composition 2 was based on magnesium threonate and water. Each of Compositions 1 and 2 was prepared at two different elemental magnesium concentrations, one providing a 12 mM total concentration of elemental magnesium associated with the magnesium-counter ion compound, which corresponded to a total elemental magnesium intake or dosage of 10 mg/day/rat, and the other providing a 36 mM total concentration of elemental magnesium associated with the magnesium-counter ion compound, which corresponded to a total elemental magnesium intake or dosage of 30 mg/day/rat. A magnesium absorption rate in rats was determined for each composition at each concentration level in the manner set forth in Example 3. The magnesium absorption rate associated with each composition at each concentration level is graphically depicted in FIG. 5. As shown, the magnesium absorption rate associated with Composition 2 was greater than that associated with Composition 1 at each of the intake levels, more significantly so at the higher intake level.

Example 7

Measurements of Blood Magnesium Concentration

Figure 6:
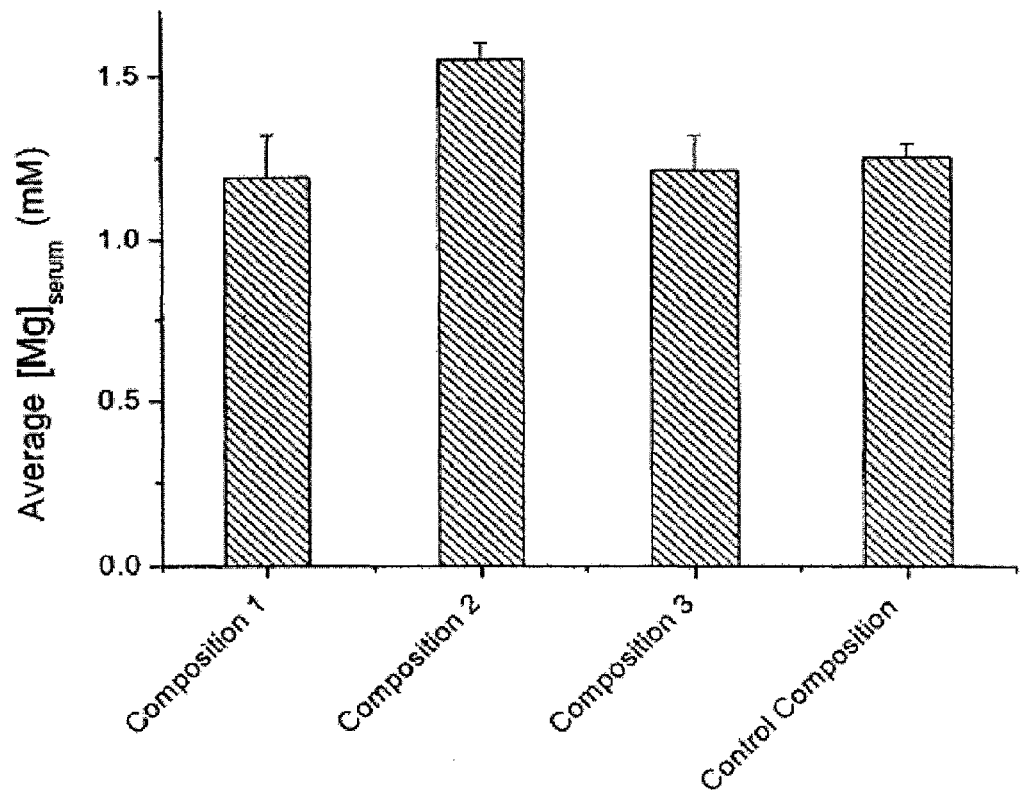
FIG. 6 is a graphical presentation of the average concentration of magnesium in serum taken from young adult rats that were exposed to a composition of magnesium chloride and water, magnesium threonate and water, or a mixture of magnesium gluconate, magnesium lactate, magnesium citrate and skim milk, or de-ionized water, as further described in Example 7.

Twelve 3-month old, male Sprague Dawley (SD) rats were divided into four groups of three rats. Each of the rats was placed in a separate metabolic cage, each of which was maintained in a temperature-controlled room (22° C. to 25° C.) with a dark period from 08:00 pm to 08:00 am daily. Each of the rats was fed daily 15 g of normal solid food and a different fluid, depending on its grouping in one of the four groups, for three days. A fluid of magnesium chloride in water, Composition 1, was used for Group 1; magnesium threonate in water, Composition 2, for Group 2; a mixture of 50 weight % magnesium gluconate, 25 weight % magnesium lactate, and 25 weight % magnesium citrate in skim milk, Composition 3, for Group 3; and de-ionized water, Control Composition, for a Control Group. Each of the fluids, other than that for the Control Group, was of 35 mM elemental magnesium associated with the subject magnesium-counter ion compound, either magnesium chloride for Group 1 or magnesium threonate for Group 2, or the mixture of magnesium-counter ion compounds for Group 3. After the three days of feeding as described above, about 200 μL of blood was taken from the retrobulbar vein of each rat. Each of the blood samples was allowed to clot at room temperature over night, then centrifuged to separate the serum from the clotting factor, and then analyzed for magnesium concentration using an inductively coupled plasma-mass spectrometer (ICP-MS). The average concentration of magnesium in the serum associated with each of Compositions 1-3 and the Control Composition, respectively, is shown in FIG. 6. As shown, the concentration of magnesium in the serum associated with Composition 2 was greater that that associated with Composition 1, Composition 2, and the Control Composition.

Example 8

Measurements of Learning Memory Capacity

A group of 10 mice that were genetically altered to present symptoms of Alzheimer's disease (AD) were fed an Mg Diet, a diet of normal solid food and a solution of magnesium threonate and water, for 30 days. The concentration of magnesium threonate in the solution was such that the consumption of a normal amount of the solution corresponded to a total intake of elemental magnesium associated with the magnesium threonate of about 3 mg/day/mouse. Another group, the control group, of 10 mice that were genetically altered to present symptoms of AD were fed a Control Diet, a diet of normal solid food and water, for 30 days.

On the final day of the 30 days of dieting, as described above, each group of mice was trained and tested according to a modified Morris water maze test (Morris et al., Nature 297, 681-683 (1982)), as now described. The pool used was a pool of water in a circular metal tank (150 cm in diameter and 50 cm in depth) having a water height of 30 cm and a water temperature that was maintained at ~22° C. The pool was placed in a moderately lit area and surrounded by a black curtain. An acrylic platform (15 cm in diameter) was placed 2 cm below the surface of the water in the middle of one quadrant of the pool, equidistant from the center and the edge of the pool. Outside the pool, a cue was placed so as to be visible to a mouse in the maze, allowing a mouse to use it as a landmark for spatial orientation. The cue remained unchanged throughout the test period.

On the first day of the training and testing period, the water in the pool was transparent, such that the platform was visible. Each mouse was trained to swim towards the platform and to stand on the platform so as not to be submerged in the pool. Each mouse underwent a trial, followed by an interval of 1 hour, followed by another trial, and so on, for a total of 5 trials. In each trial, the subject mouse was placed by hand into the pool of water at a starting or release position that was randomly selected from three possible starting positions. The mouse needed to find the platform so as not to be submerged in the pool. If the mouse found the platform, it was allowed to remain there for 30 seconds before it was returned to its home cage. The amount of time the mouse took to find the platform, referred to as "escape latency," was recorded for each trial.

On the second day of the training and testing period, a small quantity of milk was added to the water in the pool, such that the pool was opaque and the platform was no longer visible. Each mouse underwent a trial, followed by an interval of 1 hour, followed by another trial, and so on, for a total of 5 trials. Each trial was as described for the first day of the training and testing period. Once again, each subject mouse placed in the pool needed to find the platform so as not to be submerged in the pool. The amount of time the mouse took to find the platform, or escape latency, was recorded and taken as a measure of the mouse's short-term spatial memory and learning capacity. A lower escape latency measurement was associated with a better learning and memory capacity. If the mouse was unable to find the platform within 90 seconds, it was guided to and placed on the platform for 30 seconds, whereupon the trial was ended and the mouse was given a maximum escape latency score of 90 seconds for the trial.

The two groups of mice underwent further days of training and testing in the manner described above for the second day of the training and testing period. An average escape latency associated with the five trials was calculated for each group of mice for each of days 2-6 of the training and testing period. A graphical representation of these average escape latency results plotted against the associated day of the training and testing period is shown in FIG. 7B. As shown, as the days in training and testing increased, the average escape latency decreased for each group of mice. As also shown, on and after the third day of the training and testing period, the mice in the magnesium-fortified diet group outperformed the mice in the control group.

Example 9

Measurements of Improvements in Short-Term Spatial Memory Capacity

Twenty 2-month old, male Sprague Dawley (SD) rats were housed in a temperature-controlled room (22° C. to 25° C.) with a dark period from 08:00 pm to 08:00 am daily. Each of the rats was fed a daily diet of normal solid food and drinking water on a restricted feeding schedule so as to maintain 85% of its free-feeding weight. Each rat was tested according to a version of the T-maze test (Dudchenko, *Behav. Neurosci.* 115, 850-860 (2001)), involving a maze located one meter above the floor of a well-lit laboratory that contained various prominent distal extra-maze cues, which served as landmarks for the rats during the test. Over 7 days before the training and trial period began, each rat was handled and habituated to the maze and to Kellogg's Froot Loop cereal.

In an eight-day training and trial period, each rat was fed a daily diet of normal solid food and drinking water on a restricted feeding schedule so as to maintain 85% of its free-feeding weight. Each rat underwent a test of one trial, followed by an interval of 10-minutes, followed by another trial, and so on, for a total of 6 trials in one day. In each trial, each rat went through a sample run in the maze, followed by an interval of 15 seconds, followed by a choice run in the maze. In the sample run, the subject rat was forced to go to the left or to the right by the presence of a block, according to a pseudorandom sequence (with an equal number of left turns and right turns, and no more than two consecutive turns in the same direction). As a reward, Froot Loop cereal was available in the food well at the end of the run, regardless of the direction that was taken by virtue of the block. In the choice run, the block that had been present in the preceding sample run was removed, and the rat was allowed to choose to go to the left or to the right. As a reward, Froot Loop cereal was available in the food well at the end of the run, only when the rat had made a "correct choice" by choosing the direction opposite that taken in the preceding sample run. After 8 days of the training and trial period, each of the rats attained an asymptotic choice accuracy level, or number of correct choices per number of trials, of about 90%, indicating an equal capacity for task acquisition and working memory.

The rats, once trained and tested as described above, were divided into two groups of ten. One group, the control group, was fed a Control Diet, the same daily diet used in the training and trial period, which included normal solid food and drinking water on a restricted feeding schedule so as to maintain 85% of its free-feeding weight. The other group was fed an Mg Diet, the same daily diet with the exception that a solution of magnesium threonate (55 mM) in water was used in place of the drinking water, on a restricted feeding schedule so as to maintain 85% of its free-feeding weight. On average, each of the rats in the latter group drank about 30 mL of the solution daily, which corresponded to a total intake of elemental magnesium associated with the magnesium threonate of about 40 mg/day/mouse, or about 133 mg/kg body weight/day.

On the first day (designated day 0) of the feeding of the two groups, as just described, each rat underwent a preliminary test of one trial, followed by an interval of 10 minutes, followed by another trial, and so on, for a total of 4 trials in one day. In each trail, each rat went through a sample run in the T-maze described above, followed by an interval of 15 seconds, followed by a choice run in the maze. In this preliminary test, the choice accuracy level, or ratio of correct choices made, $c_o$, to the number of number of trials in the test, $n_o$, was determined for each rat. On the fifth day of feeding of the two groups, according to the feeding regime just described, each rat underwent another test, as described in connection with the preliminary test, to confirm that the rat still remembered how to complete the trials. On the following day, the sixth day (designated day 6), and on every sixth day thereafter, of feeding according to the same feeding regime, each rat underwent 4 daily trials, as described above, with the exception that an interval of 5 minutes was used in place of the interval of 15 seconds. On each day (day i) of such testing, the choice accuracy level, or ratio of correct choices made, $c_i$, to the number of trials in the test, $n_i$, were determined for each rat. Additionally, a percentage increase in the choice accuracy level relative to that determined in the preliminary test was determined for each rat, according to the formula set forth below.

$$\left(\frac{c_i/n_i - 0.5}{c_0/n_0 - 0.5} - 1\right) \times 100\%$$

The percentage increase in the choice accuracy level was taken as a measure of the rat's short-term working memory and learning capacity improvement.

An average of the percentage improvement results associated with each day of testing following the preliminary test was taken for the control group of rats and the other group of rats. A graphical representation of these averages versus the number of days on the Mg Diet or the Control Diet is shown in FIG. 7A. As shown, there was no significant difference (p-value>0.05) in the averages associated with the control group of rats and the averages associated with the other group of during the first week of testing. Thereafter, while there was not a great deal of change in the averages associated with the control group of rats, there was a significant increase in the averages associated with the latter group of rats, as demonstrated by the averages associated with day 12 through day 24 of being on the Mg Diet, with day 24 showing a 73% difference (p-value<0.05).

Example 10

Effects of Magnesium Supplementation on Recognition Memory

In this example, the effect of magnesium supplementation on recognition memory was tested. Three groups of rats were used in these experiments: 1) young rats (three months old); aging rats (12-14 months old), and; 3) magnesium-treated aging rats (12-14 months old, diet supplemented with 6 mg/kg $MgCl_2$ from 8 months of age). We used experimentally naive, female, Sprague-Dawley young (2 month old), aging (12-14 month old) and aging (22-24 month old) rats (Charles River) at the beginning of the behavior experiments. They were housed two per cage with continuous access to food and water under a 12:12 light-dark cycle, with light onset at 8:00 a.m. Mg2+ levels in CSF in control and Mg-treated rats were determined by colorimetric method with xylidyl blue (Thomas, 1998) (Anilytics Incorporated, MD). All experiments involving animals were approved by the Massachusetts Institute of Technology's and Tsinghua University Committees on Animal Care.

The three groups of rats were tested for recognition memory using an object recognition test with a single exposure to the object during training. The task is based on the natural tendency of rodents to explore new objects and tests the animals' memory capacity for distinguishing novel versus familiar objects. This type of memory exhibits age-associated decline and correlates with declines in synaptic plasticity.

Briefly, the rats were first individually habituated to the personnel and then to open-field arena during 2 weeks. The rats were then allowed to explore two identical objects placed into the arena at fixed locations until they had accumulated 30 s of total inspection time (where this is defined as active exploration, sniffing or touching the object with the nose and/or forepaws) or for a maximum of 20 min. The rat was returned to the arena for the retention test and allowed to explore for another 30 sec. The retention intervals were 10 min and 24 hours. Objects were cleaned thoroughly between trials with 20% ethanol solution to ensure the absence of olfactory cues. The particular objects for a given trial were randomly determined, but each object was used for only one trial per rat. Memory of the familiar object is associated with increased exploration of the new object and an exploration index (% correct) is calculated as new object inspection time/30.

Figure 8:
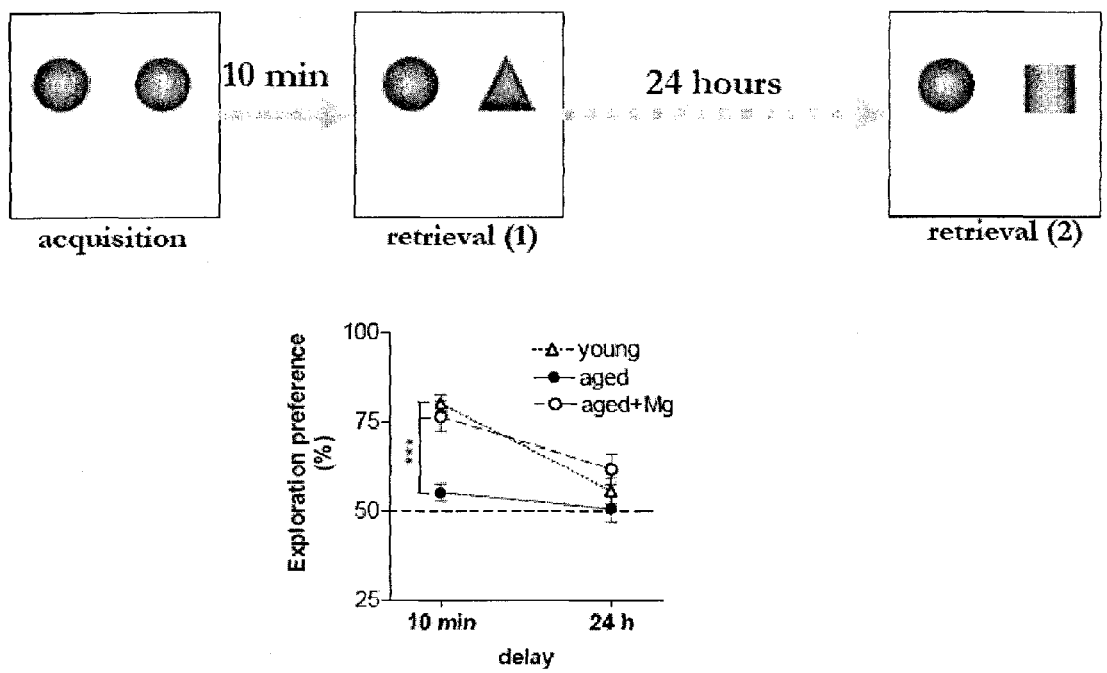
FIG. 8 is a graphical representation of experimental data showing the restorative effect of magnesium on short-term recognition memory in rats. The top portion of the figure is a graphical representation of the experimental methodology.

As shown in FIG. 8, aging rats displayed a lower novel object exploration preference at the 10 minute retention interval as compared to both young rats and aging rats supplemented with magnesium. This indicates that aging rats have a learning/memory impairment compared to young rats. These results also indicate that magnesium-treated aging rats preferentially explored the novel object to the same extent as young rats ($P<0.0001$).

After 24 hours, all groups lose there ability to distinguish novel versus familiar objects. During the training phase (5 min), both groups of aging rats showed similar total exploration time for the two objects ($P>0.4$). This indicates that a difference in exploration time could not account for the differences between magnesium-treated and untreated aging rats.

Example 11

Figure 9:
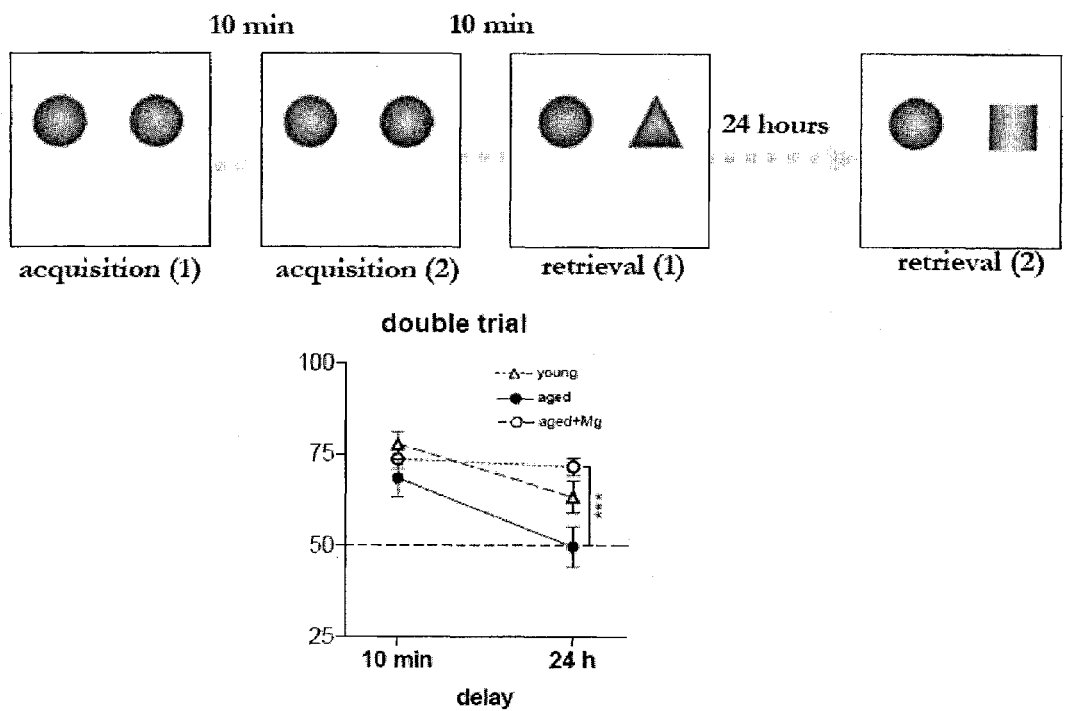
FIG. 9 is a graphical representation of experimental data showing the increase in the time course of recognition memory decline in rats given magnesium. The top portion of the figure is a graphical representation of the experimental methodology.

Effects of Liquid and Foodstuff Magnesium Supplementation on Memory Consolidation In this example, the effect of magnesium supplementation on memory consolidation was studied. We used two training sessions separated by 10 minutes, before commencing the retention tests (FIG. 9). Training, rats and magnesium supplementation were carried out essentially as in Example 10. Following spaced training, all three groups of rats (young, aging, and magnesium-supplemented aging) showed a similar preference for the novel object at the 10 min retention interval, suggesting that the aging rats were still capable of performing the task with multiple training trials. However, at the 24-hour retention interval, the untreated aging rats showed no preference for the novel object ($P<0.005$), while magnesium-treated aging rats retained a high level of preference. These results demonstrate the effectiveness of magnesium treatment in the prevention of age-dependent recognition memory decline in aging rats.

Figure 11:
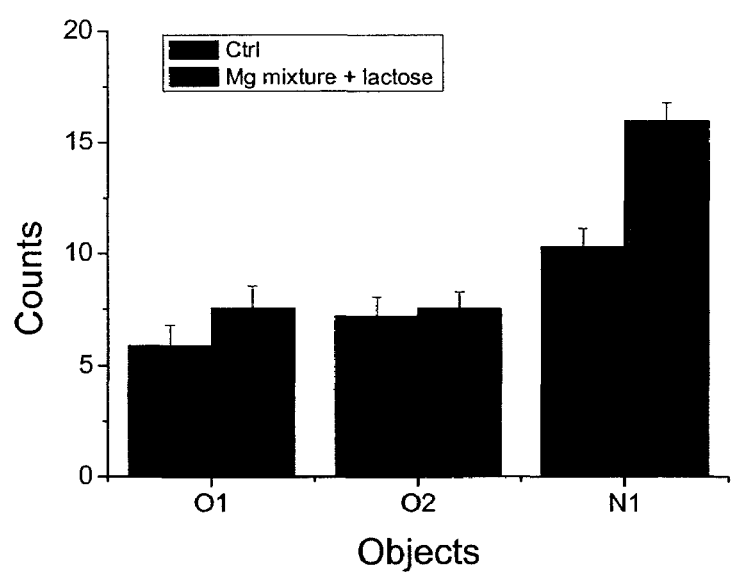
FIG. 11 is a graphical representation of experimental results enhancement of short term Memory in rats receiving a magnesium mixture and 5% lactose.

Enhancement of short term memory for rats receiving magnesium supplementation was also determined using lactose-supplemented magnesium. For these experiments, the magnesium mixture described above (magnesium gluconate, magensium lactate and magnesium citrate) and 5% lactose were added to the drinking water of rats being tested (40 mg magnesium/day). Following one week of treatment, short-term memory was determined using the novel object recognition test, essentially as described in Example 10. This experiment mimics the results of magnesium supplementation in milk as it was determined that lactose is the uptake enhancing factor in milk. Results are shown in FIG. 11. These results show that rats receiving magnesium supplementation spend more time examining the novel object, suggesting an improvement of short-term memory.

In a similar experiment, rats are fed magnesium-threonate supplemented chocolate. The rats are given unlimited access to their normal diet. Water is available at all times, except during brief testing periods. The rats are approximately 6 months old at the beginning of the experiment. A 45-mg pellet dispenser (ENV-203) is placed behind each food trough. Rats are provided access to magnesium composition supplemented chocolate pellets such that when consumed, the chocolate pellets will provide 20-40 mg of elemental magnesium per day.

Example 12

Effects of Magnesium Supplementation on Spatial Working Memory

Three groups of animals (young, aging, and magnesium-treated aging rats) were used. Animals and diets were as described in Example 10. Spatial working memory was assessed using a T-maze non-matching-to-place task. Briefly, rats were maintained on a restricted feeding schedule at 85% of their free-feeding weight. Spatial working memory was first assessed on an elevated T-maze. The maze was located 1 m above the floor in a well lit laboratory that contained various prominent distal extra-maze cues. The rats were handled and habituated to the maze for 10 days, and to Froot Loop® cereal over several days before the test. Each trial consisted of a sample run and a choice run, with delay intervals of 15 s during the training and the pattern completion tasks. On the sample run, the rats were forced either left or right by the presence of the block, according to a pseudorandom sequence (with equal numbers of left and right turns per session, and with no more than two consecutive turns in the same direction). A cereal reward was available in the food well at the end of the arm. The block was then removed, and the rat was allowed a free choice of either arm. The animal was rewarded for choosing the previously unvisited arm. Rats were run one trial at a time with an inter-trial interval of 10 min. Each daily session consisted of 6 trials.

Figure 10:
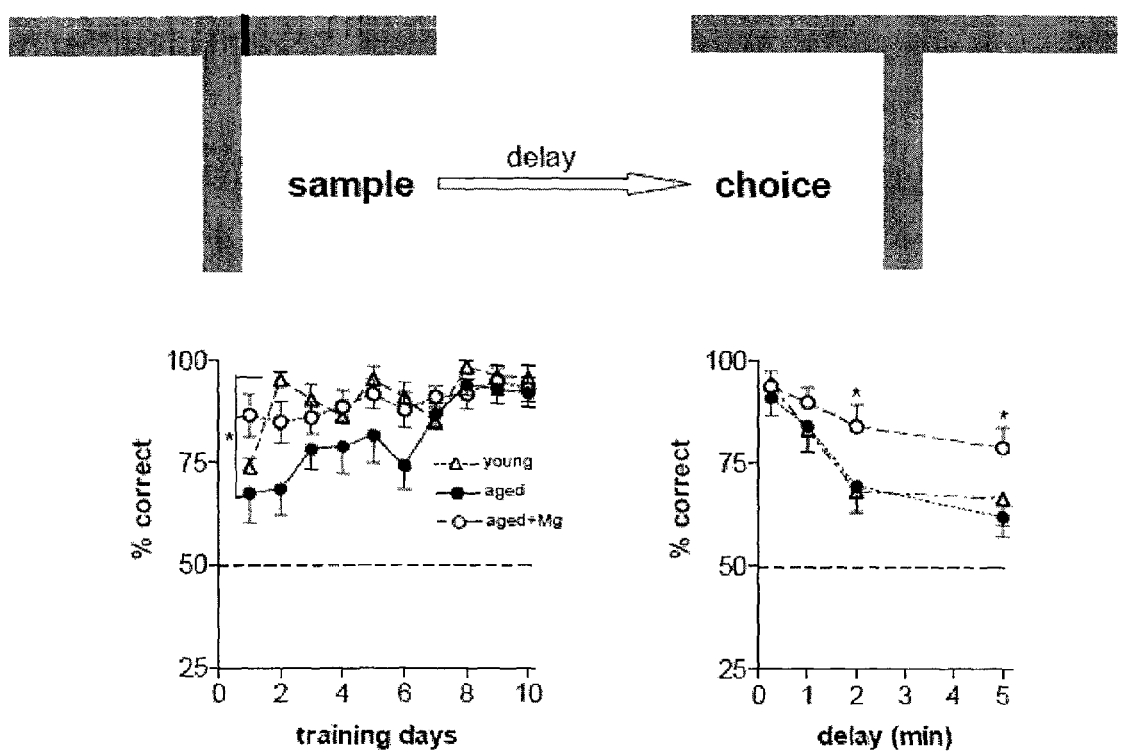
FIG. 10 is a graphical representation of results from an elevated T-maze task for young and old rats. The represented data demonstrate that magnesium improves working and short-term spatial memory in aging rats. The top portion of the figure is a graphical representation of the experimental methodology.

The rats were tested for 10 consecutive days on a rewarded forced-choice alternation task. The percentage of correct choices (alternations) was recorded for each daily session. In our experiments, the animals likely used a spatial strategy since, when the maze was rotated 180°, the animals went to the arm predicted by allocentric rather than egocentric information (data not shown). Aging rats displayed impaired learning in non-matching-to-place task as compared to young rats (FIG. 10, left panel, 15 sec delay). Magnesium-treated aging rats performed significantly better from their first trials ($p<0.05$). After 8 days of training, all three groups attained an asymptotic choice accuracy level of ~94%, suggesting an equal capacity for task acquisition. Then, spatial working memory was tested by a gradual increase of the delay between the sample and the choice trials (FIG. 10, right panel). No difference was found between young and aging rats across different delays (p>0.05), while magnesium-treatment significantly enhanced the performance of the aging rats at 2 and 5 min delays (p<0.05). Thus, although spatial working memory evaluated by T-maze did not decline with aging, magnesium-treated aging rats have enhanced spatial working and short-term memory.

Example 13

Effects of Magnesium Threonate on Learning and Memory of Aged Rats

To test whether intake of magnesium threonate leads to the improvement of working memory, learning and memory of aged (22-24 month old) rats with profound memory deficiency was examined. Twenty-four aged rats were trained to perform the elevated T maze (described in the previous example) for 10 days. Their working memory was evaluated by choice accuracy between the sample and choice trials with increasing delay. To ensure similar averaged working memory between control and magnesium-treated groups before the start of magnesium treatment, animals were randomly assigned for two groups in the end of training. Then, drinking water of rats in magnesium-treated group was supplemented with magnesium threonate (100 mg/kg/day). The effect of magnesium treatment on the rats' working memory was evaluated every six days (FIG. 7C).

The choice accuracy continuously declined in the control group during the repeated sampling. However, 12 days after beginning magnesium threonate treatment, choice accuracy associated with longer delays began to increase in the magnesium-treated group and reached to its peak on the day 24 (P<0.05, N=12). These data suggest that magnesium threonate improves working memory.

To determine whether Mg treatment triggers reversal of memory decline or general memory enhancement, we tested the efficiency of Mg treatment in young rats (2 month old). Using similar experimental procedures as those used for aged rats, the data demonstrate that magnesium threonate significantly enhanced the working memory of young rats at the 5 min delay time point compared to a control group of untreated rats with stable performance (FIG. 7C). Therefore, increasing magnesium consumption generally enhances working memory of young and aged rats.

Twenty 2-month old, male Sprague Dawley (SD) rats were housed in a temperature-controlled room (22° C. to 25° C.) with a dark period from 08:00 pm to 08:00 am daily. Each of the rats was fed a daily diet of normal solid food and drinking water on a restricted feeding schedule so as to maintain 85% of its free-feeding weight. Each rat was tested according to a version of the T-maze test (Dudchenko, Behav. Neurosci. 115, 850-860 (2001)), involving a maze located one meter above the floor of a well-lit laboratory that contained various prominent distal extra-maze cues, which served as landmarks for the rats during the test. Over 7 days before the training and trial period began, each rat was handled and habituated to the maze and to Kellogg's Froot Loop cereal.

In an eight-day training and trial period, each rat was fed a daily diet of normal solid food and drinking water on a restricted feeding schedule so as to maintain 85% of its free-feeding weight. Each rat underwent a test of one trial, followed by an interval of 10-minutes, followed by another trial, and so on, for six trials in one day. In each trial, each rat went through a sample run in the maze, followed by an interval of 15 seconds, followed by a choice run in the maze. In the sample run, the subject rat was forced to go to the left or to the right by the presence of a block, according to a pseudorandom sequence (with an equal number of left turns and right turns, and no more than two consecutive turns in the same direction). As a reward, Froot Loop cereal was available in the food well at the end of the run, regardless of the direction that was taken by virtue of the block. In the choice run, the block that had been present in the preceding sample run was removed, and the rat was allowed to choose to go to the left or to the right. As a reward, Froot Loop cereal was available in the food well at the end of the run, only when the rat had made a "correct choice" by choosing the direction opposite that taken in the preceding sample run. After 8 days of the training and trial period, each of the rats attained an asymptotic choice accuracy level, or number of correct choices per number of trials, of about 90%, indicating an equal capacity for task acquisition and working memory.

The rats, once trained and tested as described above, were divided into two groups of ten. One group, the control group, was fed a Control Diet, the same daily diet used in the training and trial period, which included normal solid food and drinking water on a restricted feeding schedule so as to maintain 85% of its free-feeding weight. The other group was fed an Mg Diet, the same daily diet with the exception that a solution of magnesium threonate (55 mM) in water was used in place of the drinking water, on a restricted feeding schedule so as to maintain 85% of its free-feeding weight. On average, each of the rats in the latter group drank about 30 ml of the solution daily, which corresponded to a total intake of elemental magnesium associated with the magnesium threonate of about 40 mg/day/mouse, or about 133 mg/kg body weight/day.

On the first day (designated day 0) of the feeding of the two groups, as just described, each rat underwent a preliminary test of one trial, followed by an interval of 10 minutes, followed by another trial, and so on, for a total of four trials in one day. In each trail, each rat went through a sample run in the T-maze described above, followed by an interval of 5 minutes, followed by a choice run in the maze. On the fifth day of feeding of the two groups, according to the feeding regime just described, each rat underwent another test, as described in connection with the preliminary test, to confirm that the rat still remembered how to complete the trials. On the following day, the sixth day (designated day 6), and on every sixth day thereafter, of feeding according to the same feeding regime, each rat underwent 4 daily trials, as described above. On each day (day i) of such testing, the choice accuracy level, or ratio of correct choices made to the number of trials in the test, were determined for each rat.

An average of the percentage choice accuracy associated with each day of testing following the preliminary test was taken for the control group of rats and the Mg treated group of rats. The difference between two groups versus the number of days on the magnesium Diet or the Control Diet is shown in FIG. 7A. As shown, there was a significant increase in the averages associated with the magnesium treated group of rats, starting around day 12 through day 24 of being on the Mg Diet, with day 24 showing a 25% increase (p-value<0.05). Similar phenomena occur in aged animal (17 month old) under magnesium treatment (FIG. 7C).

Example 14

Effects of Magnesium Threonate on Working Memory

Having demonstrated the enhancement of working memory by magnesium treatment, further experiments were conducted to determine whether magnesium threonate led to the improvement of long-term memory in young and aged rats using the Morris water maze. For these experiments, drinking water was supplemented with magnesium threonate (100 mg/kg/day) in the magnesium-treated groups. Briefly, the Morris water maze task was used to study spatial learning and memory after distinct difference in T-maze working memory test was observed, and the method is as described previously, with minor modifications. The pool was a circular metal tank, 150 cm in diameter, 50 cm deep, filled to a height of 30 cm with water. Water temperature was maintained at ~22° C. An acrylic platform (15 cm in diameter) was placed inside the pool, its upper surface 2 cm below the surface of the water, so that a rat inside the pool would be unable to locate it visually. The pool was set in a moderately lit, circular enclosure made with black curtain, in which there were several cues (two for young rats and four for old rats) with different sharp and color external to the maze. These were visible from within the pool and could be used by the rat for spatial orientation. These cues remained unchanged throughout the testing period.

The young rats undergo 8 trials training with an inter-trial interval of 1 hour for one day. For old rats, the training session was split into two days, 5 trials for day 1 and 3 trials for day 2, and the inter-trial interval is also 1 hour. Each rat was placed into the water by hand, so that it faced the wall of the pool, at one of three starting positions. The sequence of these positions was randomly selected. The platform was set in the middle of one quadrant, equidistant from the center and the edge of the pool. If the rat found the platform, it was allowed to remain there for 30 s and was then returned to its home cage. If the rat was unable to find the platform within 90 s, it was guided to and placed on the platform for 30 s, the trial was terminated and the maximum score of 90 s was given. In each trial, the goal latency to the hidden platform was recorded using a video system, Ethovision (Nadolus).

The probe trial (also the memory retention test) was carried out 1 hour (first probe trial) and 24 hours (second probe trial) after the last trial of the training session. In the probe trial, the platform was removed and each rat was put into the pool for 30 s. The total time spent in the target quadrant (where the platform had been located during the training trials), as well as the swimming speed, was measured using the same video system.

After finishing the probe trial, the rats receive partial cue test to access their ability to retrieve memories on the basis of incomplete information. First rats received re-training in which the platform was put back in the same location compared with the training session. After the rats remembered the location of platform, the cues were adjusted that only one cue was remained in the experiment system, and the escape latency of rats in this circumstance was recorded. Then, a full-cue test was carried and the escape latency was recorded.

Figure 12:
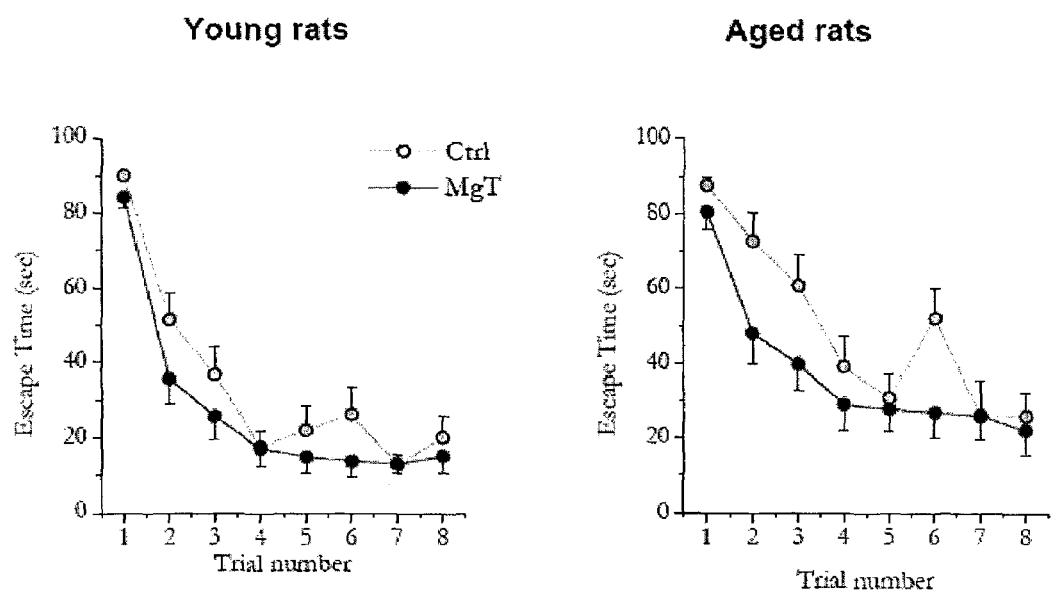
FIG. 12 is a graphical representation of experimental results from a water maze test conducted on young and aged rats. The represented data show that magnesium threonate supplementation leads to enhancement of learning and long-term memory in both young and aged rats.

For these experiments, rats and diets were essentially the same as described in Example 13. During the training period, the performance of control and magnesium threonate-treated rats gradually improved in both young and aged groups (FIG. 12). However, magnesium-treated rats learned faster than control rats (ANOVA test, young: F (7, 215)=17.07, p<0.001, n=15; aged: F(7,215)=17.11, p<0.001, n=15).

Figure 13:
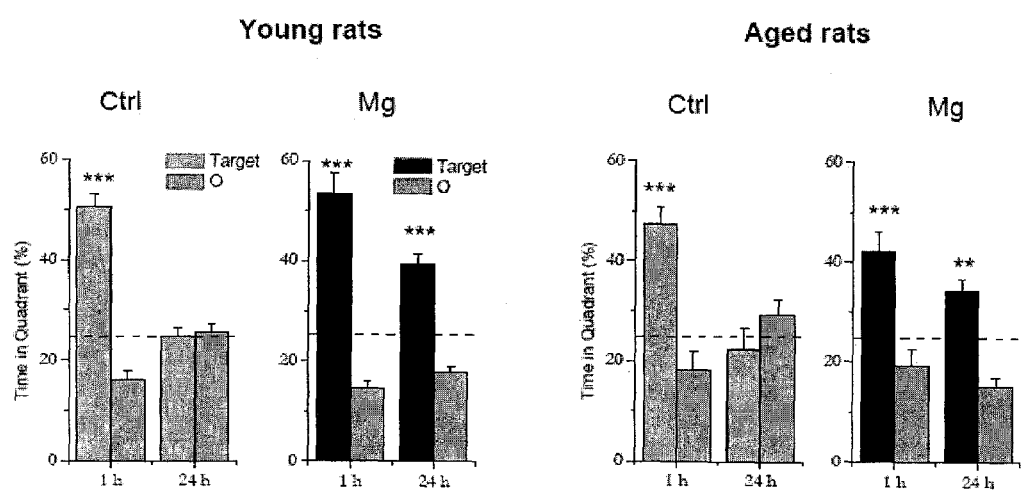
FIG. 13 is a graphical representation of the results of a memory test conducted on young and aged rats. The data demonstrates that magnesium supplementation enhance memory in both populations.

In the probe tests performed 1 hour after the end of the training (when the platform was removed and the rats were allowed to search for 60 seconds), all four groups of rats (young, magnesium-treated young, aged, magnesium-treated aged) showed preference for the training quadrant (young, FIG. 13, left panel, p<0.001; aged, FIG. 13, right panel, p<0.001), suggesting that young and aged groups are able to equally memorize the location of the platform.

To test the rats' long-term spatial memory, the probe tests were delayed 24 hours after the training. The control rats in both young and aged groups lost their preference for the training quadrant (p>0.25), while magnesium-treated young (FIG. 13, left panel) and aged (FIG. 13, right panel) rats retained their quadrant preference (young rats: p<0.001; aged rats: p<0.01). Vision and locomotor functions were equally efficient in both group of rats, judging by swimming speed and latency of escape to a visible platform (young rats: p=0.83; aged rats: p=0.84). Thus, these results demonstrate that magnesium threonate significantly enhances hippocampus-dependent learning and memory in both young and aged rats.

Figure 14:
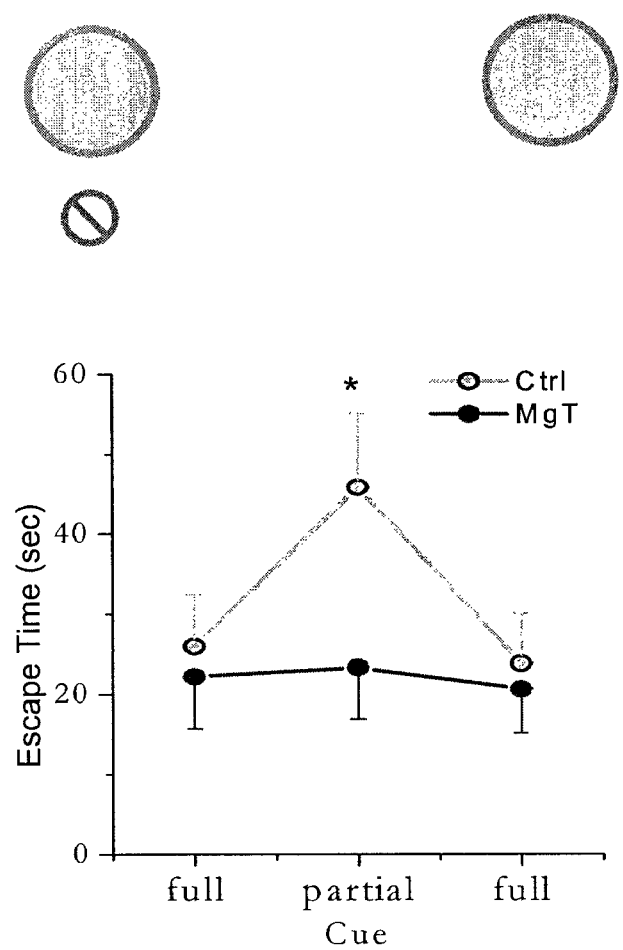
FIG. 14 is a graphical representation of experimental results from pattern completion tests conducted on aged rats. The data demonstrates the effects of magnesium threonate on the memory process. The top portion of the figure is a graphical representation of the experimental methodology.

Another crucial function of biological memory systems exhibiting profound decline during aging is pattern completion—the ability to retrieve memories on the basis of incomplete information. We studied the dependence of spatial memory recall on the integrity of distal cues during water maze test. The pattern completion experiments were performed with aged rats that underwent the training period in water maze (FIG. 14). Magnesium-treated aged rats performed better under partial-cue conditions than control aged rats in water maze (FIG. 14). Magnesium-treated rats had similar escape latency at full-cue and at partial-cue conditions in water maze (p=0.75), whereas the escape latency of control aged rats increased significantly under partial-cue condition (FIG. 14, p<0.05). These results indicate that magnesium threonate treatment is effective for improving memory recall in aged rats.

Example 15

Effects of Magnesium Threonate in a Mouse Alzheimer's Disease (AD) Model

In this example, the potential for treatment of AD with magnesium threonate was analyzed. For these experiments, [insert mouse strain parameters—include control, 6 month/13 month, —here] were utilized. AD mice were given 3 mg/per day of elementary magnesium in form of magnesium threonate (MgT). For these experiments, mice were tested using the Morris water maze test, essentially as described in the previous example. Results are shown in FIG. 15.

Figure 15:
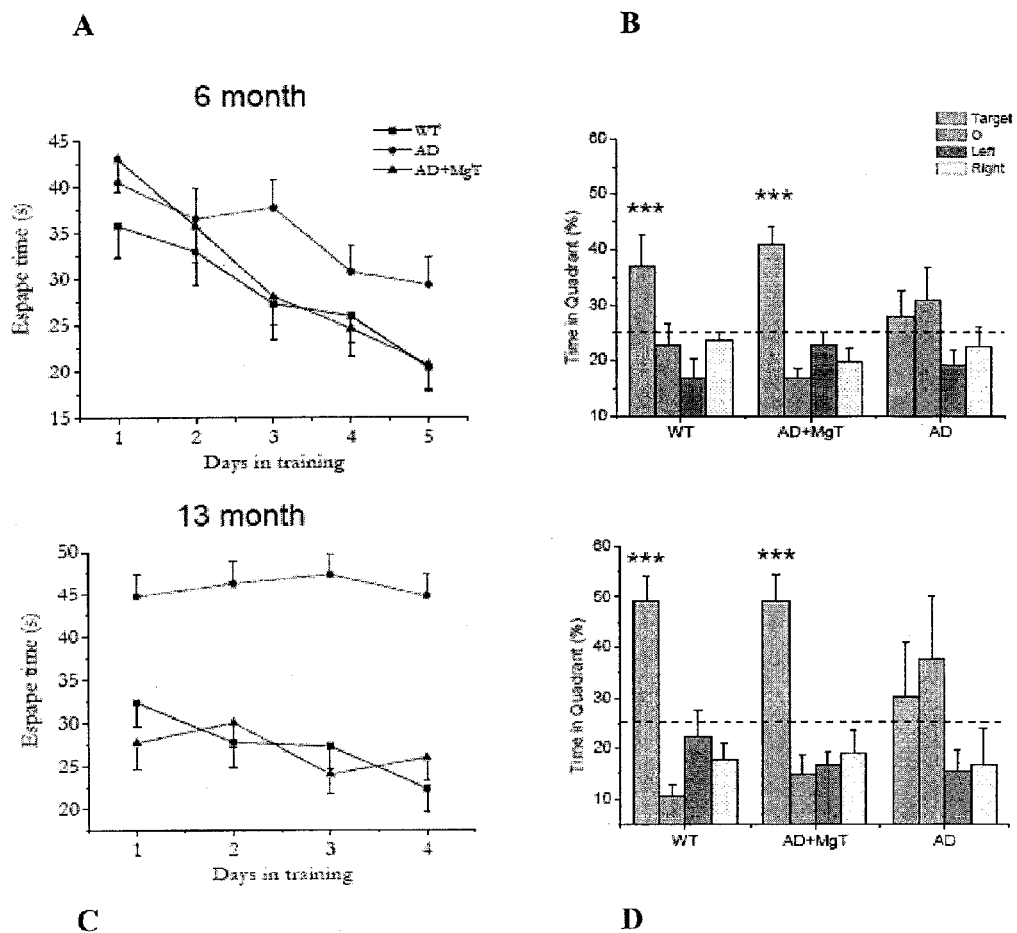
FIG. 15 is a graphical representation of the effects of magnesium threonate on the memory process in a mouse model of Alzheimer's Disease (AD). The data demonstrates that both learning (panels A and C) and memory (panels B and D) at both 6 and 13 months are improved when AD mice are given magnesium threonate.

During the training period, the performance of control, AD and magnesium threonate-treated AD mice gradually improved in young mice (FIG. 15, panel A). However, young AD mice treated with MgT showed a similar learning progression to control mice. Aged AD mice showed no improvement during the training period, however, control and MgT-treated AD mice did show improvement during the training period (FIG. 15, panel C). This demonstrates that MgT is effective in counteracting the effects of AD during the learning process in both young and old mice.

Young control mice, young MgT-treated AD mice, aged control mice and aged MgT-treated AD mice showed preference for the training quadrant (FIG. 15, panels B and D). These results show several things. First, the results suggest that young and aged groups are able to equally memorize the location of the platform. Second, the results demonstrate that MgT treatment is able to counteract the effects of AD on long-term spatial memory.

Example 16

Comparison of Magnesium Threonate with Anti-AD drugs

Figure 16:
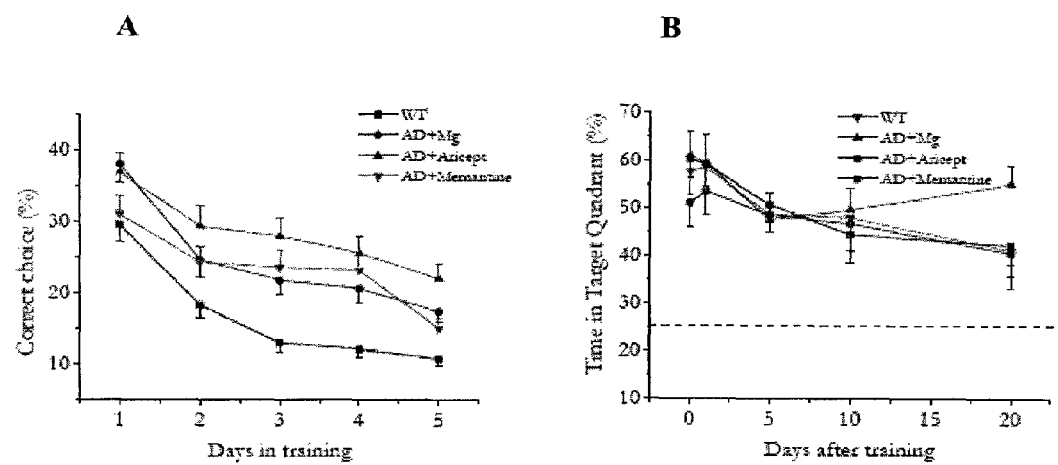
FIG. 16 is a graphical representation of the results from a learning (panel A) and memory (panel B) comparison of magnesium threonate treatment with drugs aricept or memantine used to treat AD.

Having demonstrated the effectiveness of MgT treatment in counteracting the effects of AD, a comparison with other anti-AD drugs was performed. In this example, the effectiveness of magnesium threonate in treating AD was compared to the effectiveness of other anti-AD drugs. For these experiments, the mice (aged 13 months) and magnesium threonate supplementation were essentially as described in Example 14. Two known anti-AD drugs named aricept and memantine were administered separately to the mice. For these experiments, mice were tested for effects on memory and learning using the Morris water maze test, essentially as described in the previous example. Results are shown in FIG. 16.

Initially, there was little difference between WT and AD mice receiving treatment with any of the test compounds. However, AD mice treated with MgT and memantine showed similar effects, both being better at reducing the effects of AD on learning capacity than aricept (FIG. 16, panels A and B).

Example 17

Correlation Between Short-Term Memory and Magnesium Intake in Aged Rats

In this example, the effect of magnesium supplementation on recognition memory was tested in aging rats (12-14 months old). We used experimentally naive, male, Sprague-Dawley rats (Charles River) at the beginning of the behavior experiments. They were housed two per cage with continuous access to food and water under a 12:12 light-dark cycle, with light onset at 8:00 a.m. The total magnesium intake/rat was determined by adding the sum of magnesium from food and magnesium supplement (Mg threonate) in their drinking water.

The rats were tested for recognition memory using an object recognition test with a single exposure to the object during training. The task is based on the natural tendency of rodents to explore new objects and tests the animals' memory capacity for distinguishing novel versus familiar objects. This type of memory exhibits age-associated decline and correlates with declines in synaptic plasticity.

Briefly, the rats were first individually habituated to the personnel and then to open-field arena during 2 weeks. The rats were then allowed to explore two identical objects placed into the arena at fixed locations until they had accumulated 30 s of total inspection time (where this is defined as active exploration, sniffing or touching the object with the nose and for forepaws) or for a maximum of 20 min. The rat was returned to the arena for the retention test and allowed to explore for another 30 sec. The retention intervals were 10 min for short-term memory test. Objects were cleaned thoroughly between trials with 20% ethanol solution to ensure the absence of olfactory cues. The particular objects for a given trial were randomly determined, but each object was used for only one trial per rat. Memory of the familiar object is associated with increased exploration of the new object.

Figure 19:
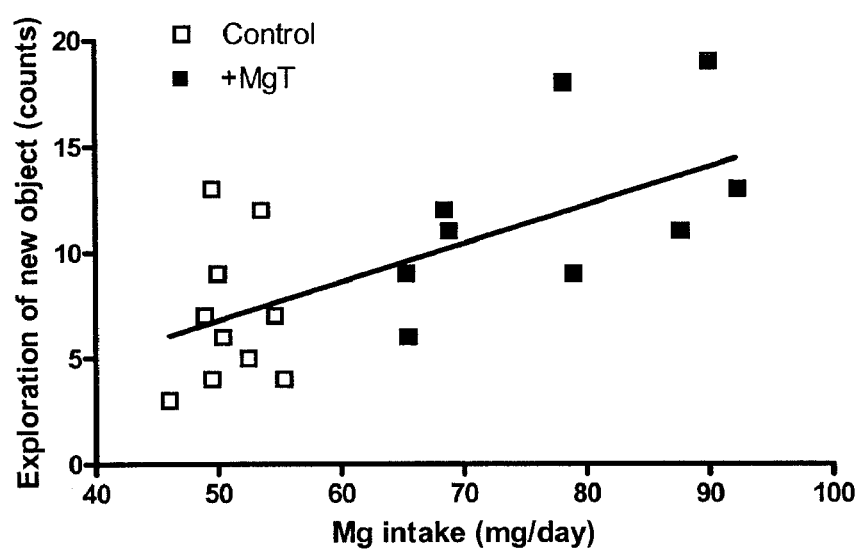
FIG. 19 is a graphical representation of the correlation of magnesium intake and short-term memory effects.

As shown in FIG. 19, in comparison with rat in control group (denoted by open squares; n=10) the animal with Mg compound treatment (denoted by filled squares; n=9) show higher exploration preference to novel object, suggesting the improvement of their short-term memory. More importantly, the degree of improvement is strongly correlated with the amount of Mg supplement they intake (p<0.01). This experiment clearly shows that animals with higher total magnesium intake have better short-term memory.

Example 18

Figure 20:
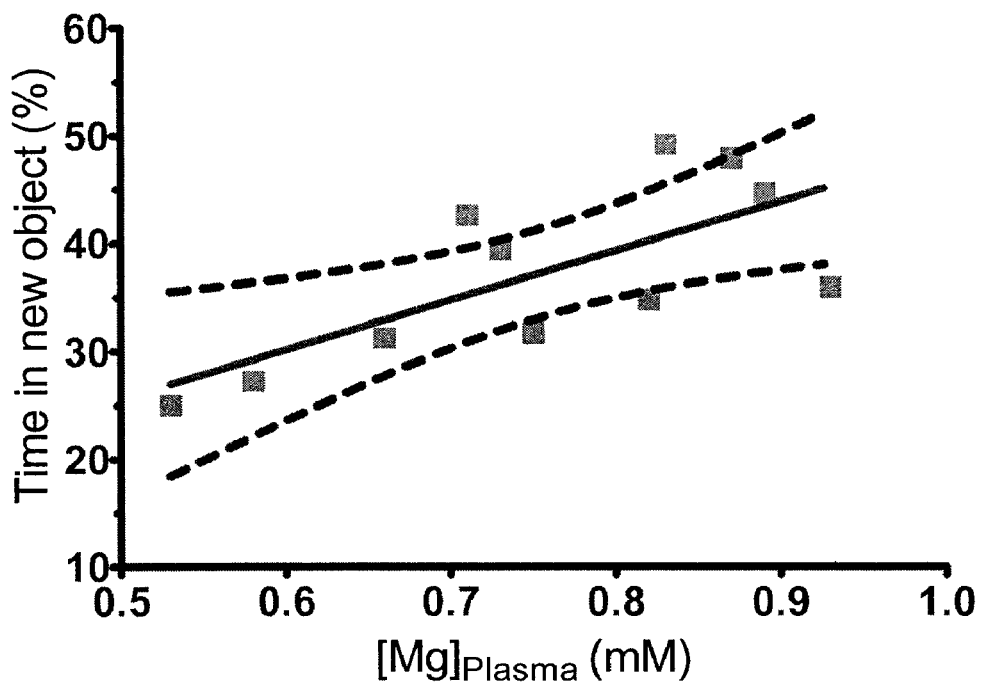
FIG. 20 is a graphical representation of the correlation of plasma concentration of magnesium and short-term memory effects.

Correlation Between Short-Term Memory and Plasma Magnesium Concentration in AD Mice In this example, the correlation between short-term memory and plasma magnesium concentration in AD mice was determined. The novel object recognition test was used to evaluate the short-term memory of AD mice receiving magnesium treatment. The experimental procedure is similar to what described in Example 16 except that four objects were used (three old and one new) in each test. The exploration preference to novel object in AD mice is linearly correlated with their plasma Magnesium values (n=11, p<0.05). Results are shown in FIG. 20.

The significance of Examples 16 and 17 is that for the first time we established that cognitive function improvement is linearly correlated to magnesium intake, which is, in turn, linearly correlated to blood magnesium level. These results are unexpected as it was equally reasonable to expect that only when magnesium intake or blood magnesium levels reach a certain threshold level can cognitive function be improved. Furthermore, without these discoveries, one of ordinary skill would not know to what extent an animal's cognitive function can be improved. Our data suggest that magnesium intake should be as high as practical as long as the intake does not cause diarrhea and the blood magnesium level does not exceed the upper limit of the normal blood magnesium distribution range (i.e., induce hypermagnesia effects). Thus, we here present the foundations for determining the optimal dosage range and regimen for any suitable magnesium compound which maintains blood magnesium concentrations at the high end of the normal blood magnesium distribution range for a given animal species.

Example 19

Correlation Between Physical Motility of AD Mice in a Dose-Dependent Fashion

Figure 21:
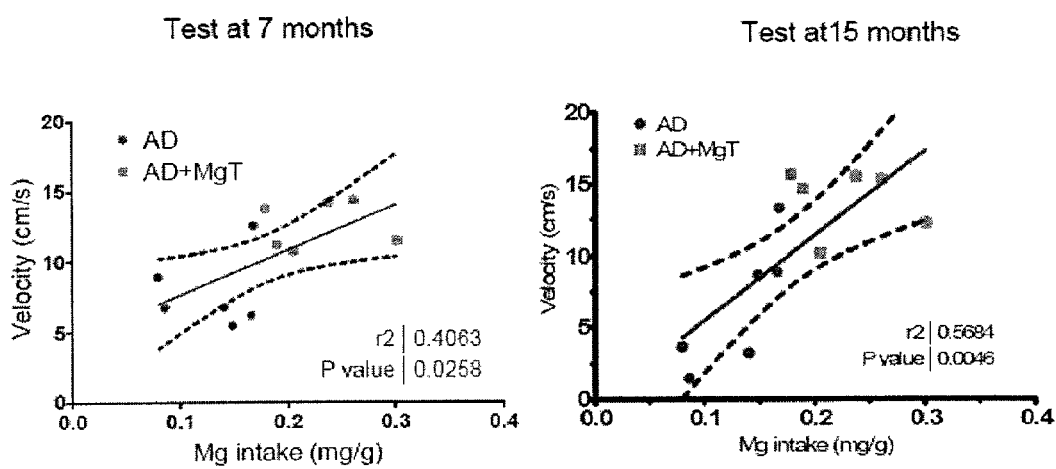
FIG. 21 is a graphical representation of the correlation between magnesium intake and increased motility in mice with and without AD at both 7 months and 15 months.

In this example, we demonstrate the correlation between physical motility of AD mice in a dose-dependent fashion. The movement of mice during water maze test (similar to the test described in Example 8 above) was monitored with video camera. The swimming speed of each mice is calculated from off-analysis. Results are shown in FIG. 21. As can be seen from these results, magnesium treatment of AD mice following 7 months of treatment (FIG. 21, left panel) and 15 months of treatment (FIG. 21, right panel) resulted in greatly increased mobility during the water maze test.

Example 20

Sustained Improvement of Learning and Memory Functions of AD Mice Receiving Magnesium Supplementation In this example, the ability of magnesium supplementation to sustain improvement of learning and memory functions of AD mice. A group of 10 mice that were genetically altered to present symptoms of Alzheimer's disease (AD) were fed a Magnesium Diet (a diet of normal solid food and a solution of magnesium threonate and water). The concentration of magnesium threonate in the solution was such that the consumption of a normal amount of the solution corresponded to a total intake of elemental magnesium associated with the magnesium threonate of about 3 mg/day/mouse. Another group, the control group, of 10 mice that were genetically altered to present symptoms of AD was fed a Control Diet, (a diet of no-1 solid food and water).

On the final day of the 60 days on the described diets, each group of mice was trained and tested according to a modified Morris water maze test (Morris et al., *Nature* 297, 681-683 (1982)), as now described. The pool used was a pool of water in a circular metal tank (150 cm in diameter and 50 cm in depth) having a water height of 30 cm and a water temperature that was maintained at 22° C. The pool was placed in a moderately lit area and surrounded by a black curtain. An acrylic platform (15 cm in diameter) was placed 2 cm below the surface of the water in the middle of one quadrant of the pool, equidistant from the center and the edge of the pool. Outside the pool, cues were placed so as to be visible to a mouse in the maze, allowing a mouse to use it as a landmark for spatial orientation. The cues remained unchanged throughout the test period.

On the first day of the training and testing period, the water in the pool was transparent, such that the platform was visible. Each mouse was trained to swim towards the platform and to stand on the platform so as not to be submerged in the pool. Each mouse underwent a trial, followed by an interval of 1 hour, followed by another trial, and so on, for five trials. In each trial, the subject mouse was placed by hand into the pool of water at a starting or release position that was randomly selected from three possible starting positions. The mouse needed to find the platform so as not to be submerged in the pool. If the mouse found the platform, it was allowed to remain there for 30 seconds before it was returned to its home cage. The amount of time the mouse took to find the platform, referred to as "escape latency," was recorded for each trial. On the second day of the training and testing period, a small quantity of milk was added to the water in the pool, such that the pool was opaque and the platform was no longer visible. Each mouse underwent a trial, followed by an interval of 1 hour, followed by another trial, and so on, for five trials. Each trial was as described for the first day of the training and testing period. Once again, each subject mouse placed in the pool needed to find the platform so as not to be submerged in the pool. The amount of time the mouse took to find the platform, or escape latency, was recorded and taken as a measure of the mouse's short-term spatial memory and learning capacity. A lower escape latency measurement was associated with a better learning and memory capacity. If the mouse was unable to find the platform within 90 seconds, it was guided to and placed on the platform for 30 seconds, whereupon the trial was ended and the mouse was given a maximum escape latency score of 90 seconds for the trial.

The two groups of mice underwent further days of training and testing in the manner described above for the second day of the training and testing period. An average escape latency associated with the five trials was calculated for each group of mice for each of days 2-6 of the training and testing period. A graphical representation of these average escape latency results plotted against the associated day of the training and testing period is shown in FIG. 15 (panels A and C). As shown, as the days in training and testing increased, the average escape latency decreased for each group of mice. As also shown, on and after the third day of the training and testing period, the mice in the magnesium-fortified diet group outperformed the mice in the control group.

To check the long effects of magnesium compound treatment, the AD mice in magnesium treated were under Magnesium diet continuously. The learning capabilities of three of mice were evaluated using the water maze test 10 months after beginning the diet. AD mice fail to find the hidden platform completely, while wild type mice and AD mice under magnesium treatment can still find the location of hidden platform quickly (data not shown). These results show that magnesium treatment is still effective after long-term treatment.

Finally, even after 15 month of magnesium treatment (via the diets described above), the short-term memory of AD mice (measured using a novel object recognition test as described above) were still as good as the wild type control mice, while the AD mice without magnesium treatment have very poor short-term memory (data not shown).

Example 21

Ameliorative Effects of Magnesium Supplementation on Depression

In this example, a forced swimming test (FST) was used to evaluate anti-depression effects of Magnesium compound. FST is the most widely used tool for assessing antidepressant activity preclinically. The test follows the method described by Porsolt et al., Nature, 266: 730-2 (1977) with a little modification to increase its sensitivity (Cryan et al., Trends Pharmacol. Sci., 23:238-45 (2002)). Animals were individually placed into glass cylinders (50 cm height; 20 cm diameter) containing 40 cm of water at 22° C. After 15 min, they were transferred to a 30° C. drying environment for 30 min (the pre-test phase). The animals were returned to the cylinder 24 h later for 5 min (the test phase), and this session was recorded with a video camera. Fresh water was used for each rat and the cylinder was cleaned. Experiments were performed between 10:00 a.m. and 3:00 p.m. Observation of the videotapes was performed by an experimenter unaware of the treatment received by the animals and immobility time measured. A rat was considered immobile when floating and making only the necessary movements to keep its nostrils above the water surface. Additionally, animals behavior during test phase was divided into swimming, climbing and immobility during 5 sec intervals, then data were analyzed as described (Cryan et al., 2002).

Figure 22:
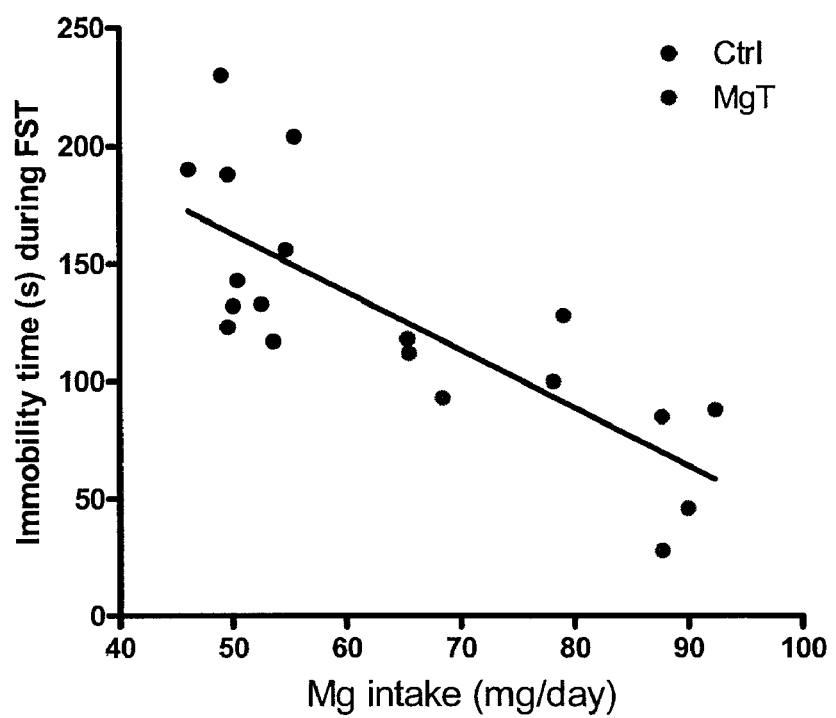
FIG. 22 is a graphical representation of the antidepressant effects of magnesium.

A significant reduction in immobility of animals treated with magnesium threonate in comparison with controls was observed after chronic magnesium threonate consumption. Interestingly, the immobility time of magnesium threonate-treated animals significantly correlated with magnesium threonate intake (FIG. 22). These results show that, like the effect on cognitive function, magnesium has antidepressant effect also in a dose-pendent fashion. The result suggests that the optimal dosage range and regimen for a magnesium compound to enhance cognitive function are equally applicable to utilization of magnesium as an antidepressant.

Example 22

Increased Lifespan of *Drosophila* Receiving Magnesium Threonate

Figure 23:
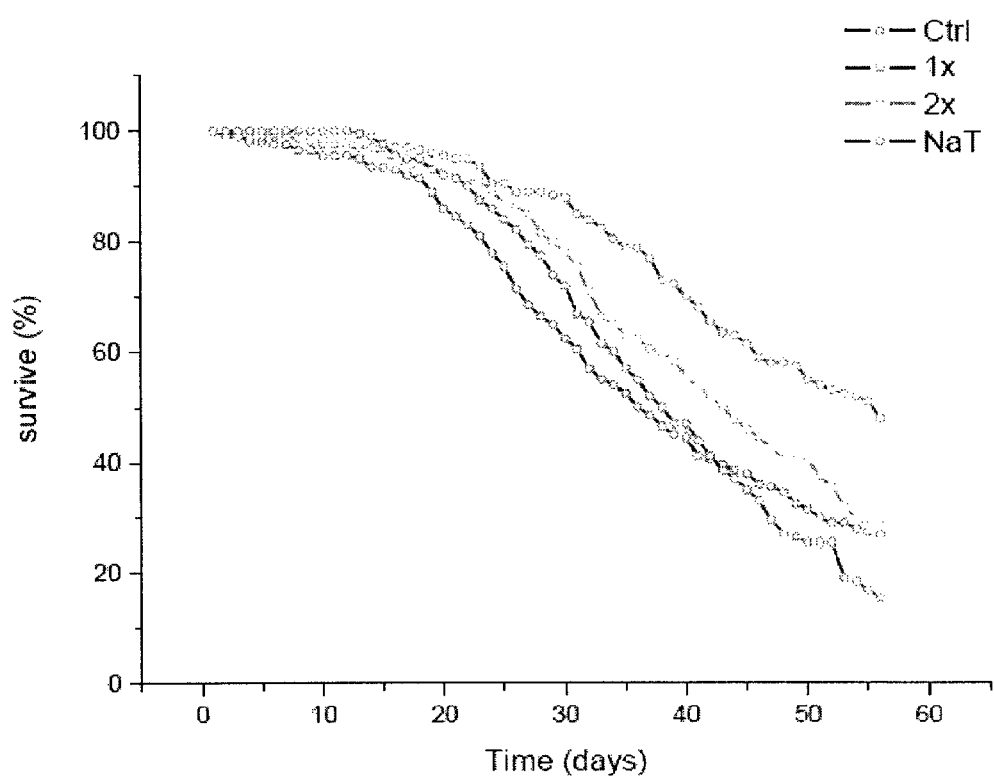
FIG. 23 is a graphical representation of the effect of magnesium on the lifespan of *Drosophila*.
Figure 24:
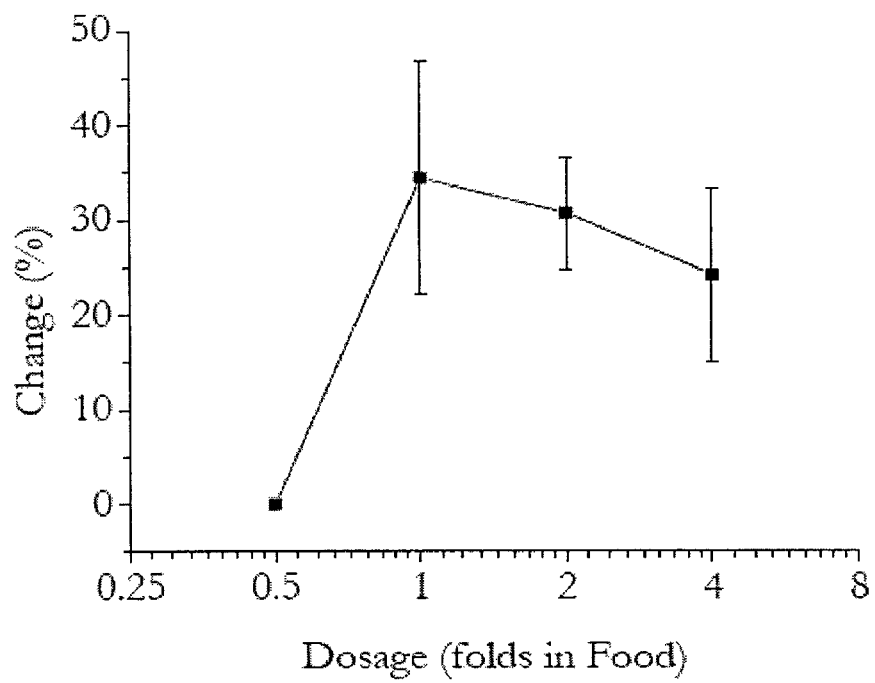
FIG. 24 is a graphical representation of the correlation between lifespan increase and magnesium intake in *Drosophila*.

To examine the effect of magnesium on an animal's lifespan, two standard laboratory inbred strains of *Drosophila*, 2 U and Canton S (CS) wild-type flies, were fed magnesium threonate (MgT). The flies were reared in bottles or vials maintained at 25° C. and 65% humidity on a 12-hour light/12-hour dark cycle. The 2 U line was reared in Cold Spring Harbor's standard laboratory fly medium. The CS line was reared in standard density culture on standard laboratory fly medium. The Magnesium-supplemented media were prepared by adding MgT to vigorously stirred normal molten media at 70° C. The final concentration of MgT in food for the 2 U line was 80, 160, 240 and 400 ug/g, respectively, while the final concentration of compound in food for the CS line was 100, 200, 300 and 500 ug/g, respectively. The flies were initially reared in 30 mL-sized transparent plastic bottles containing 4 mL food media. Newborn flies on the day of eclosion were transferred to medium containing different concentration of MgT for 2 days for mating. After that, male and female flies were transferred to vials (20/vial) under light CO2 anesthesia. There were around 200 flies in each treatment. Flies were transferred to vials containing fresh medium every 2 days and deaths were scored daily. Data were plotted either as survival rate vs. time (FIG. 23) or as percent lifespan change vs. fold in the amount of Magnesium increase in food (FIG. 24) from multiple trials.

The results suggest that the benefit of magnesium supplementation is not limited to cognitive function—it improves the overall health of the animal. It also suggests that there exists an optimal magnesium dosage range. Too high a dosage or a body magnesium level may diminish the benefit or even cause harm. Thus, this data also provides further support for establishing the optimal range of supplementation that yields health benefits.

Example 23

Measuring Plasma, Serum or Urine Magnesium Concentration

In this example, we develop a new method for determining physiological concentrations of magnesium. The data discussed above demonstrates that a relatively high body magnesium level is important for maximal health benefit, but too high a magnesium level may be harmful. Therefore, it is desirable for an individual to take the right amount of a magnesium supplement so that the desired body magnesium level is achieved. To do this, two requirements need to be met. The first is a reliable way of assessing body magnesium level. The second is an efficient and controllable magnesium supplementation technique. Here we disclose the method derived from the data we have collected, which provided the information allowing us to achieve both requirements.

We have discovered that following a meal, the blood magnesium level (such as $[Mg]_{plasma}$) rises rapidly, reaching a peak and then falling back to a baseline level. It is the baseline level blood magnesium concentration ("basal [Mg]") that is indicative of body magnesium status. The magnesium concentration at or near the peak is highly variable, depending on the amount and type of food ingested. Thus, if the blood magnesium is measured following a meal, the value is likely to be too high and variable in nature. Most clinical guidelines for measuring blood magnesium state that it is not necessary to fast before a blood sample is taken. This may at least partly explain the wide disparity in the reported normal ranges of blood magnesium concentration for both healthy and unhealthy subjects.

The significance of our finding is two fold. First, basal blood magnesium concentration measured after 12 hour fasting is more reflective of the true body magnesium status. Second, magnesium supplementation should be preferably taken between meals, and most preferably taken before bedtime. The supplement is preferably a liquid form, or more preferably a slow-release solid form. The underlying reason is that when blood magnesium concentration peaks, most magnesium is excreted in the urine via the kidneys. Thus, it is preferable to stagger the meal times and supplementation times so that a more sustained blood magnesium concentration is achieved, allowing more time for blood magnesium to distribute to tissues. Even more preferably, the magnesium supplementation is taken at bedtime Body magnesium status may be assessed in one of many ways or in a combination of several ways. Other body Magnesium status indicators and detection methods include the following: 1) intracellular ionized magnesium in red blood cells; 2) bone magnesium content; 3) magnesium concentration in the cerebrospinal fluid; 4) sublingual magnesium assay (e.g., use of the 'Exatest' is a test used, for example, during cardiac surgery to determine cellular magnesium levels.); 5) intracellular free magnesium; and 6) nuclear magnetic resonance (NMR) spectroscopy. See Buchli and Duc, Magn. Reson. Med. 32:47-52 (1994).

For this example, Calmagite, a $Mg^{2+}$ chelating dye, was used for measuring $[Mg]_{plasma}$ and $[Mg]_{urine}$ in an alkaline (pH>11) solution (See, e.g., Khayam-Bashi, et al., Clin. Chem. 23: 289-91 (1977); Abernethy and Fowler, Clin. Chem. 28: 520-22 (1982); and Liedtke and Kroon, Clin. Chem. 30: 1801-4 (1984)). Upon binding to $Mg^{2+}$, the blue colored dye Calmagite forms a pink colored Calmagite-$Mg^{2+}$ complex with an absorption maximum at ~520 nm. According to Lambert-Beer's law, $Mg^{2+}$ concentration between 0-2.5 mM has a linear correlation with absorbance value at 520 nm. Thus, $[Mg^{2+}]$ in a sample can be obtained from the absorbance at 520 nm and a standard curve.

For all $[Mg^{2+}]$ measurements through out this study, a Calmagite working solution containing EGTA, Strontium chloride and AMP was prepared according to the above cited references. The purpose of adding EGTA, strontium chloride and AMP was to remove the interference of calcium and iron. A standard curve was first generated by using a series of either $MgSO_4$ or $MgCl_2$ solutions with known concentrations (standard solutions). A small volume (50 uL) of a standard solution was added to 2 mL dye working solution in a quartz cuvvete. Following a brief incubation, the absorbance of the solution at 520 nm was measured to give $A_1$ using a Beckman Uv/Vis 530 spectrophotometer. Subsequently, 5 uL of 150 mM EDTA solution was added to the above solution, followed by 1 minute of incubation to break up the Magnesium-Calmagite complex. The solution was incubated until the absorbance at 520 nm became stable. This stable absorbance value, $A_2$, was the background absorbance. A standard curve was generated by plotting $(A_1-A_2)$ vs. $[Mg^{2+}]_{standard}$. Plasma or urine samples were measured according to the same procedure used for generating the standard curve except that the urine samples were diluted, if necessary, to below 2.5 mM. Magnesium concentrations of the samples were then obtained from the $(A_1-A_2)$ values and standard curve. The bioavailability of three magnesium compositions, magnesium diglycinate, magnesium gluconate and magnesium gluconate in milk (at 0.8 mg/mL), were compared in three healthy male volunteers. Before magnesium supplementation began, urine samples of the volunteers were collected for 2 days. Then, the volunteers were asked to take either of the three magnesium compositions at the amount of 200 mg magnesium each time twice per day for 2 days, during which the urine samples were collected. All urine samples were analyzed for their magnesium contents using the dye method as described in above. Cumulative urinary magnesium excretion was used to determine the bioavailability (magnesium absorption rate) of each magnesium composition according to the reported procedure using the formula below (Drenick, E. J., et al., J Clin Endocrinol Metab, 1969. 29(10): p. 1341-8; Lim & Jacob, Metabolism, 1972. 21(11): p. 1045-51):

$$k_x=(Mg_u^2-Mg_u^1)/dosage$$

where $k_x$ is the magnesium absorption rate; $Mg_u^2$ is the amount of 2-day urine magnesium with magnesium supplementation; $Mg_u^1$ is the amount of 2-day urine magnesium without magnesium supplementation; and dosage is the daily amount of magnesium taken.

Figure 25:
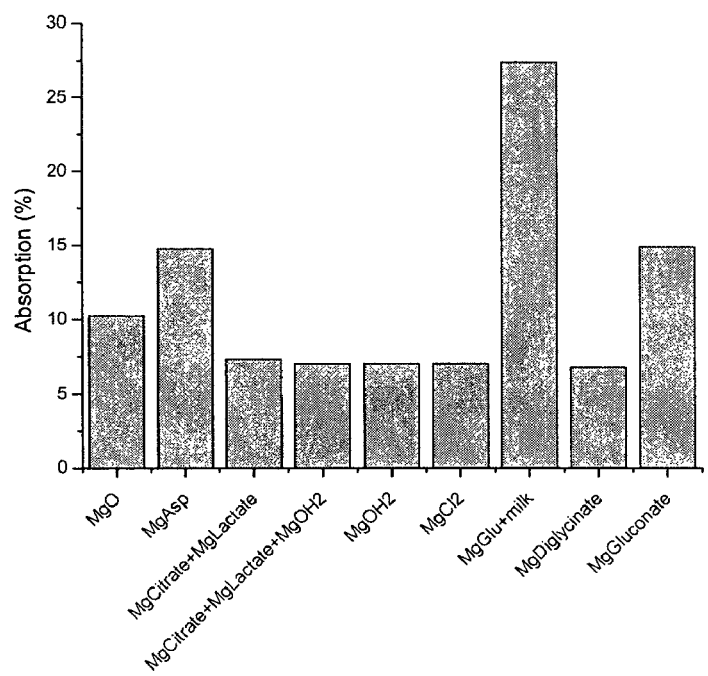
FIG. 25 is a graphical representation of the bioavailability of different magnesium-containing compositions.

The bioavailability comparison of various magnesium compounds utilizing this methodology were determined in several human subjects. We collected data for magnesium gluconate+milk, magnesium diglycinate and magnesium gluconate. Results are shown in FIG. 25. For comparison, the availability of other magnesium compounds determined by others is also shown in FIG. 25. See Muhlbauer, et al., *Eur. J. Clin. Pharmacol.*, 40:437-8 (1991); see also Bohmer, et al., *Magnes. Trace Elem.* 9: 272-8 (1990). This study demonstrates that there are differences in bioavailability among magnesium paired with different counter ions and that, for some counter ions, delivery of magnesium with milk enhances bioavailability.

Example 24

Measuring Plasma, Serum or Urine Magnesium Concentration

Two groups of 6 AD mice were each fed an magnesium diet (test group) and a normal diet (control group) at 5 month of age, respectively, as described above. The cognitive function of the two groups of animals was then assessed at 21 mouth of age using the novel object recognition test as described above. After the test, the animals were anesthetized with 10% chloral hydrate (4 ul per gram) and then transcardially perfused with ice-cold PBS (pH 7.4, without $CaCl_2$ and $MgCl_2$) and 4% paraformaldehyde. Next, the whole brain of each animal was immediately removed and post-fixed in 4% paraformaldehyde at 4° C. for 2 hours at room temperature. The brainstem portion was cut off the whole brain in a clean dish cover and then placed in a 15 ml-sized tube to measure the weight of the tissue. Eight mL concentrated nitric acid was added to each tupe containing tissue. The tubes were then placed in a sample digestion microwave oven to digest the samples using a programmed three-stage digestion procedure according to the table 1

TABLE 1

Microwave digestion steps

| Step | Power (W) | Heating time (min) | Pressure (Psi) | Ultimate temperature (° C.) | Holding time (min) |
|---|---|---|---|---|---|
| 1 | 1200 | 6 | 800 | 120 | 2 |
| 2 | 1200 | 3 | 800 | 150 | 2 |
| 3 | 1200 | 5 | 800 | 180 | 20 |

The pellucid solutions formed after the digestion were cooled to room temperature and then each transferred to a separate beaker with NanoPure water. The nitric acid in the beakers was removed by evaporation at 170° C. The residue in each beaker was then re-diluted to 25 ml in a volumetric flask. The magnesium contents of the solutions were determined by inductively coupled plasma optical emission spectroscopy (ICP-OES). (IRIS, Intrepid II XSP, Thermo Electron, USA). From the total amount of the magnesium in each solution and the weight of the tissue sample, the magnesium concentration of the brainstem was obtained.

Figure 26:
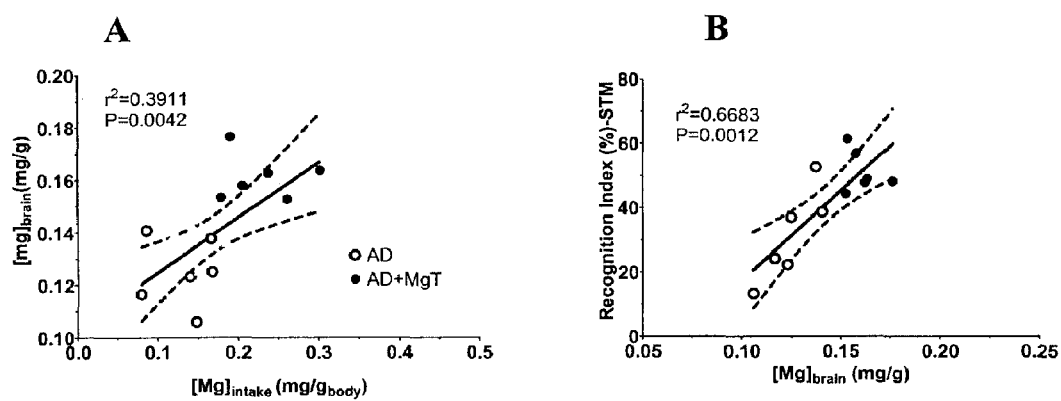
FIG. 26 is a graphical representation of the correlation between magnesium concentration in the brain, the amount of magnesium intake (panel A) and the correlation between short term memory effects (panel B).

Correlation between brain magnesium concentration and daily magnesium intake or between cognitive function level and brain magnesium concentration was plotted and is shown in FIG. 26. Panel A demonstrates the correlation between magnesium concentration in the brain (mg magnesium per gram tissue) and the amount of magnesium daily intake (mg magnesium per gram body weight). Panel B demonstrates the correlation between short-term memory (as assessed by the novel recognition test) and magnesium concentration in the brain. As can be seen from these results, we have found that the amount of magnesium intake in AD mice is linearly correlated to the amount of brain magnesium, which in turn was linearly correlated to the level of cognitive function. This data strongly suggests a causal relationship between elevation of brain magnesium level and improvement of cognitive function.

Example 25

Measuring Plasma, Serum or Urine Magnesium Concentration

Another way to define the bioavailability of a magnesium composition is the ability of the composition to deliver magnesium to tissues. In many ways, this is the ultimate criteria for judging the bioavailability of a magnesium composition. Merely to deliver magnesium to the blood stream is no guarantee that the magnesium will enter the right tissues because the newly absorbed magnesium may simply excreted from the urine. As shown in the previous example, for improved cognitive function, it is important that magnesium be delivered to the brain.

Figure 27:
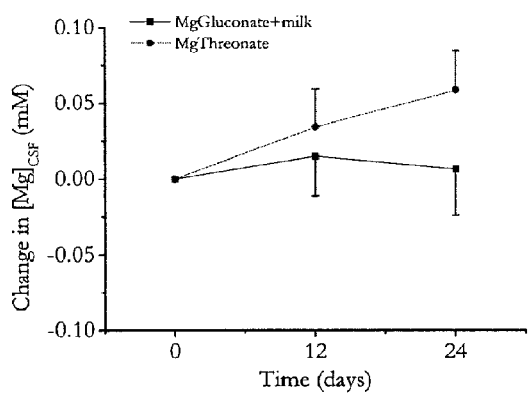
FIG. 27 is a graphic representation of the effectiveness of magnesium threonate, compared with magnesium gluconate in milk, in absorption by the brain (panel A). Also shown is a comparison of the results of a memory test using magnesium threonate (panel B) and magnesium gluconate+milk (panel C).
Figure 27:
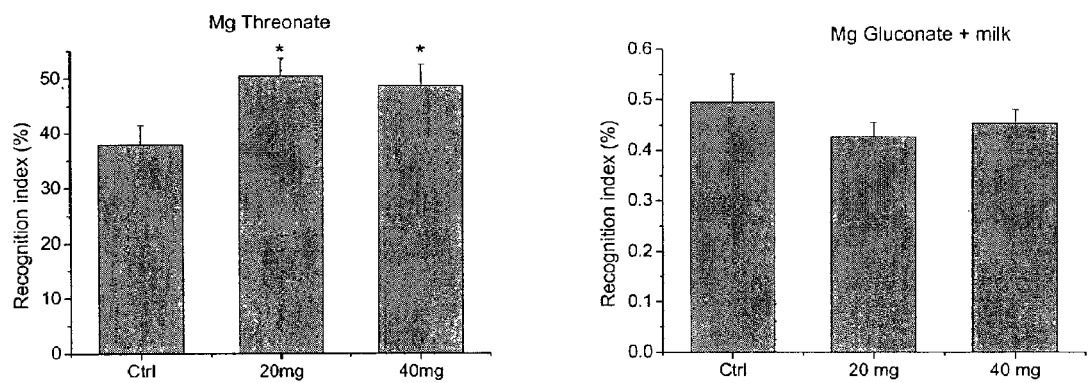

Magnesium threonate is better in targeting magnesium to the brain, compared with magnesium gluconate in milk as shown in FIG. 27A. This is a surprising finding as other studies indicate that magnesium gluconate in milk has higher bioavailability to the blood than magnesium threonate (data not shown). Animal behavior data also supports that magnesium threonate is better than magnesium gluconate in milk at delivering magnesium to the brain. FIG. 27B shows that rats receiving magnesium threonate supplements in water (as described previously) at the indicated amount showed marked improvement in their short term memory in a novel object recognition test (as described previously). FIG. 27C shows that rats receiving magnesium gluconate dissolved in milk did not demonstrate any improvement in short term memory function in a novel-object recognition test.

These data indicate that the effectiveness of raising brain magnesium by a given magnesium compound is desirable enhancing the animals' memory function. Furthermore, the data suggest that the threonate counter ion may facilitate the absorption of magnesium by tissues, particularly brain tissues. Thus, in addition to the use of magnesium threonate for supplementing magnesium, differential utilization of magnesium-counter ion compositions may yield a variety of other possible methods for increasing magnesium absorption by targeted tissues. For example, a non-magnesium threonate may be used in combination with any other suitable magnesium compound for enhanced bioavailability of the compound. Examples of non-magnesium threonate compounds include, but are not limited to, sodium threonate, potassium threonate, threonic acid, calcium threonate. Alternatively, a precursor threonate compound may be used in the same manner. Examples of such a precursor threonate compound include but not limited to ascorbate and a threonate ester. Ascorbate is metabolized in the body to form threonate, while a threonate ester, such as threonate ethyl ester can become hydrolyzed in the body to form threonate. When a threonate or a precursor threonate compound is used to enhance the bioavailability of another magnesium compound, the two compounds may or may not be physically combined. When taken separately, they may be taken at the same time or taken at separate times.

Example 26

Measuring Magnesium Concentration Under Fasting Conditions to Determine Supplement Levels This example provides one method of the present invention developed to increase $[Mg]_o$, the concentration of $Mg^{2+}$ in the extracellular compartment, to a predetermined target level. This change of $[Mg]_o$ achieves an improvement of various physiological functions.

Unlike for sodium or calcium, there do not appear to be major hormonal homeostatic mechanisms for regulating serum magnesium. The normal range is the result of a balance between the gastrointestinal and renal absorption and the excretion processes. For this purpose, we analyze the in- and out-flux of magnesium in a multi-compartment model. The description of the multi-compartment model is given next:

$Mg_f$ is the amount of magnesium absorbed through food each day, $[Mg]_o$ is the concentration of $Mg^{2+}$ in the extracellular compartment, $[Mg]_i$ is the concentration of $Mg^{2+}$ in the intracellular compartment, $Mg_u$ is the daily excretion of Mg from the kidney, $Mg_s$ is the daily loss of magnesium through sweat, and $k+_1$ and $k_{-i}$ are the rate constants of the $Mg^{2+}$ governing the exchange between $[Mg]_o$ and $[Mg]_i$. Under the equilibrium condition, net flux (all represented by the total amount for one day) from $[Mg]_o$ to $[Mg]_i$ are zero, i.e. inflow and outflow perfectly balance:

$$Mg_f = Mg_u([Mg]_o^1) + Mg_s \quad (1)$$

Next, we describe the case, where one decides to increase $[Mg]_o^1$ to the higher value $[Mg]_o^2$. To achieve this goal, one needs in the equilibrium to take exactly enough absorbed supplement $Mg_{su}$ to cover the additional loses $$Mg_f + Mg_{su} = Mg_u([Mg]_o^2) + Mg_s, \quad (2)$$

where $Mg_u([Mg]_o^2)$ is the Mg in urine after the Mg supplement has been added and the new equilibrium has been reached. If we rearrange the equation, we get $$Mg_f - Mg_s + Mg_{su} = Mg_u([Mg]_o^2) \text{ and } Mg_f - Mg_s = Mg_u([Mg]_o^1).$$

This leads to $$Mg_{su} = Mg_u([Mg]_o^2) - Mg_u([Mg]_o^1). \quad (3)$$

To calculate the $Mg_{su}$ required to achieve $[Mg]_o^2$, one needs to determine the relationship between $[Mg]_o$ and $Mg_u$.

Relationship between $[Mg]_o$ and $Mg_u$

In the kidney, Mg in blood is filtered by glomerulus and reabsorbed in tubular cells. The amount of Mg filtered is the products of the glomerular filtration rate (GFR), $[Mg]_o$, and the molecular weight of Mg ($Mg_{mw}$) ($GFR \cdot [Mg]_o \cdot Mg_{mw}$)

The filtered magnesium is reabsorbed in renal tubules. When $[Mg]_o$ is below a certain point, the kidney is capable of retaining all of the filtered Mg, and $Mg_u$ is near zero. At this point, the urine magnesium excretion seems linearly correlated with $[Mg]_o$. To quantify this process, we studied the relationship between $[Mg]_o$ and $Mg_u$ in 3 human volunteers. The blood and urine magnesium were sampled every four hours in day during fasting. Their relationships are plotted in FIG. 28A. Evidently, the relationship between urine magnesium and $[Mg]_o$ is linear.

Figure 28:
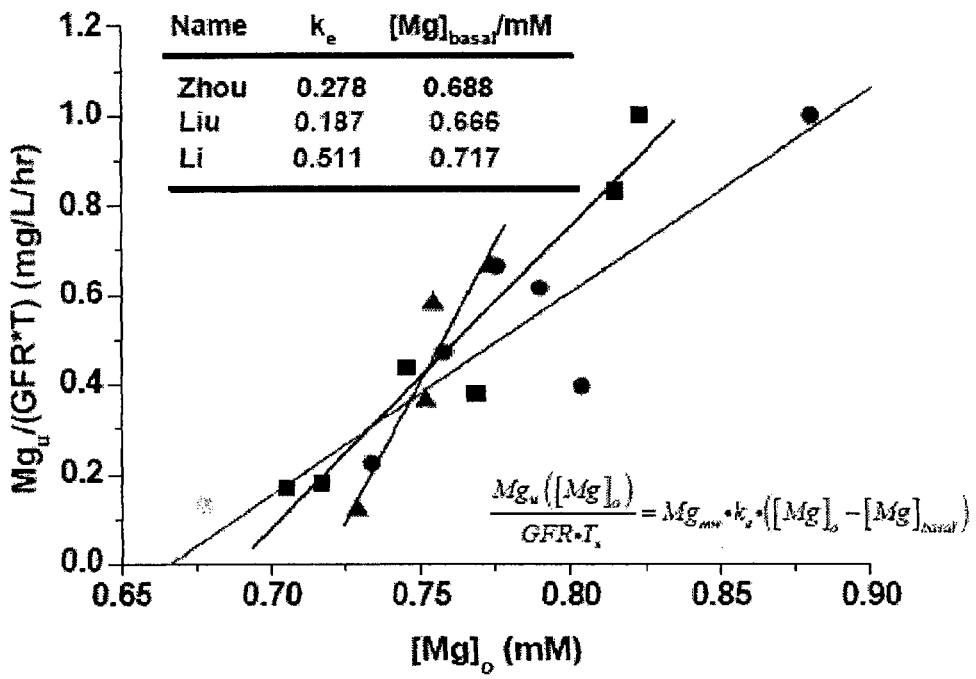
FIG. 28 is a graphic representation of a method of determining an effective magnesium dosing regimen based on basal magnesium concentration under fasting conditions. Panel A demonstrates the relationship between blood and urine magnesium concentration and Panel B shows the use of magnesium concentration in the extracellular compartment and in urine to determine proper dosing.
Figure 28:
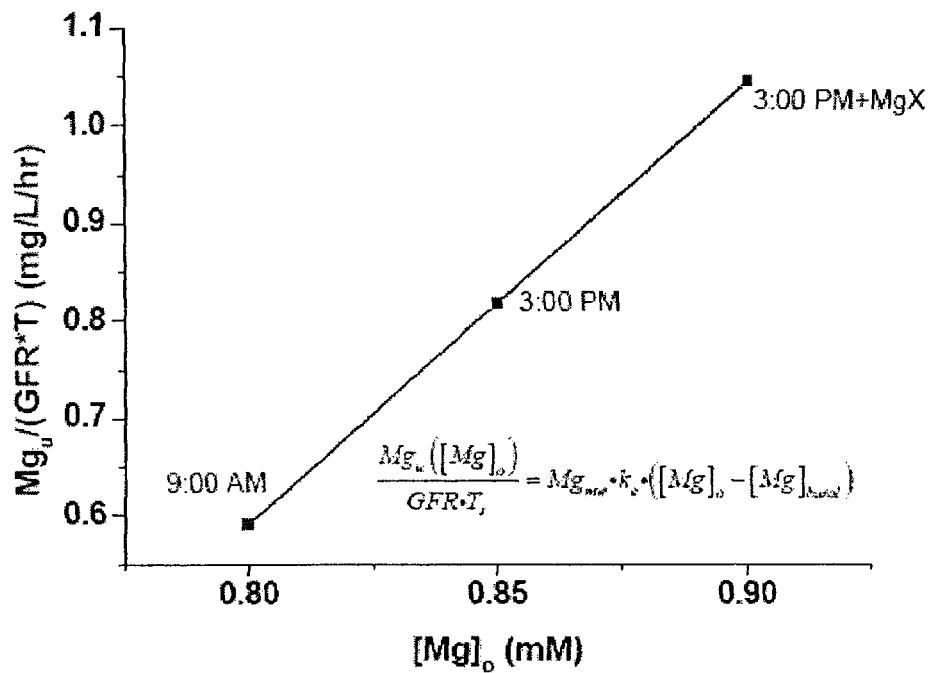

From this data, one can get an empirical formula that predicts the general relationship between $[Mg]_o$ and $Mg_u$ in the relevant daily physiological range of 0.7-0.85 mM, i.e. range achieved without extensive fasting. We define $[Mg]_o$ at the point where urine losses go to zero to be $[Mg]_{basal}$. The excretion of Mg through kidney might then be taken to be proportional to $[Mg]_o - [Mg]_{basal}$. Thus, for a given GFR and a period of time (T (hour)), we get $$\frac{Mg_u([Mg]_o)}{GFR \cdot T_s} = Mg_{mw} \cdot k_e \cdot ([Mg]_o - [Mg]_{basal}) \quad (4)$$

Where $k_e$ is the proportionality constant, which physiologically defines the rate of Mg loss through the kidneys at a given $[Mg]_o$. The data fitting with equation 4 seems sufficient to predict the relationship between $[Mg]_o$ and $[Mg]_u$ (FIG. 28A).

Combining equation 3 and 4, the amount of net Mg needed as a supplement to achieve a higher $[Mg]_o$ can be predicted by the following equation:

$$Mg_{su} = GFR \cdot T \cdot Mg_{mw} \cdot k_e \cdot ([Mg]_o^2 - [Mg]_o^1) \quad (5)$$

For a Mg compound X with bioavailability of $k_x$, the amount of Mg compound one needs to take is $$Mg_x = Mg_{su} k_x.$$

Applying the above to Routine followed by users to determine initial Mg status, choice of correct supplement amount and feedback loop to achieve desired result:

1) Determine body Mg status: using $[Mg]_{plasma}$ at 9:00 AM before breakfast and after fasting 12 hours.
2) Decide the target $[Mg]_{plasma}$
3) Calculation of $k_e$ and $[Mg]_{basal}$ using following procedures:
   a. Day one: Measure $[Mg]_{plasma}$ at 9:00 AM before breakfast and collect $Mg_u$ from 8:30 AM to 10:30 AM.
   b. Measure $[Mg]_{plasma}$ at 3:00 PM and collect $Mg_u$ from 2:30 PM to 4:30 PM (2-4 hours after lunch at the expected peak of $[Mg]_{plasma}$ and $Mg_u$).
   c. Day two: Take 300 mg magnesium Gluconate dissolved in 200 ml of milk at 12:00 PM with normal food. Measure $[Mg]_{Plasma}$ at 3:00 PM and collect $Mg_u$ from 2:30 PM to 4:30 PM.
   d. From the blood and urine sample, one can determine averaged GFR for each pair of blood aria urine samples.
   e. Plot the collected data and fit them with a linear equation $$\frac{Mg_u([Mg]_o)}{GFR \cdot T_s} = Mg_{mw} \cdot k_e \cdot [Mg]_{plasma} + b$$

f. Finally, $$[Mg]_{basal} = -b/(Mg_{mw} \cdot k_e) \quad (6)$$

g. See FIG. 28B
4) Optimal Dosage:
With the parameters determined from above procedures, one can calculate the proper dosage with following equations.

$$Mg_x = GFR \cdot T \cdot Mg_{mw} \cdot k_e \cdot ([Mg]_o^1)/k_x \quad (7)$$

Predictions for three human subjects utilizing this method are shown in Table 2.

| Subj. | GFR | Time | [Mg]basal | [Mg]initial | [Mg]final | ke | U initial | U final | Mgsu | Kx | MgX |
|---|---|---|---|---|---|---|---|---|---|---|---|
| L | 7.5 | 24 | 0.67 | 0.78 | 0.88 | 0.19 | 93 | 175 | 82 | 0.3 | 273 |
| Z | 7.5 | 24 | 0.69 | 0.78 | 0.88 | 0.28 | 112 | 233 | 122 | 0.3 | 405 |
| LX | 7.5 | 24 | 0.72 | 0.77 | 0.88 | 0.51 | 118 | 364 | 246 | 0.3 | 820 |

5) The most effective way of loading: A sustained-release form of Mg compound (within 12 hours) taken before sleep.
6) checking procedures:
  a. Previous study suggests that 6 to 18 days are required for equilibrium to be established following changes in magnesium intake. We recommend checking body Mg status 1 month after daily Mg supplement intake has started, assuming that Mg status has already reached approximately the new equilibrium. The $[Mg]_{plasma}$ and urine Mg will be taken using same procedure listed in step 3a without taking Mg supplement in day before testing. If the dosage is appropriate, $[Mg]_{plasma}$ will be close (+/−10%, more accurately +5% to −15% of the correct value, since the approach is from below) to the desired level and $Mg_u$ will be close to $$Mg_u = GFR \cdot T \cdot Mg_{mw} \cdot k_e \cdot ([Mg]_o^2 - [Mg]_{basal})$$

b. If $[Mg]_{plasma}$ and $Mg_u$ deviate from the target values, the error is most likely due to an inaccurate estimate of $k_x$. As bioavailability ($k_x$) for a Mg compound might not be constant among the population, one can use the these data to calculate the efficacy of loading Mg compound into intracellular compartment ($k'_x$).

$$k'_x = (Mg_u^2 - Mg_u^1)/Mg_x \qquad (8)$$

When $k'_x$ is determined, equation 7 can be used to recalculate the dosage and check the $[Mg]_{plasma}$ and $Mg_u$ one month later. This procedure can be repeated until the $[Mg]_{plasma}$ reaches the desired value.

c. Procedure 6b is preferably repeated biannually.

Example 27

Effect of Magnesium Treatment on Synaptic Protection in AD Mice

Figure 29:
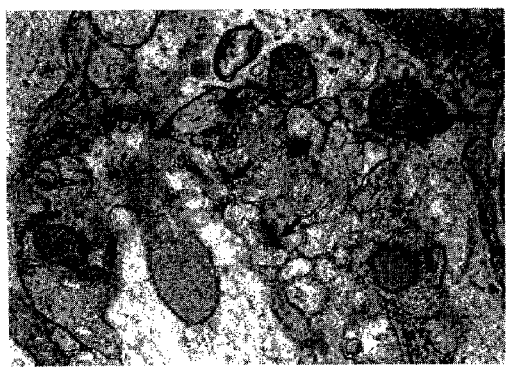
FIG. 29 shows the protection of synapse loss in AD mice by magnesium threonate treatment. Panel A demonstrates the lower synapses count in dentate gyrus of hippocampus of AD mice. Panel B demonstrates the higher synaptic density in the same region. Panel C demonstrates the quantitative comparison of the synaptic densities in AD mice, AD mice with MgT treatment, and wild type mice.
Figure 29:
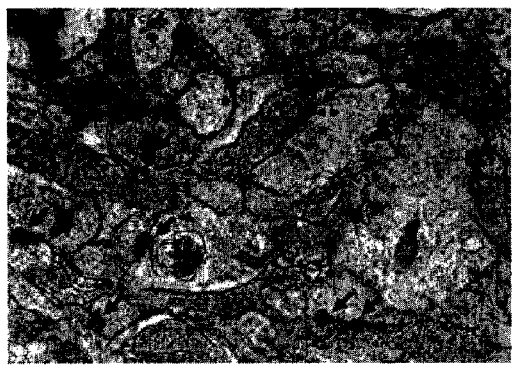
Figure 29:
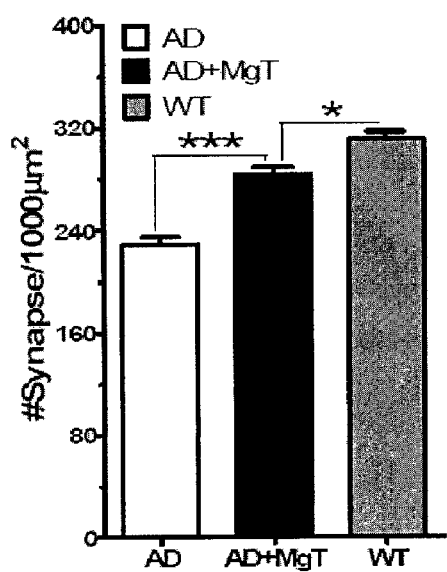

In this example we examine the ability of magnesium threonate treatment to protect against synapse loss in AD mice. The same group of animals used for the memory test in example 14 are sacrificed. The brains of the animals were then fixed for electronmicroscopic analysis to count the number of synapses per unit area (synaptic density). Samples were stained so as to indicate the synapses (FIGS. 29 A and B, synapses indicated by arrows).

FIG. 29A shows the lower synapse count in the dentate gyrus of the hippocampus of AD mice. FIG. 29B shows the higher synaptic density in the same region in AD mice treated with magnesium threonate supplemented diet. FIG. 29C shows the results of a quantitative comparison of the synaptic densities in AD mice, AD mice receiving magnesium threonate treatment, and wild type mice. The synaptic density in AD mice is significantly lower than for the wild type mice or AD mice under MgT treatment (p<0.001). However, the synaptic density in AD mice receiving magnesium threonate treatment is more similar to wild type mice. These results indicate the protective effect of magnesium treatment on synaptic loss in AD progression.

A composition for administration to a subject, such as oral administration to a subject, for example, has been described herein. Such a composition may comprise at least one magnesium-counter ion compound. A magnesium-counter ion composition described herein may be useful for any of a variety of applications and purposes described herein, such as maintaining, enhancing, and/or improving health, nutrition, and/or another condition of a subject, and/or cognitive, learning, and/or memory function, for example. A magnesium-counter ion composition described herein may be useful for administration to a subject presenting magnesium deficiency, mild cognitive impairment, Alzheimer's disease, attention deficit hyperactivity disorder, ALS, Parkinson's disease, diabetes, migraine, anxiety disorder, mood disorder, and/or hypertension, merely by way of example.

A kit may comprise at least one component of any magnesium-counter ion composition described herein or any magnesium-counter ion composition described herein. A kit may further comprise a vehicle for administering at least one such component or such a composition to a subject, such as a drinking vessel for a liquid component or composition, merely by way of example, or a holding vessel for any component or composition and a vehicle for moving same from the holding vessel to a mouth of a subject, such as a bowl and a spoon, merely by way of example.

A method of providing magnesium supplementation to a subject may be useful to a subject in any of the ways described herein. Such a method may comprise administering to a subject, such as orally administering to a subject, at least one magnesium-counter ion compound. Such a method may comprise providing any suitable amount, concentration, or a dosage of elemental magnesium associated with the at least one magnesium-counter ion compound to a subject.

A composition and/or a method described herein may be useful for purposes described herein, such as maintaining, enhancing, and/or improving health, nutrition, and/or another condition of a subject, and/or cognitive, learning, and/or memory function, for example, such as magnesium deficiency, mild cognitive impairment, Alzheimer's disease, attention deficit hyperactivity disorder, ALS, Parkinson's disease, diabetes, migraine, anxiety, mood, and hypertension, merely by way of example. A composition and/or a method described herein may be useful for administration to a subject presenting magnesium deficiency, mild cognitive impairment, Alzheimer's disease, attention deficit hyperactivity disorder, ALS, Parkinson's disease, diabetes, migraine, anxiety disorder, mood disorder, and/or hypertension, merely by way of example.

Various modifications, processes, as well as numerous structures that may be applicable herein will be apparent. Various aspects, features or embodiments may have been explained or described in relation to understandings, beliefs, theories, underlying assumptions, and/or working or prophetic examples, although it will be understood that any particular understanding, belief, theory, underlying assumption, and/or working or prophetic example is not limiting. Although the various aspects and features may have been described with respect to various embodiments and specific examples herein, it will be understood that any of same is not limiting with respect to the full scope of the appended claims or other claims that may be associated with this application.

The examples set forth above are given to provide those of ordinary skill in the art with a complete disclosure and description of how to make and use various embodiments of the methods and systems disclosed herein, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

We claim:

1. A method of increasing magnesium in a subject comprising administering to said subject for a period of at least about 1 month a composition formulated for oral consumption, said composition comprising at least 10 mg magnesium threonate.

2. The method of claim 1, further comprising measuring a body fluid concentration of magnesium in the subject after fasting for at least about twelve hours, wherein said body fluid concentration is serum concentration, plasma concentration, or cerebrospinal fluid concentration.

3. The method of claim 1, wherein said magnesium threonate is provided in a magnesium-supplemented foodstuff.

4. A method of supplementing magnesium to a subject, comprising the steps of:

administering to said subject a composition comprising magnesium threonate formulated for oral consumption in an amount that is effective in increasing an initial physiological concentration of magnesium of said subject by at least about 10%, wherein the initial physiological concentration is measured from a body fluid sample taken from said subject under a fasting condition.

5. The method of claim 4, wherein said concentration of magnesium is measured after fasting for at least about twelve hours.

6. The method of claim 4, wherein said physiological concentration is serum concentration, plasma concentration, urine concentration, or cerebrospinal fluid concentration.

7. The method of claim 4, wherein said magnesium threonate is provided in a magnesium-supplemented foodstuff.

8. The method of claim 4, further comprising the step of determining a physiological concentration of magnesium after said subject has begun said dosing regimen.

9. The method of claim 1, wherein said composition is administered for a period of greater than 6 months.

10. The method of claim 1, wherein said composition is administered for a period of greater than 1 year.

11. The method of claim 1, wherein the composition is in a unit dosage form.

12. The method of claim 1, wherein the composition is a dietary supplement.

13. The method of claim 4, wherein the composition is in a unit dosage form.

14. The method of claim 4, wherein the composition is a dietary supplement.

* * * * *